(12) United States Patent
Schaller et al.

(10) Patent No.: US 10,426,629 B2
(45) Date of Patent: Oct. 1, 2019

(54) DEVICES FOR TREATING THE SPINE

(71) Applicant: Benvenue Medical, Inc., Santa Clara, CA (US)

(72) Inventors: Laurent Schaller, Los Altos, CA (US); Timothy McGrath, Fremont, CA (US); Ryan Connolly, Menlo Park, CA (US); David Needleman, San Carlos, CA (US); Steven Golden, Menlo Park, CA (US); John Ashley, San Francisco, CA (US); James Lee, San Mateo, CA (US); Jeffrey Emery, Emerald Hills, CA (US); J. Brook Burley, Mountain View, CA (US)

(73) Assignee: Benvenue Medical, Inc., Santa Clara, CA (US)

( * ) Notice: Subject to any disclaimer, the term of this patent is extended or adjusted under 35 U.S.C. 154(b) by 0 days.

(21) Appl. No.: 16/151,975

(22) Filed: Oct. 4, 2018

(65) Prior Publication Data

US 2019/0029844 A1 Jan. 31, 2019

Related U.S. Application Data

(60) Continuation of application No. 15/994,050, filed on May 31, 2018, which is a continuation of application
(Continued)

(51) Int. Cl.
*A61F 2/44* (2006.01)
*A61F 2/46* (2006.01)
(Continued)

(52) U.S. Cl.
CPC ........ *A61F 2/4425* (2013.01); *A61B 17/7094* (2013.01); *A61B 17/8852* (2013.01);
(Continued)

(58) Field of Classification Search
CPC .. A61F 2/4455; A61F 2/4611; A61B 17/7094; A61B 17/8852; A61B 17/8858
See application file for complete search history.

(56) References Cited

U.S. PATENT DOCUMENTS 1,965,653 A 7/1934 Kennedy
3,091,237 A 5/1963 Skinner
(Continued)

FOREIGN PATENT DOCUMENTS

DE 197 10 392 C1 7/1999
DE 202006005868 6/2006
(Continued)

OTHER PUBLICATIONS

Extended European Search Report for European Patent Application No. 08730402.8, dated Feb. 18, 2013.
(Continued)

*Primary Examiner* — Julianna N Harvey
(74) *Attorney, Agent, or Firm* — Cook Alex Ltd.

(57) ABSTRACT

Method and apparatus are disclosed for distracting tissue and particularly spinal tissue. The device and method may include insertion of at least one elongated member and an augmenting member to form a structure between the tissues to be distraction, such that a dimensional aspect of the structure is augmented upon movement of the augmenting structure.

22 Claims, 18 Drawing Sheets

Related U.S. Application Data

No. 15/297,634, filed on Oct. 19, 2016, which is a continuation of application No. 14/613,551, filed on Feb. 4, 2015, now Pat. No. 9,642,712, which is a division of application No. 13/869,075, filed on Apr. 24, 2013, now Pat. No. 8,968,408, which is a continuation of application No. 12/035,298, filed on Feb. 21, 2008, now Pat. No. 8,454,617.

(60) Provisional application No. 60/936,974, filed on Jun. 22, 2007.

(51) Int. Cl.
*A61B 17/88* (2006.01)
*A61B 17/70* (2006.01)
*A61F 2/30* (2006.01)
*B33Y 80/00* (2015.01)
*A61F 2/28* (2006.01)
*A61B 17/02* (2006.01)

(52) U.S. Cl.
CPC .......... *A61F 2/44* (2013.01); *A61F 2/442* (2013.01); *A61F 2/4455* (2013.01); *A61F 2/4611* (2013.01); *H05K 999/99* (2013.01); *A61B 2017/0256* (2013.01); *A61F 2002/2835* (2013.01); *A61F 2002/3008* (2013.01); *A61F 2002/3052* (2013.01); *A61F 2002/30092* (2013.01); *A61F 2002/30153* (2013.01); *A61F 2002/30235* (2013.01); *A61F 2002/30263* (2013.01); *A61F 2002/30289* (2013.01); *A61F 2002/30462* (2013.01); *A61F 2002/30579* (2013.01); *A61F 2002/30594* (2013.01); *A61F 2002/30598* (2013.01); *A61F 2002/30601* (2013.01); *A61F 2002/30677* (2013.01); *A61F 2002/30772* (2013.01); *A61F 2002/448* (2013.01); *A61F 2002/4627* (2013.01); *A61F 2002/4635* (2013.01); *A61F 2002/4677* (2013.01); *A61F 2002/4683* (2013.01); *A61F 2002/4688* (2013.01); *A61F 2210/0014* (2013.01); *A61F 2210/0071* (2013.01); *A61F 2220/0025* (2013.01); *A61F 2220/0075* (2013.01); *A61F 2230/0019* (2013.01); *A61F 2230/0069* (2013.01); *A61F 2230/0084* (2013.01); *A61F 2230/0091* (2013.01); *A61F 2310/00293* (2013.01); *B33Y 80/00* (2014.12)

(56) References Cited

U.S. PATENT DOCUMENTS

| | | |
|---|---|---|
| 3,112,743 A | 12/1963 | Cochran et al. |
| 3,648,294 A | 3/1972 | Shahrestani |
| 3,800,788 A | 4/1974 | White |
| 3,867,728 A | 2/1975 | Stubstad et al. |
| 3,875,595 A | 4/1975 | Froning |
| 3,889,665 A | 6/1975 | Ling et al. |
| 3,964,480 A | 6/1976 | Froning |
| 4,262,676 A | 4/1981 | Jamshlidl |
| 4,274,163 A | 6/1981 | Malcom et al. |
| 4,312,337 A | 1/1982 | Donohue |
| 4,313,434 A | 2/1982 | Segal |
| 4,399,814 A | 8/1983 | Pratt, Jr. et al. |
| 4,462,394 A | 7/1984 | Jacobs |
| 4,466,435 A | 8/1984 | Murray |
| 4,467,479 A | 8/1984 | Brody |
| 4,488,549 A | 12/1984 | Lee et al. |
| 4,562,598 A | 1/1986 | Kranz |
| 4,595,006 A | 6/1986 | Burke et al. |
| 4,625,722 A | 12/1986 | Murray |
| 4,627,434 A | 12/1986 | Murray |
| 4,628,945 A | 12/1986 | Johnson, Jr. |
| 4,630,616 A | 12/1986 | Tretinyak |
| 4,665,906 A | 5/1987 | Jervis |
| 4,686,973 A | 8/1987 | Frisch |
| 4,697,584 A | 10/1987 | Haynes |
| 4,706,670 A | 11/1987 | Andersen et al. |
| 4,714,478 A | 12/1987 | Fischer |
| 4,743,256 A | 5/1988 | Brantigan |
| 4,772,287 A | 9/1988 | Ray et al. |
| 4,834,069 A | 5/1989 | Umeda |
| 4,838,282 A | 6/1989 | Strasser et al. |
| 4,863,476 A | 9/1989 | Shepperd |
| 4,878,915 A | 11/1989 | Brantigan |
| 4,888,022 A | 12/1989 | Huebsch |
| 4,888,024 A | 12/1989 | Powlan |
| 4,892,550 A | 1/1990 | Hubsch |
| 4,896,662 A | 1/1990 | Noble |
| 4,898,577 A | 2/1990 | Badger et al. |
| 4,904,261 A | 2/1990 | Dove et al. |
| 4,941,466 A | 7/1990 | Romano |
| 4,961,740 A | 10/1990 | Ray et al. |
| 4,969,888 A | 11/1990 | Scholten et al. |
| 5,015,247 A | 6/1991 | Michelson |
| 5,015,255 A | 6/1991 | Kuslich |
| 5,051,189 A | 9/1991 | Farrah |
| 5,053,035 A | 10/1991 | McLaren |
| 5,055,104 A | 10/1991 | Ray |
| 5,059,193 A | 10/1991 | Kuslich |
| 5,071,435 A | 12/1991 | Fuchs et al. |
| 5,098,435 A | 3/1992 | Stednitz et al. |
| 5,102,413 A | 4/1992 | Poddar |
| 5,108,404 A | 4/1992 | Scholten et al. |
| 5,122,130 A | 6/1992 | Keller |
| 5,123,926 A | 6/1992 | Pisharodi |
| 5,147,366 A | 9/1992 | Arroyo et al. |
| 5,163,989 A | 11/1992 | Campbell et al. |
| 5,171,280 A | 12/1992 | Baumgartner |
| 5,176,683 A | 1/1993 | Kimsey et al. |
| 5,176,692 A | 1/1993 | Wilk et al. |
| 5,183,052 A | 2/1993 | Terwilliger |
| 5,192,327 A | 3/1993 | Brantigan |
| 5,228,441 A | 7/1993 | Lundquist |
| 5,242,448 A | 9/1993 | Petline et al. |
| 5,242,879 A | 9/1993 | Abe et al. |
| 5,257,632 A | 11/1993 | Turkel et al. |
| 5,263,953 A | 11/1993 | Bagby |
| 5,285,795 A | 2/1994 | Ryan et al. |
| 5,303,718 A | 4/1994 | Krajicek |
| 5,306,308 A | 4/1994 | Gross et al. |
| 5,306,310 A | 4/1994 | Siebels |
| 5,322,505 A | 6/1994 | Krause et al. |
| 5,330,429 A | 7/1994 | Noguchi et al. |
| 5,331,975 A | 7/1994 | Bonutti |
| 5,361,752 A | 11/1994 | Moll et al. |
| 5,383,932 A | 1/1995 | Wilson et al. |
| 5,385,151 A | 1/1995 | Scarfone et al. |
| 5,423,816 A | 6/1995 | Lin |
| 5,423,817 A | 6/1995 | Lin |
| 5,423,850 A | 6/1995 | Berger |
| 5,431,658 A | 7/1995 | Moskovich |
| 5,441,538 A | 8/1995 | Bonutti |
| 5,454,365 A | 10/1995 | Bonutti |
| 5,454,827 A | 10/1995 | Aust et al. |
| 5,462,563 A | 10/1995 | Shearer et al. |
| 5,468,245 A | 11/1995 | Vargas, III |
| 5,480,400 A | 1/1996 | Berger |
| 5,484,437 A | 1/1996 | Michelson |
| 5,509,923 A | 4/1996 | Middleman et al. |
| 5,514,143 A | 5/1996 | Bonutti et al. |
| 5,514,153 A | 5/1996 | Bonutti |
| 5,522,790 A | 5/1996 | Moll et al. |
| 5,522,398 A | 6/1996 | Goldenberg et al. |
| 5,522,846 A | 6/1996 | Bonutti |
| 5,527,343 A | 6/1996 | Bonutti |
| 5,527,624 A | 6/1996 | Higgins et al. |
| 5,531,856 A | 7/1996 | Moll et al. |
| 5,534,023 A | 7/1996 | Henley |
| 5,538,009 A | 7/1996 | Byrne et al. |
| 5,540,711 A | 7/1996 | Kieturakis et al. |

(56) References Cited

U.S. PATENT DOCUMENTS

| | | |
|---|---|---|
| 5,545,222 A | 8/1996 | Bonutti |
| 5,549,679 A | 8/1996 | Kuslich |
| 5,562,736 A | 10/1996 | Ray et al. |
| 5,571,109 A | 11/1996 | Bertagnoli |
| 5,571,189 A | 11/1996 | Kuslich |
| 5,571,190 A | 11/1996 | Ulrich et al. |
| 5,575,790 A | 11/1996 | Chen et al. |
| 5,593,409 A | 1/1997 | Michelson |
| 5,601,556 A | 2/1997 | Pisharodi |
| 5,601,572 A | 2/1997 | Middleman et al. |
| 5,632,746 A | 5/1997 | Middleman et al. |
| 5,645,597 A | 7/1997 | Krapiva |
| 5,665,122 A | 9/1997 | Kambin |
| 5,669,926 A | 9/1997 | Aust et al. |
| 5,674,295 A | 10/1997 | Ray et al. |
| 5,681,263 A | 10/1997 | Flesch |
| 5,693,100 A | 12/1997 | Pisharodi |
| 5,695,513 A | 12/1997 | Johnson et al. |
| 5,700,239 A | 12/1997 | Yoon |
| 5,702,453 A | 12/1997 | Rabbe et al. |
| 5,702,454 A | 12/1997 | Baumgartner |
| 5,716,416 A | 2/1998 | Lin |
| 5,741,253 A | 4/1998 | Michelson |
| 5,749,879 A | 5/1998 | Middleman et al. |
| 5,755,797 A | 5/1998 | Baumgartner |
| 5,756,127 A | 5/1998 | Gilsonl et al. |
| 5,772,661 A | 6/1998 | Michelson |
| 5,782,832 A | 7/1998 | Larsen et al. |
| 5,788,703 A | 8/1998 | Mittelmeier et al. |
| 5,807,275 A | 9/1998 | Jamshidi |
| 5,820,628 A | 10/1998 | Middleman et al. |
| 5,824,093 A | 10/1998 | Ray et al. |
| 5,827,289 A | 10/1998 | Reiley et al. |
| 5,836,948 A | 11/1998 | Zucherman et al. |
| 5,848,986 A | 12/1998 | Lundquist et al. |
| 5,851,212 A | 12/1998 | Zirps et al. |
| 5,860,977 A | 1/1999 | Zucherman et al. |
| 5,865,848 A | 2/1999 | Baker |
| 5,904,690 A | 5/1999 | Middleman et al. |
| 5,919,236 A | 7/1999 | Husson et al. |
| 5,925,074 A | 7/1999 | Gingras et al. |
| 5,961,554 A | 10/1999 | Janson et al. |
| 5,972,016 A | 10/1999 | Scribner et al. |
| 5,976,186 A | 11/1999 | Bao et al. |
| 5,980,522 A | 11/1999 | Koros et al. |
| 6,012,494 A | 1/2000 | Balazs |
| 6,015,436 A | 1/2000 | Schonhoffer |
| 6,019,793 A | 2/2000 | Perren et al. |
| 6,030,401 A | 2/2000 | Marino |
| 6,033,406 A | 3/2000 | Mathews |
| 6,033,412 A | 3/2000 | Losken et al. |
| 6,039,740 A | 3/2000 | Olerud |
| 6,039,761 A | 3/2000 | Li et al. |
| 6,045,552 A | 4/2000 | Zucherman et al. |
| 6,048,342 A | 4/2000 | Zucherman et al. |
| 6,048,346 A | 4/2000 | Reiley et al. |
| 6,048,360 A | 4/2000 | Khosravl et al. |
| 6,068,630 A | 5/2000 | Zucherman et al. |
| 6,066,154 A | 6/2000 | Reiley et al. |
| 6,073,061 A | 6/2000 | Sharkey et al. |
| 6,083,225 A | 7/2000 | Winslow et al. |
| 6,090,143 A | 7/2000 | Meriwether et al. |
| 6,102,950 A | 8/2000 | Vaccaro |
| 6,110,210 A | 8/2000 | Norton et al. |
| 6,113,640 A | 9/2000 | Tormala et al. |
| 6,119,044 A | 9/2000 | Kuzma |
| 6,123,705 A | 9/2000 | Michelson |
| 6,126,660 A | 10/2000 | Dietz |
| 6,127,597 A | 10/2000 | Beyar et al. |
| 6,159,211 A | 12/2000 | Boriani et al. |
| 6,159,244 A | 12/2000 | Suddaby |
| 6,165,218 A | 12/2000 | Husson et al. |
| 6,174,337 B1 | 1/2001 | Keenan |
| 6,179,873 B1 | 1/2001 | Zientek |
| 6,187,048 B1 | 2/2001 | Millner et al. |
| 6,190,414 B1 | 2/2001 | Young et al. |
| 6,193,757 B1 | 2/2001 | Foley et al. |
| 6,197,033 B1 | 3/2001 | Hald, Jr. et al. |
| D439,980 S | 4/2001 | Reiley et al. |
| 6,217,579 B1 | 4/2001 | Koros |
| 6,221,082 B1 | 4/2001 | Marino et al. |
| 6,224,603 B1 | 5/2001 | Marino |
| 6,235,030 B1 | 5/2001 | Zucherman et al. |
| 6,238,491 B1 | 5/2001 | Davidson et al. |
| 6,235,043 B1 | 6/2001 | Reiley et al. |
| 6,241,734 B1 | 6/2001 | Scribner et al. |
| 6,248,110 B1 | 6/2001 | Reiley et al. |
| 6,251,140 B1 | 6/2001 | Marino et al. |
| 6,261,289 B1 | 7/2001 | Levy |
| 6,264,695 B1 | 7/2001 | Stoy |
| 6,267,763 B1 | 7/2001 | Castro |
| 6,280,456 B1 | 8/2001 | Scribner et al. |
| 6,280,475 B1 | 8/2001 | Bao et al. |
| 6,290,724 B1 | 9/2001 | Marino |
| D449,691 S | 10/2001 | Reiley et al. |
| 6,296,647 B1 | 10/2001 | Robloneck et al. |
| 6,312,443 B1 | 11/2001 | Stone |
| 6,364,828 B1 | 4/2002 | Yeung et al. |
| 6,368,325 B1 | 4/2002 | McKinley et al. |
| 6,387,130 B1 | 6/2002 | Stone et al. |
| 6,402,750 B1 | 6/2002 | Atkinson et al. |
| 6,419,641 B1 | 7/2002 | Mark et al. |
| 6,419,705 B1 | 7/2002 | Erickson |
| 6,423,071 B1 | 7/2002 | Lawson |
| 6,423,083 B2 | 7/2002 | Reiley et al. |
| 6,423,089 B1 | 7/2002 | Gingras et al. |
| 6,425,887 B1 | 7/2002 | McGuckin et al. |
| 6,425,919 B1 | 7/2002 | Lambrecht |
| 6,428,541 B1 | 8/2002 | Boyd et al. |
| 6,436,140 B1 | 8/2002 | Liu et al. |
| 6,440,138 B1 | 8/2002 | Reiley et al. |
| 6,451,019 B1 | 9/2002 | Zucherman et al. |
| 6,468,279 B1 | 10/2002 | Reo |
| 6,478,805 B1 | 11/2002 | Marino et al. |
| 6,482,235 B1 | 11/2002 | Lambrecht et al. |
| 6,485,518 B1 | 11/2002 | Cornwall et al. |
| D467,657 S | 12/2002 | Scribner |
| 6,488,710 B2 | 12/2002 | Besselink |
| 6,491,626 B1 | 12/2002 | Slone et al. |
| 6,491,695 B1 | 12/2002 | Roggenbuck |
| 6,498,421 B1 | 12/2002 | Oh et al. |
| 6,500,178 B2 | 12/2002 | Zucherman et al. |
| 6,500,205 B1 | 12/2002 | Michelson |
| 6,508,839 B1 | 1/2003 | Lambrecht et al. |
| 6,511,471 B2 | 1/2003 | Rosenman et al. |
| 6,512,958 B1 | 1/2003 | Swoyer et al. |
| D469,871 S | 2/2003 | Sand |
| 6,520,991 B2 | 2/2003 | Huene |
| D472,323 S | 3/2003 | Sand |
| 6,530,930 B1 | 3/2003 | Marino et al. |
| 6,533,791 B1 | 3/2003 | Betz et al. |
| 6,533,797 B1 | 3/2003 | Stone et al. |
| 6,540,747 B1 | 4/2003 | Marino |
| 6,554,833 B2 * | 4/2003 | Levy .................. A61B 17/7258 606/62 |
| 6,558,390 B2 | 5/2003 | Cragg |
| 6,562,074 B2 | 5/2003 | Gerbec et al. |
| 6,575,919 B1 | 6/2003 | Reiley et al. |
| 6,575,979 B1 | 6/2003 | Cragg |
| 6,576,016 B1 | 6/2003 | Hochshuler et al. |
| 6,579,291 B1 | 6/2003 | Keith et al. |
| 6,582,431 B1 | 6/2003 | Ray |
| 6,582,433 B2 | 6/2003 | Yun |
| 6,595,998 B2 | 7/2003 | Johnson et al. |
| 6,602,293 B1 | 8/2003 | Biermann et al. |
| 6,607,530 B1 | 8/2003 | Carl et al. |
| 6,607,544 B1 | 8/2003 | Boucher et al. |
| 6,610,094 B2 | 8/2003 | Husson |
| 6,613,054 B2 | 9/2003 | Scribner et al. |
| 6,620,196 B1 | 9/2003 | Trieu |
| 6,623,505 B2 | 9/2003 | Scribner et al. |
| D482,787 S | 11/2003 | Reiss |
| 6,641,587 B2 | 11/2003 | Scribner et al. |
| 6,645,213 B2 | 11/2003 | Sand et al. |

(56) References Cited

U.S. PATENT DOCUMENTS

| | | |
|---|---|---|
| 6,648,917 B2 | 11/2003 | Gerbec et al. |
| D483,495 S | 12/2003 | Sand |
| 6,656,178 B1 | 12/2003 | Veldhulzen et al. |
| 6,656,180 B2 | 12/2003 | Stahurski |
| 6,660,037 B1 | 12/2003 | Husson et al. |
| 6,663,647 B2 | 12/2003 | Reiley et al. |
| 6,666,890 B2 | 12/2003 | Michelson |
| 6,666,891 B2 | 12/2003 | Boehm, Jr. et al. |
| 6,676,663 B2 | 1/2004 | Higueras et al. |
| 6,676,665 B2 | 1/2004 | Foley et al. |
| 6,682,561 B2 | 1/2004 | Songer et al. |
| 6,685,742 B1 | 2/2004 | Jackson |
| 6,689,125 B1 | 2/2004 | Keith et al. |
| 6,689,168 B2 | 2/2004 | Lieberman |
| 6,692,563 B2 | 2/2004 | Zimmermann |
| 6,706,070 B1 | 3/2004 | Wagner et al. |
| 6,716,216 B1 | 4/2004 | Boucher et al. |
| 6,716,247 B2 | 4/2004 | Michelson |
| 6,716,957 B2 | 4/2004 | Tuno |
| 6,719,761 B1 | 4/2004 | Reiley et al. |
| 6,719,773 B1 | 4/2004 | Boucher et al. |
| 6,723,128 B2 | 4/2004 | Uk |
| 6,726,691 B2 | 4/2004 | Osorio et al. |
| D490,159 S | 5/2004 | Sand |
| 6,740,093 B2 | 5/2004 | Hochschuler et al. |
| D492,032 S | 6/2004 | Muller et al. |
| 6,749,560 B1 | 6/2004 | Konstorum et al. |
| 6,755,841 B2 | 6/2004 | Fraser et al. |
| D492,775 S | 7/2004 | Doelling et al. |
| D493,533 S | 7/2004 | Blain |
| 6,758,673 B2 | 7/2004 | Fromovich et al. |
| 6,764,514 B1 | 7/2004 | Li et al. |
| D495,417 S | 8/2004 | Doelling et al. |
| 6,773,460 B2 | 8/2004 | Jackson |
| 6,780,151 B2 | 8/2004 | Grabover et al. |
| 6,783,530 B1 | 8/2004 | Levy |
| 6,793,679 B2 | 9/2004 | Michelson |
| 6,796,983 B1 | 9/2004 | Zucherman et al. |
| 6,805,695 B2 | 10/2004 | Keith et al. |
| 6,805,697 B1 | 10/2004 | Helm et al. |
| 6,808,537 B2 | 10/2004 | Michelson |
| 6,814,736 B2 | 11/2004 | Reiley et al. |
| 6,814,756 B1 | 11/2004 | Michelson |
| 6,821,298 B1 | 11/2004 | Jackson |
| 6,823,979 B2 | 11/2004 | Konieczny |
| 6,830,589 B2 | 12/2004 | Erickson |
| 6,835,205 B2 | 12/2004 | Atkinson et al. |
| 6,835,206 B2 | 12/2004 | Jackson |
| 6,840,944 B2 | 1/2005 | Suddaby |
| 6,852,126 B2 | 2/2005 | Ahlgren |
| 6,852,129 B2 | 2/2005 | Gerbec et al. |
| 6,863,668 B2 | 3/2005 | Gillespie et al. |
| 6,863,672 B2 | 3/2005 | Reiley et al. |
| 6,863,673 B2 | 3/2005 | Gerbec et al. |
| 6,866,682 B1 | 3/2005 | An et al. |
| 6,881,228 B2 | 4/2005 | Zdeblick et al. |
| 6,883,520 B2 | 4/2005 | Lambrecht et al. |
| 6,887,248 B2 | 5/2005 | McKinley et al. |
| 6,893,466 B2 | 5/2005 | Trieu |
| 6,899,716 B2 | 5/2005 | Cragg |
| 6,899,719 B2 | 5/2005 | Reiley et al. |
| D506,828 S | 6/2005 | Layne et al. |
| 6,905,512 B2 | 6/2005 | Paes et al. |
| 6,908,506 B2 | 6/2005 | Zimmermann |
| 6,921,403 B2 | 7/2005 | Cragg et al. |
| 6,923,810 B1 | 8/2005 | Michelson |
| 6,923,813 B2 | 8/2005 | Phillips et al. |
| 6,923,814 B1 | 8/2005 | Hildebrand et al. |
| 6,929,647 B2 | 8/2005 | Cohen |
| 6,945,973 B2 | 9/2005 | Bray |
| 6,952,129 B2 | 10/2005 | Lin et al. |
| 6,962,606 B2 | 11/2005 | Michelson |
| 6,964,674 B1 | 11/2005 | Matsuura et al. |
| D512,506 S | 12/2005 | Layne et al. |
| 6,972,035 B2 | 12/2005 | Michelson |
| 6,974,479 B2 | 12/2005 | Trieu |
| 6,979,341 B2 | 12/2005 | Scribner et al. |
| 6,981,981 B2 | 1/2006 | Reiley et al. |
| 6,997,929 B2 | 2/2006 | Manzi et al. |
| 7,004,945 B2 | 2/2006 | Boyd et al. |
| 7,008,453 B1 | 3/2006 | Michelson |
| 7,014,633 B2 | 3/2006 | Cragg |
| 7,018,089 B2 | 3/2006 | Wenz et al. |
| 7,018,415 B1 | 3/2006 | McKay |
| 7,018,453 B2 | 3/2006 | Klein et al. |
| 7,029,498 B2 | 4/2006 | Boehm et al. |
| 7,044,954 B2 | 5/2006 | Reiley et al. |
| 7,048,694 B2 | 5/2006 | Mark et al. |
| 7,063,703 B2 | 6/2006 | Reo |
| 7,066,961 B2 | 6/2006 | Michelson |
| 7,069,087 B2 | 6/2006 | Sharkey et al. |
| 7,070,598 B2 | 7/2006 | Lim et al. |
| 7,074,226 B2 | 7/2006 | Roehm, III et al. |
| 7,081,120 B2 | 7/2006 | Li et al. |
| 7,081,122 B1 | 7/2006 | Reiley et al. |
| 7,087,055 B2 | 8/2006 | Lim et al. |
| 7,094,257 B2 | 8/2006 | Mujwid et al. |
| 7,115,128 B2 | 10/2006 | Michelson |
| 7,115,163 B2 | 10/2006 | Zimmermann |
| 7,118,579 B2 | 10/2006 | Michelson |
| 7,118,580 B1 | 10/2006 | Beyersdorff et al. |
| 7,118,598 B2 | 10/2006 | Michelson |
| 7,124,761 B2 | 10/2006 | Lambrecht et al. |
| 7,128,760 B2 | 10/2006 | Michelson |
| 7,135,424 B2 | 11/2006 | Worley et al. |
| 7,153,304 B2 | 12/2006 | Robie et al. |
| 7,153,305 B2 | 12/2006 | Johnson et al. |
| 7,153,306 B2 | 12/2006 | Ralph et al. |
| 7,153,307 B2 | 12/2006 | Scribner et al. |
| 7,156,874 B2 | 1/2007 | Paponneau et al. |
| 7,156,875 B2 | 1/2007 | Michelson |
| 7,166,107 B2 | 1/2007 | Anderson |
| 7,179,293 B2 | 2/2007 | McKay |
| 7,189,242 B2 | 3/2007 | Boyd et al. |
| 7,204,851 B2 | 4/2007 | Trieu et al. |
| 7,207,991 B2 | 4/2007 | Michelson |
| 7,211,112 B2 | 5/2007 | Baynham et al. |
| 7,214,227 B2 | 5/2007 | Colleran et al. |
| 7,220,281 B2 | 5/2007 | Lambrecht et al. |
| 7,223,227 B2 | 5/2007 | Pflueger |
| 7,226,481 B2 | 6/2007 | Kuslich |
| 7,241,297 B2 | 7/2007 | Shaolian et al. |
| 7,244,273 B2 | 7/2007 | Pedersen et al. |
| 7,250,060 B2 | 7/2007 | Trieu |
| 7,252,671 B2 | 8/2007 | Scribner et al. |
| 7,252,686 B2 | 8/2007 | Carrison |
| 7,267,687 B2 | 9/2007 | McGuckin, Jr. |
| 7,270,679 B2 | 9/2007 | Istephanous et al. |
| 7,276,062 B2 | 10/2007 | McDaniel et al. |
| 7,311,713 B2 | 12/2007 | Johnson et al. |
| 7,316,714 B2 | 1/2008 | Gordon et al. |
| 7,318,840 B2 | 1/2008 | McKay |
| 7,320,689 B2 | 1/2008 | Keller |
| 7,322,962 B2 | 1/2008 | Forrest |
| 7,383,639 B2 | 6/2008 | Malandaln |
| 7,485,134 B2 | 2/2009 | Simonson |
| 7,608,083 B2 | 10/2009 | Lee et al. |
| 7,618,458 B2 | 11/2009 | Biedermann |
| 7,637,905 B2 | 12/2009 | Saadat et al. |
| 7,753,912 B2 | 7/2010 | Raymond |
| 7,758,647 B2 | 7/2010 | Arnin |
| 7,828,807 B2 | 11/2010 | LeHeuo et al. |
| 7,901,460 B2 | 3/2011 | Sherman |
| 7,922,767 B2 | 4/2011 | Sack |
| 8,021,429 B2 | 9/2011 | Viker |
| 8,025,697 B2 | 9/2011 | McClellan |
| 8,137,401 B2 | 3/2012 | Stad |
| 8,142,507 B2 | 3/2012 | McGuckin |
| 8,187,327 B2 | 5/2012 | Edidin et al. |
| 8,252,054 B2 | 8/2012 | Greenhalgh |
| 8,579,980 B2 | 11/2013 | DeLurio |
| 8,632,591 B2 | 1/2014 | Vila |
| 8,663,332 B1 | 3/2014 | To |
| 8,764,806 B2 | 7/2014 | Abdou |

(56) References Cited

U.S. PATENT DOCUMENTS

| | | |
|---|---|---|
| 2001/0011174 A1 | 8/2001 | Reiley et al. |
| 2001/0016741 A1 | 8/2001 | Burkus et al. |
| 2002/0016583 A1 | 2/2002 | Cragg |
| 2002/0026195 A1 | 2/2002 | Layne et al. |
| 2002/0026244 A1 | 2/2002 | Trieu |
| 2002/0045942 A1 | 4/2002 | Ham |
| 2002/0068974 A1 | 6/2002 | Kuslich et al. |
| 2002/0077700 A1 | 6/2002 | Varga et al. |
| 2002/0082584 A1 | 6/2002 | Rosenman et al. |
| 2002/0082608 A1 | 6/2002 | Reiley et al. |
| 2002/0087163 A1 | 7/2002 | Dixon et al. |
| 2002/0091390 A1 | 7/2002 | Michelson |
| 2002/0099385 A1 | 7/2002 | Ralph et al. |
| 2002/0107519 A1 | 8/2002 | Dixon et al. |
| 2002/0107573 A1 | 8/2002 | Steinberg |
| 2002/0156482 A1 | 10/2002 | Scribner et al. |
| 2002/0169471 A1 | 11/2002 | Ferdinand |
| 2002/0172851 A1 | 11/2002 | Corey et al. |
| 2002/0173796 A1 | 11/2002 | Cragg |
| 2002/0173841 A1 | 11/2002 | Ortiz et al. |
| 2002/0173851 A1 | 11/2002 | McKay |
| 2002/0183761 A1 | 12/2002 | Johnson et al. |
| 2002/0183778 A1 | 12/2002 | Reiley et al. |
| 2002/0191487 A1 | 12/2002 | Sand |
| 2003/0018390 A1 | 1/2003 | Husson |
| 2003/0032963 A1 | 2/2003 | Reiss et al. |
| 2003/0050644 A1 | 3/2003 | Boucher et al. |
| 2003/0069593 A1 | 4/2003 | Tremulls et al. |
| 2003/0074075 A1 | 4/2003 | Thomas et al. |
| 2003/0108588 A1 | 6/2003 | Chen et al. |
| 2003/0130664 A1 | 7/2003 | Boucher et al. |
| 2003/0171812 A1 | 9/2003 | Grunberg et al. |
| 2003/0191414 A1 | 10/2003 | Reiley et al. |
| 2003/0191489 A1 | 10/2003 | Reiley et al. |
| 2003/0195518 A1 | 10/2003 | Cragg |
| 2003/0195547 A1 | 10/2003 | Scribner et al. |
| 2003/0195630 A1 | 10/2003 | Ferree |
| 2003/0199979 A1 | 10/2003 | McGuckin, Jr. |
| 2003/0208136 A1 | 11/2003 | Mark et al. |
| 2003/0220648 A1 | 11/2003 | Osorio et al. |
| 2003/0220695 A1 | 11/2003 | Sevrain |
| 2003/0229372 A1 | 12/2003 | Reiley et al. |
| 2003/0233096 A1 | 12/2003 | Osorio et al. |
| 2004/0002762 A1* | 1/2004 | Hawkins ............ A61F 2/4425 623/17.15 |
| 2004/0010251 A1 | 1/2004 | Pitaru et al. |
| 2004/0010260 A1 | 1/2004 | Scribner et al. |
| 2004/0010263 A1 | 1/2004 | Boucher et al. |
| 2004/0019354 A1 | 1/2004 | Johnson et al. |
| 2004/0024408 A1 | 2/2004 | Burkus et al. |
| 2004/0024409 A1 | 2/2004 | Sand et al. |
| 2004/0024463 A1 | 2/2004 | Thomas, Jr. et al. |
| 2004/0024465 A1 | 2/2004 | Lambrecht et al. |
| 2004/0034343 A1 | 2/2004 | Gillespie et al. |
| 2004/0034429 A1 | 2/2004 | Lambrecht et al. |
| 2004/0049203 A1 | 3/2004 | Scribner et al. |
| 2004/0059333 A1 | 3/2004 | Carl et al. |
| 2004/0059339 A1 | 3/2004 | Roehm, III et al. |
| 2004/0059418 A1 | 3/2004 | McKay et al. |
| 2004/0064144 A1 | 4/2004 | Johnson et al. |
| 2004/0073308 A1 | 4/2004 | Kuslich et al. |
| 2004/0082953 A1 | 4/2004 | Petit |
| 2004/0087947 A1 | 5/2004 | Lim et al. |
| 2004/0092933 A1 | 5/2004 | Shaolian et al. |
| 2004/0092948 A1 | 5/2004 | Stevens et al. |
| 2004/0092988 A1 | 5/2004 | Shaolian et al. |
| 2004/0097924 A1 | 5/2004 | Lambrecht et al. |
| 2004/0097930 A1 | 5/2004 | Justis et al. |
| 2004/0097932 A1 | 5/2004 | Ray, III et al. |
| 2004/0098131 A1 | 5/2004 | Bryan et al. |
| 2004/0102774 A1 | 5/2004 | Trieu |
| 2004/0106940 A1 | 6/2004 | Shaolian et al. |
| 2004/0111161 A1 | 6/2004 | Trieu |
| 2004/0117019 A1 | 6/2004 | Trieu et al. |
| 2004/0133124 A1 | 7/2004 | Bates et al. |
| 2004/0133229 A1 | 7/2004 | Lambrecht et al. |
| 2004/0133280 A1 | 7/2004 | Trieu |
| 2004/0138748 A1 | 7/2004 | Boyer, II et al. |
| 2004/0153064 A1 | 8/2004 | Foley et al. |
| 2004/0153115 A1 | 8/2004 | Reiley et al. |
| 2004/0158206 A1 | 8/2004 | Aboul-Hosn et al. |
| 2004/0167561 A1 | 8/2004 | Boucher et al. |
| 2004/0167562 A1 | 8/2004 | Osorio et al. |
| 2004/0167625 A1 | 8/2004 | Beyar et al. |
| 2004/0176775 A1 | 9/2004 | Burkus et al. |
| 2004/0186471 A1 | 9/2004 | Trieu |
| 2004/0186528 A1 | 9/2004 | Ries et al. |
| 2004/0186573 A1 | 9/2004 | Ferree |
| 2004/0210231 A1 | 10/2004 | Boucher et al. |
| 2004/0210310 A1 | 10/2004 | Trieu |
| 2004/0215344 A1 | 10/2004 | Hochschuler et al. |
| 2004/0220580 A1 | 11/2004 | Johnson et al. |
| 2004/0220672 A1 | 11/2004 | Shadduck |
| 2004/0225296 A1 | 11/2004 | Reiss et al. |
| 2004/0225361 A1 | 11/2004 | Glenn et al. |
| 2004/0230191 A1 | 11/2004 | Frey et al. |
| 2004/0230309 A1 | 11/2004 | DiMauro et al. |
| 2004/0243229 A1 | 12/2004 | Vidlund et al. |
| 2004/0249377 A1 | 12/2004 | Kaes et al. |
| 2004/0254520 A1 | 12/2004 | Porteous et al. |
| 2004/0254644 A1 | 12/2004 | Taylor |
| 2004/0260300 A1 | 12/2004 | Gorensek et al. |
| 2004/0260397 A1 | 12/2004 | Lambrecht et al. |
| 2004/0267271 A9 | 12/2004 | Scribner et al. |
| 2005/0004578 A1 | 1/2005 | Lambrecht et al. |
| 2005/0010293 A1 | 1/2005 | Zucherman et al. |
| 2005/0010298 A1 | 1/2005 | Zucherman et al. |
| 2005/0015148 A1 | 1/2005 | Jansen et al. |
| 2005/0015152 A1 | 1/2005 | Sweeney |
| 2005/0021041 A1 | 1/2005 | Michelson |
| 2005/0033295 A1 | 2/2005 | Wisnewski |
| 2005/0033440 A1 | 2/2005 | Lambrecht et al. |
| 2005/0038517 A1 | 2/2005 | Carrison et al. |
| 2005/0043737 A1 | 2/2005 | Reiley et al. |
| 2005/0043796 A1 | 2/2005 | Grant et al. |
| 2005/0055097 A1 | 3/2005 | Grunberg et al. |
| 2005/0060036 A1 | 3/2005 | Schultz et al. |
| 2005/0060038 A1 | 3/2005 | Lambrecht et al. |
| 2005/0065519 A1 | 3/2005 | Michelson |
| 2005/0065609 A1 | 3/2005 | Wardlaw |
| 2005/0069571 A1 | 3/2005 | Slivka et al. |
| 2005/0070908 A1 | 3/2005 | Cragg |
| 2005/0070911 A1 | 3/2005 | Carrison |
| 2005/0070913 A1 | 3/2005 | Milbocker et al. |
| 2005/0071011 A1 | 3/2005 | Ralph et al. |
| 2005/0080488 A1 | 4/2005 | Schultz |
| 2005/0085912 A1 | 4/2005 | Amin et al. |
| 2005/0090833 A1 | 4/2005 | DiPoto |
| 2005/0090852 A1 | 4/2005 | Layne et al. |
| 2005/0090899 A1 | 4/2005 | DiPoto |
| 2005/0107878 A1 | 5/2005 | Conchy |
| 2005/0107880 A1 | 5/2005 | Shimp et al. |
| 2005/0113918 A1 | 5/2005 | Messeril et al. |
| 2005/0113919 A1 | 5/2005 | Cragg et al. |
| 2005/0113928 A1 | 5/2005 | Cragg et al. |
| 2005/0118228 A1 | 6/2005 | Trieu |
| 2005/0119662 A1 | 6/2005 | Reiley et al. |
| 2005/0119750 A1 | 6/2005 | Studer |
| 2005/0119751 A1 | 6/2005 | Lawson |
| 2005/0119752 A1 | 6/2005 | Williams et al. |
| 2005/0119754 A1 | 6/2005 | Trieu et al. |
| 2005/0124989 A1 | 6/2005 | Suddaby |
| 2005/0124992 A1 | 6/2005 | Ferree |
| 2005/0124999 A1 | 6/2005 | Teitelbaum et al. |
| 2005/0125066 A1 | 6/2005 | McAfee |
| 2005/0131267 A1 | 6/2005 | Talmadge |
| 2005/0131268 A1 | 6/2005 | Talmadge |
| 2005/0131269 A1 | 6/2005 | Talmadge |
| 2005/0131536 A1 | 6/2005 | Eisermann et al. |
| 2005/0131540 A1 | 6/2005 | Trieu |
| 2005/0131541 A1 | 6/2005 | Trieu |
| 2005/0137602 A1 | 6/2005 | Assell et al. |
| 2005/0142211 A1 | 6/2005 | Wenz |
| 2005/0143763 A1 | 6/2005 | Ortiz et al. |

(56) References Cited

U.S. PATENT DOCUMENTS

| | | |
|---|---|---|
| 2005/0143827 A1 | 6/2005 | Globerman et al. |
| 2005/0149022 A1 | 7/2005 | Shaolian et al. |
| 2005/0149191 A1 | 7/2005 | Cragg et al. |
| 2005/0149194 A1 | 7/2005 | Ahlgren |
| 2005/0149197 A1 | 7/2005 | Cauthen |
| 2005/0154396 A1 | 7/2005 | Foley et al. |
| 2005/0154463 A1 | 7/2005 | Trieu |
| 2005/0165406 A1 | 7/2005 | Assell et al. |
| 2005/0171539 A1 | 8/2005 | Braun et al. |
| 2005/0171552 A1 | 8/2005 | Johnson et al. |
| 2005/0182412 A1 | 8/2005 | Johnson et al. |
| 2005/0182413 A1 | 8/2005 | Johnson et al. |
| 2005/0182414 A1 | 8/2005 | Manzi et al. |
| 2005/0187556 A1 | 8/2005 | Stack et al. |
| 2005/0187558 A1 | 8/2005 | Johnson et al. |
| 2005/0187559 A1 | 8/2005 | Raymond et al. |
| 2005/0187564 A1 | 8/2005 | Jayaraman |
| 2005/0197707 A1 | 9/2005 | Trieu et al. |
| 2005/0216018 A1 | 9/2005 | Sennett |
| 2005/0216087 A1 | 9/2005 | Zucherman et al. |
| 2005/0222684 A1 | 10/2005 | Ferree |
| 2005/0228383 A1 | 10/2005 | Zucherman et al. |
| 2005/0228391 A1* | 10/2005 | Levy ............... A61B 17/8858 606/86 R |
| 2005/0228397 A1 | 10/2005 | Malandain et al. |
| 2005/0234425 A1 | 10/2005 | Miller et al. |
| 2005/0234451 A1 | 10/2005 | Markworth |
| 2005/0234452 A1 | 10/2005 | Malandain |
| 2005/0234456 A1 | 10/2005 | Malandain |
| 2005/0240182 A1 | 10/2005 | Zucherman et al. |
| 2005/0240189 A1 | 10/2005 | Rousseau et al. |
| 2005/0240193 A1 | 10/2005 | Layne et al. |
| 2005/0240269 A1 | 10/2005 | Lambrecht et al. |
| 2005/0251149 A1 | 11/2005 | Wenz |
| 2005/0251260 A1 | 11/2005 | Gerber et al. |
| 2005/0261684 A1 | 11/2005 | Shaolian et al. |
| 2005/0261695 A1 | 11/2005 | Cragg et al. |
| 2005/0261781 A1 | 11/2005 | Sennett et al. |
| 2005/0273166 A1 | 12/2005 | Sweeney |
| 2005/0273173 A1 | 12/2005 | Gordon et al. |
| 2005/0278023 A1 | 12/2005 | Zwirkoski |
| 2005/0278027 A1 | 12/2005 | Hyde, Jr. |
| 2005/0278029 A1 | 12/2005 | Trieu |
| 2005/0283244 A1 | 12/2005 | Gordon et al. |
| 2005/0287071 A1 | 12/2005 | Wenz |
| 2006/0004456 A1 | 1/2006 | McKay |
| 2006/0009779 A1 | 1/2006 | Collins et al. |
| 2006/0030850 A1 | 2/2006 | Keegan et al. |
| 2006/0030933 A1 | 2/2006 | DeLegge |
| 2006/0030943 A1 | 2/2006 | Peterman |
| 2006/0036241 A1 | 2/2006 | Siegal |
| 2006/0036259 A1 | 2/2006 | Carl et al. |
| 2006/0036261 A1 | 2/2006 | McDonnell |
| 2006/0036273 A1 | 2/2006 | Siegal |
| 2006/0041258 A1 | 2/2006 | Galea |
| 2006/0058807 A1 | 3/2006 | Landry et al. |
| 2006/0058880 A1 | 3/2006 | Wysocki et al. |
| 2006/0064171 A1 | 3/2006 | Trieu |
| 2006/0069439 A1 | 3/2006 | Zucherman et al. |
| 2006/0069440 A1 | 3/2006 | Zucherman et al. |
| 2006/0085002 A1 | 4/2006 | Trieu et al. |
| 2006/0085009 A1 | 4/2006 | Truckal et al. |
| 2006/0089642 A1 | 4/2006 | Diaz et al. |
| 2006/0089646 A1 | 4/2006 | Bonutti |
| 2006/0089654 A1 | 4/2006 | Lins et al. |
| 2006/0089716 A1 | 4/2006 | Truckal et al. |
| 2006/0089718 A1 | 4/2006 | Zucherman et al. |
| 2006/0089719 A1 | 4/2006 | Trieu |
| 2006/0095045 A1 | 5/2006 | Trieu |
| 2006/0095046 A1 | 5/2006 | Trieu et al. |
| 2006/0095134 A1 | 5/2006 | Trieu et al. |
| 2006/0095138 A1 | 5/2006 | Truckal et al. |
| 2006/0100706 A1 | 5/2006 | Shadduck et al. |
| 2006/0106397 A1 | 5/2006 | Lins |
| 2006/0106459 A1 | 5/2006 | Truckal et al. |
| 2006/0122704 A1 | 6/2006 | Vresilovic et al. |
| 2006/0129244 A1 | 6/2006 | Ensign |
| 2006/0136064 A1 | 6/2006 | Sherman |
| 2006/0142858 A1 | 6/2006 | Colleran et al. |
| 2006/0142864 A1 | 6/2006 | Cauthen |
| 2006/0149136 A1 | 7/2006 | Seto et al. |
| 2006/0149237 A1 | 7/2006 | Markworth et al. |
| 2006/0149252 A1 | 7/2006 | Markworth et al. |
| 2006/0149379 A1 | 7/2006 | Kuslich et al. |
| 2006/0149380 A1 | 7/2006 | Lotz et al. |
| 2006/0155379 A1 | 7/2006 | Heneveld, Sr. et al. |
| 2006/0161162 A1 | 7/2006 | Lambrecht et al. |
| 2006/0161166 A1 | 7/2006 | Johnson et al. |
| 2006/0167553 A1 | 7/2006 | Cauthen, III et al. |
| 2006/0173545 A1 | 8/2006 | Cauthen, III et al. |
| 2006/0178746 A1 | 8/2006 | Bartish, Jr. et al. |
| 2006/0184192 A1 | 8/2006 | Markworth et al. |
| 2006/0184247 A1 | 8/2006 | Edidin et al. |
| 2006/0184248 A1 | 8/2006 | Edidin et al. |
| 2006/0189999 A1 | 8/2006 | Zwirkoski |
| 2006/0190083 A1 | 8/2006 | Arnin et al. |
| 2006/0190085 A1 | 8/2006 | Cauthen |
| 2006/0195102 A1 | 8/2006 | Malandain |
| 2006/0195191 A1 | 8/2006 | Sweeney, II et al. |
| 2006/0200139 A1 | 9/2006 | Michelson |
| 2006/0200164 A1 | 9/2006 | Michelson |
| 2006/0200239 A1 | 9/2006 | Rothman et al. |
| 2006/0200240 A1 | 9/2006 | Rothman et al. |
| 2006/0200241 A1 | 9/2006 | Rothman et al. |
| 2006/0200242 A1 | 9/2006 | Rothman et al. |
| 2006/0200243 A1 | 9/2006 | Rothman et al. |
| 2006/0206116 A1 | 9/2006 | Yeung |
| 2006/0206207 A1 | 9/2006 | Dryer et al. |
| 2006/0235423 A1 | 10/2006 | Cantu |
| 2006/0235521 A1 | 10/2006 | Zucherman et al. |
| 2006/0241663 A1 | 10/2006 | Rice et al. |
| 2006/0241770 A1 | 10/2006 | Rhoda et al. |
| 2006/0247770 A1 | 11/2006 | Peterman |
| 2006/0247771 A1 | 11/2006 | Peterman et al. |
| 2006/0247781 A1 | 11/2006 | Francis |
| 2006/0264896 A1 | 11/2006 | Palmer |
| 2006/0264939 A1 | 11/2006 | Zucherman et al. |
| 2006/0264945 A1 | 11/2006 | Edidin et al. |
| 2006/0265067 A1 | 11/2006 | Zucherman et al. |
| 2006/0265077 A1 | 11/2006 | Zwirkoski |
| 2006/0271049 A1 | 11/2006 | Zucherman et al. |
| 2006/0271061 A1 | 11/2006 | Beyer et al. |
| 2006/0276897 A1 | 12/2006 | Winslow |
| 2006/0276899 A1 | 12/2006 | Zipnick et al. |
| 2006/0282167 A1 | 12/2006 | Lambrecht et al. |
| 2006/0287726 A1 | 12/2006 | Segal et al. |
| 2006/0287727 A1 | 12/2006 | Segal et al. |
| 2006/0293662 A1 | 12/2006 | Boyer, II et al. |
| 2006/0293753 A1 | 12/2006 | Thramann |
| 2007/0006692 A1 | 1/2007 | Phan |
| 2007/0010716 A1 | 1/2007 | Malandain et al. |
| 2007/0010717 A1 | 1/2007 | Cragg |
| 2007/0010824 A1 | 1/2007 | Malandain et al. |
| 2007/0010844 A1 | 1/2007 | Gong et al. |
| 2007/0010845 A1 | 1/2007 | Gong et al. |
| 2007/0010846 A1 | 1/2007 | Leung et al. |
| 2007/0010848 A1 | 1/2007 | Leung et al. |
| 2007/0010889 A1 | 1/2007 | Francis |
| 2007/0032703 A1 | 2/2007 | Sankaran et al. |
| 2007/0032791 A1 | 2/2007 | Greenhalgh |
| 2007/0043361 A1 | 2/2007 | Malandain et al. |
| 2007/0043362 A1 | 2/2007 | Malandain et al. |
| 2007/0043363 A1 | 2/2007 | Malandain et al. |
| 2007/0048382 A1 | 3/2007 | Meyer et al. |
| 2007/0049849 A1 | 3/2007 | Schwardt et al. |
| 2007/0049934 A1 | 3/2007 | Edidin et al. |
| 2007/0049935 A1 | 3/2007 | Edidin et al. |
| 2007/0050030 A1 | 3/2007 | Kim |
| 2007/0050034 A1 | 3/2007 | Schwardt et al. |
| 2007/0050035 A1 | 3/2007 | Schwardt et al. |
| 2007/0055201 A1 | 3/2007 | Seto et al. |
| 2007/0055237 A1 | 3/2007 | Edidin et al. |
| 2007/0055246 A1 | 3/2007 | Zucherman et al. |
| 2007/0055265 A1 | 3/2007 | Schaller |

(56) References Cited

U.S. PATENT DOCUMENTS

| | | |
|---|---|---|
| 2007/0055266 A1 | 3/2007 | Osorio et al. |
| 2007/0055267 A1 | 3/2007 | Osorio et al. |
| 2007/0055271 A1 | 3/2007 | Schaller |
| 2007/0055272 A1 | 3/2007 | Schaller |
| 2007/0055273 A1 | 3/2007 | Schaller |
| 2007/0055274 A1 | 3/2007 | Appenzeller et al. |
| 2007/0055275 A1 | 3/2007 | Schaller |
| 2007/0055276 A1 | 3/2007 | Edidin |
| 2007/0055277 A1 | 3/2007 | Osorio et al. |
| 2007/0055278 A1 | 3/2007 | Osorio et al. |
| 2007/0055281 A1 | 3/2007 | Osorio et al. |
| 2007/0055284 A1 | 3/2007 | Osorio et al. |
| 2007/0055300 A1 | 3/2007 | Osorio et al. |
| 2007/0060933 A1 | 3/2007 | Sankaran et al. |
| 2007/0060935 A1 | 3/2007 | Schwardt et al. |
| 2007/0067034 A1 | 3/2007 | Chirico et al. |
| 2007/0068329 A1 | 3/2007 | Phan et al. |
| 2007/0073292 A1 | 3/2007 | Kohm et al. |
| 2007/0093689 A1 | 3/2007 | Steinberg |
| 2007/0093906 A1 | 3/2007 | Hudgins et al. |
| 2007/0078436 A1 | 4/2007 | Leung et al. |
| 2007/0078463 A1 | 4/2007 | Malandain |
| 2007/0093899 A1 | 4/2007 | Dutoit et al. |
| 2007/0123986 A1 | 5/2007 | Schaller |
| 2007/0135922 A1 | 6/2007 | Trieu |
| 2007/0149978 A1 | 6/2007 | Shezlfi et al. |
| 2007/0150059 A1 | 6/2007 | Ruberte et al. |
| 2007/0150060 A1 | 6/2007 | Trieu |
| 2007/0150061 A1 | 6/2007 | Trieu |
| 2007/0150063 A1 | 6/2007 | Ruberte et al. |
| 2007/0150064 A1 | 6/2007 | Ruberte et al. |
| 2007/0162127 A1 | 7/2007 | Peterman et al. |
| 2007/0167945 A1 | 7/2007 | Lange et al. |
| 2007/0168038 A1 | 7/2007 | Trieu |
| 2007/0173939 A1 | 7/2007 | Kim et al. |
| 2007/0179612 A1 | 8/2007 | Johnson et al. |
| 2007/0179615 A1 | 8/2007 | Heinz et al. |
| 2007/0179616 A1 | 8/2007 | Braddock, Jr. et al. |
| 2007/0179618 A1 | 8/2007 | Trieu et al. |
| 2007/0185578 A1 | 8/2007 | O'Neil et al. |
| 2007/0191953 A1 | 8/2007 | Trieu |
| 2007/0197935 A1 | 8/2007 | Reiley et al. |
| 2007/0198023 A1 | 8/2007 | Sand et al. |
| 2007/0198025 A1 | 8/2007 | Trieu et al. |
| 2007/0208426 A1 | 9/2007 | Trieu |
| 2007/0213717 A1 | 9/2007 | Trieu et al. |
| 2007/0219634 A1 | 9/2007 | Greenhaigh et al. |
| 2007/0233074 A1 | 10/2007 | Anderson et al. |
| 2007/0260255 A1 | 11/2007 | Haddock et al. |
| 2007/0270957 A1 | 11/2007 | Heinz |
| 2007/0282443 A1 | 12/2007 | Globerman et al. |
| 2008/0021557 A1 | 1/2008 | Trieu |
| 2008/0027437 A1 | 1/2008 | Johnson et al. |
| 2008/0027453 A1 | 1/2008 | Johnson et al. |
| 2008/0027454 A1 | 1/2008 | Johnson et al. |
| 2008/0051897 A1 | 2/2008 | Lopez et al. |
| 2008/0071356 A1 | 3/2008 | Greenhaigh et al. |
| 2008/0097611 A1 | 4/2008 | Mastrorio et al. |
| 2008/0125865 A1 | 5/2008 | Abdelgany |
| 2008/0140207 A1 | 6/2008 | Olmos et al. |
| 2008/0167657 A1 | 7/2008 | Greenhaigh |
| 2008/0177306 A1 | 7/2008 | Lemborne et al. |
| 2008/0195210 A1 | 8/2008 | Miljasevlo et al. |
| 2008/0221687 A1 | 9/2008 | Viker |
| 2008/0229597 A1 | 9/2008 | Malandaln |
| 2008/0243261 A1 | 10/2008 | Stad et al. |
| 2008/0249628 A1 | 10/2008 | Altarac |
| 2008/0281346 A1 | 11/2008 | Greenhaigh et al. |
| 2008/0281364 A1 | 11/2008 | Chirico et al. |
| 2009/0018524 A1 | 1/2009 | Greenhaigh et al. |
| 2009/0030423 A1 | 1/2009 | Puno |
| 2009/0048678 A1 | 2/2009 | Saal et al. |
| 2011/0208306 A1 | 8/2011 | Farris |
| 2011/0245926 A1 | 10/2011 | Kitchen |
| 2012/0071980 A1 | 3/2012 | Purcell |
| 2013/0204374 A1 | 8/2013 | Milella |
| 2014/0058513 A1 | 2/2014 | Gahman |
| 2014/0067073 A1 | 3/2014 | Hauck |
| 2014/0236296 A1 | 8/2014 | Wagner |

FOREIGN PATENT DOCUMENTS

| | | |
|---|---|---|
| EP | 0529275 A2 | 3/1993 |
| EP | 0 621 020 A1 | 10/1994 |
| EP | 0743045 | 11/1996 |
| EP | 1 157 676 A1 | 4/2001 |
| FR | 2712486 A1 | 5/1995 |
| FR | 2 913 331 | 12/2008 |
| JP | 20020028171 | 5/2001 |
| WO | WO 91/04634 | 3/1993 |
| WO | WO98/034552 A1 | 8/1998 |
| WO | WO 00/67650 | 11/2000 |
| WO | WO 00/67651 | 11/2000 |
| WO | WO 01/10316 A1 | 2/2001 |
| WO | WO 02/17824 A2 | 3/2002 |
| WO | WO 02/30338 A1 | 4/2002 |
| WO | WO 02/43628 A1 | 6/2002 |
| WO | WO 02/47563 A1 | 6/2002 |
| WO | WO 02/071921 A2 | 9/2002 |
| WO | WO 03/007854 A1 | 1/2003 |
| WO | WO 03/020169 A2 | 3/2003 |
| WO | WO 03/022165 A1 | 3/2003 |
| WO | WO 03/028587 A2 | 4/2003 |
| WO | WO 03/059180 A2 | 7/2003 |
| WO | WO 03/101308 A1 | 12/2003 |
| WO | WO2004/034924 A2 | 4/2004 |
| WO | WO2004/062505 A1 | 7/2004 |
| WO | WO 2004/082526 A2 | 9/2004 |
| WO | WO 2004/098420 A2 | 11/2004 |
| WO | WO 2004/108022 A1 | 12/2004 |
| WO | WO 2005/032433 A2 | 4/2005 |
| WO | WO 2005/048856 | 6/2005 |
| WO | WO 2005/051246 A2 | 6/2005 |
| WO | WO 2005/081877 A2 | 9/2005 |
| WO | WO2006/047587 A2 | 5/2006 |
| WO | WO 2006/047645 A2 | 5/2006 |
| WO | WO 2006/060420 A1 | 6/2006 |
| WO | WO 2006/066228 A2 | 6/2006 |
| WO | WO2006/072941 A2 | 7/2006 |
| WO | WO 2007/022194 | 2/2007 |
| WO | WO2007/067726 A2 | 6/2007 |
| WO | WO 2010/008353 | 1/2010 |
| WO | WO 2013/043850 | 3/2013 |

OTHER PUBLICATIONS

Office Action for Japanese Patent Application No. 2009-551011 dated Sep. 18, 2012.

Edeland, H.G., "Some Additional Suggestions for an Intervertebral Disc Prosthesis", J of BioMedical Engr., vol. 7(1) pp. 57-62, Jan. 1985.

U.S. Appl. No. 60/557,246, filed Mar. 29, 2004 entitled: Device and Methods to Reduce and Stabilize Broken Bones.

Office Action from U.S. Appl. No. 11/464,807 dated Dec. 22, 2010, 9 pages.

USPTO Office Action dated Apr. 1, 2010 for U.S. Appl. No. 11/464,807.

USPTO Notice of Allowance and Fee(s) Due dated Dec. 23, 2009 for U.S. Appl. No. 11/464,790.

USPTO Supplemental Notice of Allowability dated Dec. 31, 2009 for U.S. Appl. No. 11/464,790.

USPTO Notice of Allowance and Fee(s) Due dated Dec. 23, 2009 for U.S. Appl. No. 11/464,793.

USPTO Supplemental Notice of Allowability dated Dec. 31, 2009 for U.S. Appl. No. 11/464,793.

USPTO Notice of Allowance and Fee(s) Due dated Dec. 23, 2009 for U.S. Appl. No. 11/464,812.

USPTO Supplemental Notice of Allowability dated Dec. 31, 2009 for U.S. Appl. No. 11/484,812.

USPTO Notice of Allowance and Fee(s) Due dated Dec. 17, 2009 for U.S. Appl. No. 11/464,815.

(56) References Cited

OTHER PUBLICATIONS

USPTO Supplemental Notice of Allowability dated Dec. 31, 2009 for U.S. Appl. No. 11/464,815.
USPTO Office Action dated Jun. 23, 2008 for U.S. Appl. No. 11/464,782.
USPTO Office Action dated Oct. 29, 2008 for U.S. Appl. No. 11/464,782.
USPTO Office Action dated May 21, 2009 for U.S. Appl. No. 11/464,782.
USPTO Office Action dated Jun. 23, 2008 for U.S. Appl. No. 11/464,790.
USPTO Office Action dated Oct. 31, 2008 for U.S. Appl. No. 11/464,790.
USPTO Office Action dated Apr. 15, 2009 for U.S. Appl. No. 11/464,790.
USPTO Office Action dated Jun. 23, 2008 for U.S. Appl. No. 11/464,793.
USPTO Office Action dated Oct. 29, 2008 for U.S. Appl. No. 11/464,793.
USPTO Office Action dated May 22, 2009 for U.S. Appl. No. 11/464,793.
USPTO Office Action dated Aug. 19, 2009 for U.S. Appl. No. 11/464,807.
USPTO Office Action dated Jun. 23, 2008 for U.S. Appl. No. 11/464,812.
USPTO Office Action dated Oct. 29, 2008 for U.S. Appl. No. 11/464,812.
USPTO Office Action dated May 12, 2009 for U.S. Appl. No. 11/464,812.
USPTO Office Action dated Jun. 23, 2008 for U.S. Appl. No. 11/464,815.
USPTO Office Action dated Oct. 29, 2008 for U.S. Appl. No. 11/464,815.
USPTO Office Action dated May 12, 2009 for U.S. Appl. No. 11/464,815.
Notification of Transmittal of International Preliminary Examination Report for PCT/US08/54590 dated Aug. 7, 2009.
Notification of Transmittal of International Search Report, International Search Report and Written Opinion for PCT/US08/54590 dated Aug. 22, 2008.
Notification of Transmittal of International Search Report, International Search Report and Written Opinion for PCT/US08/54508 dated Aug. 27, 2008.
U.S. Appl. No. 60/689,670, filed Jun. 13, 2006; Inventor: Tzony Siegal; Title: Directional Drilling System.
John A. Carrino, Roxanne Chan and Alexander R. Vaccaro, "Vertebral Augmentation: Vertebroplasty and Kyphoplasty", Seminars in Roentgenology, vol. 30, No. 1 Jan. 2004.
Ajeya P. Joshi, M.D. and Paul A. Glazer, M.D., "Vertebroplasty: Current Concepts and Outlook", 2003 from http://www.spineuniverse.com/displayarticle, php/article2076.html.
PCT Invitation to Pay Additional Fees (Form PCT/ISA/206), Re: International application No. PCT/US2006/031861 dated Jan. 15, 2007.
Annex to PCT Invitation to Pay Additional Fees, Re: International application No. PCT/US2006/031861 dated Jan. 15, 2007.
International Preliminary report on patentability and PCT Written Opinion of the International Searching Authority,PCT Application No. US2006/031861 dated Feb. 28, 2008.

\* cited by examiner

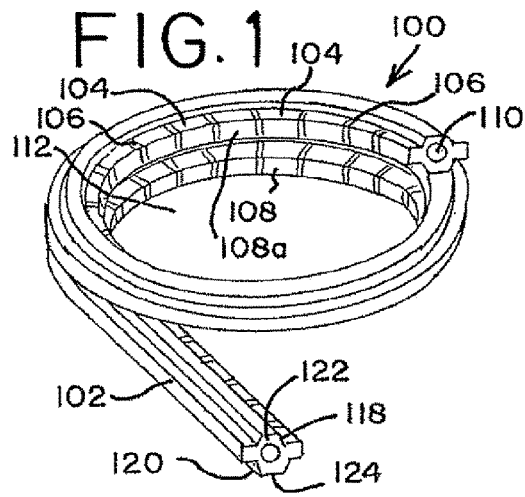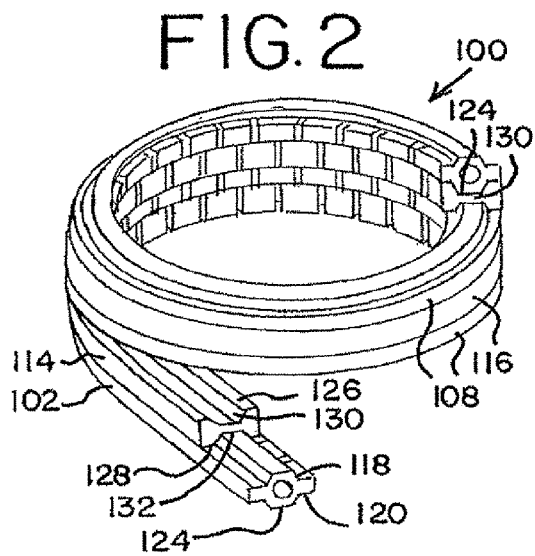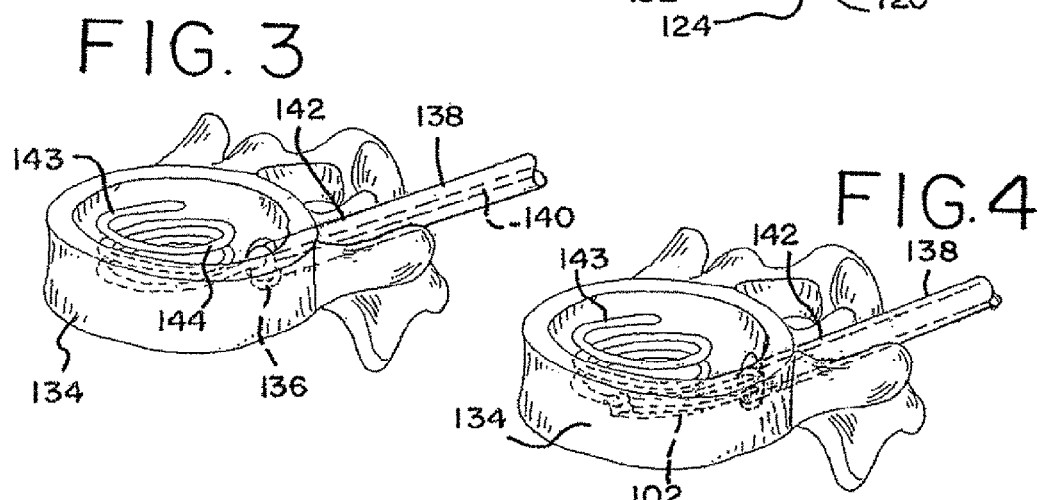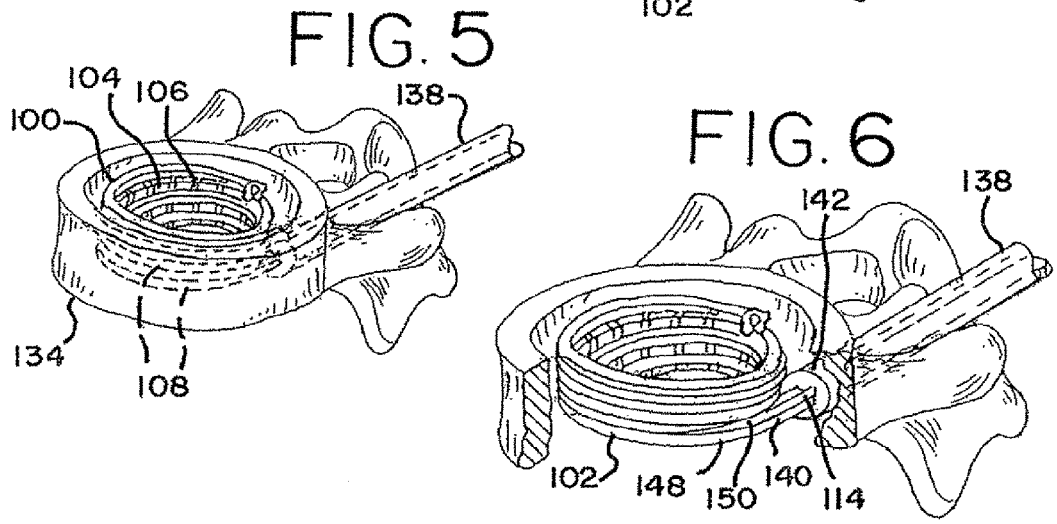

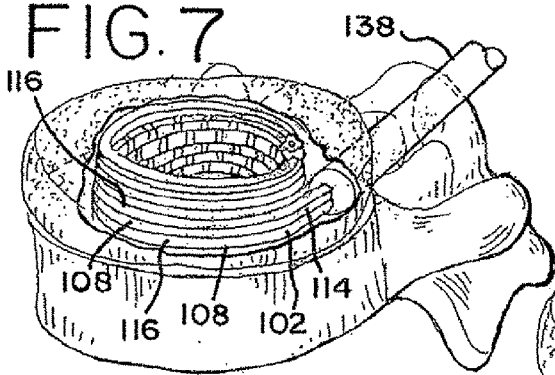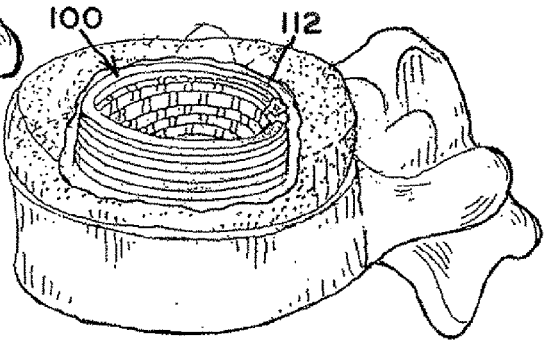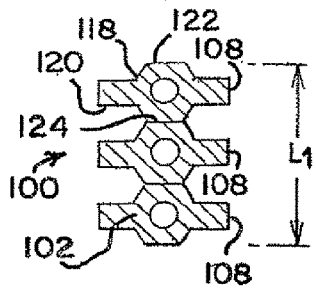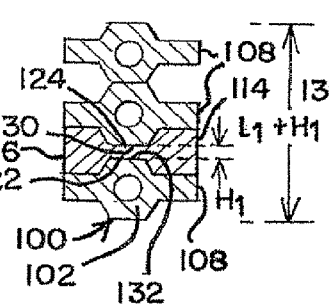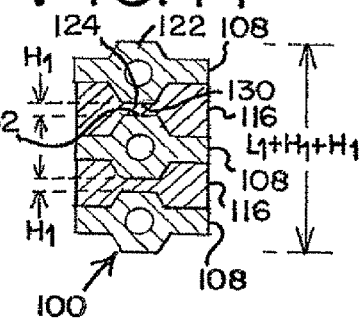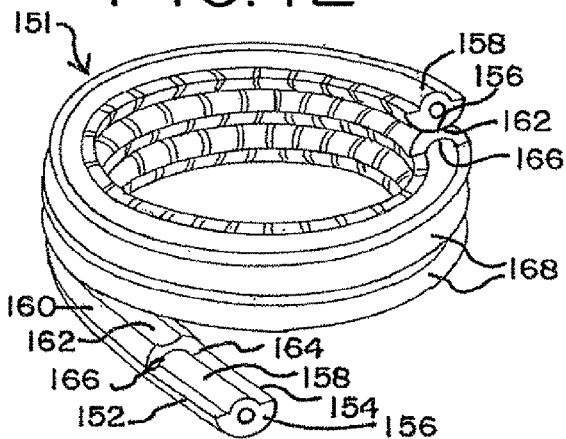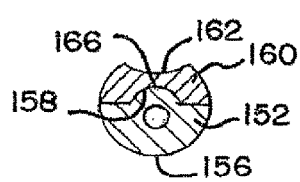

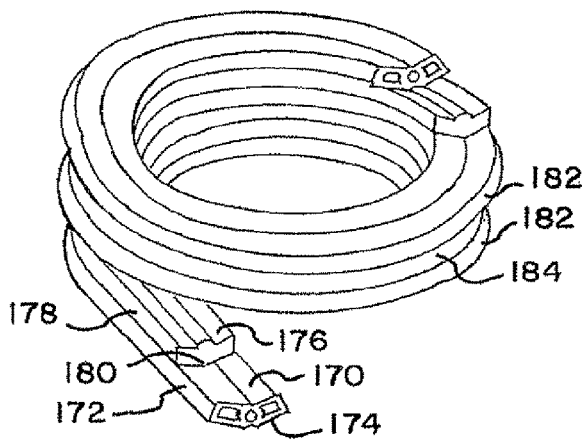
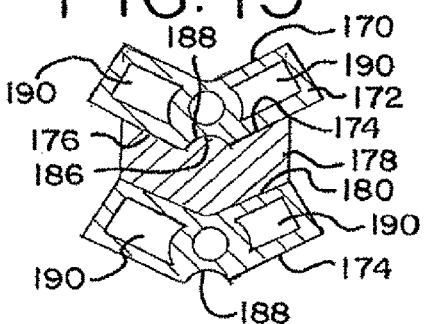
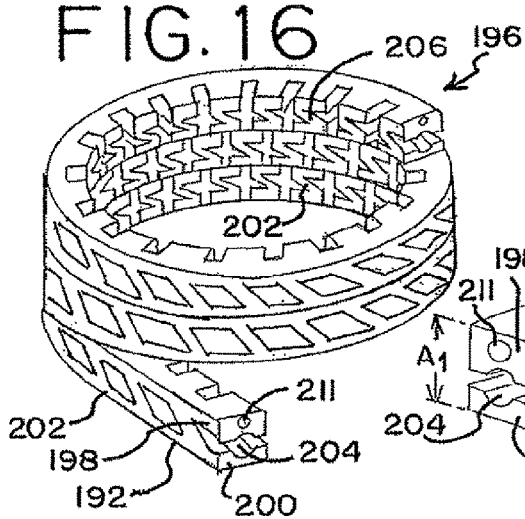
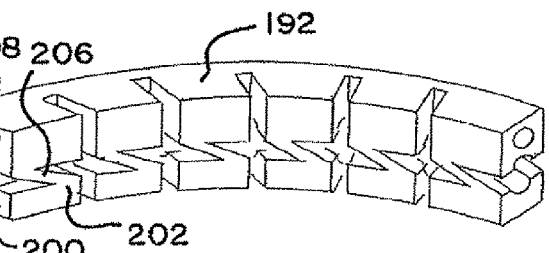
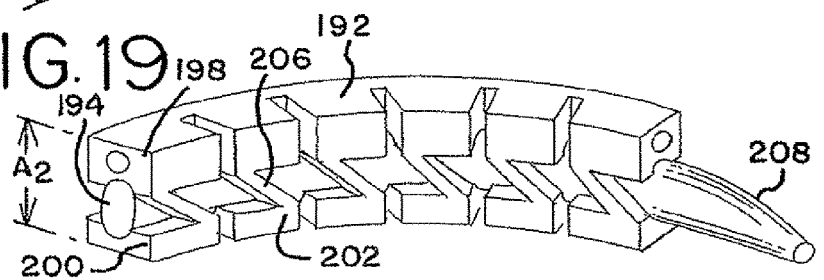

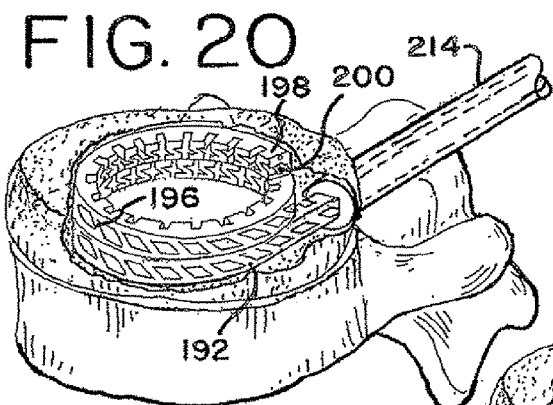
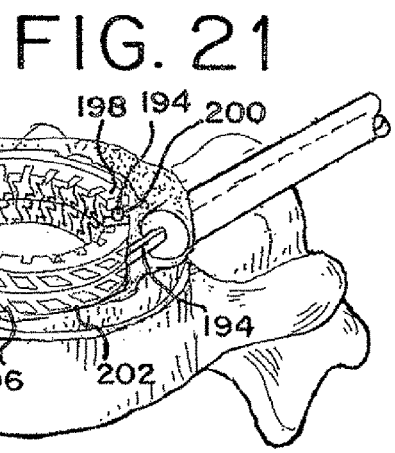
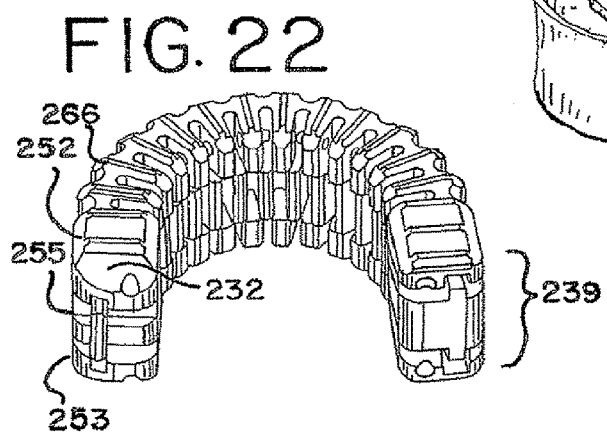
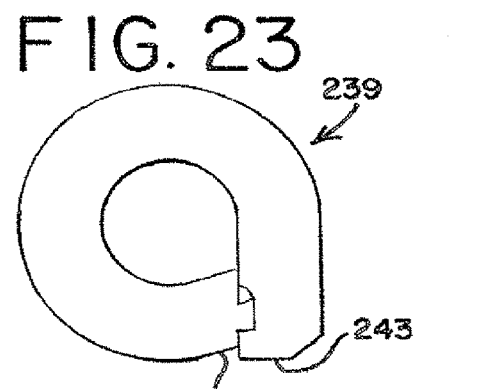
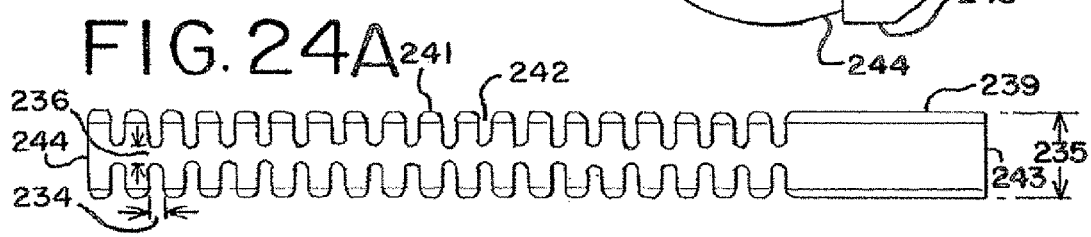
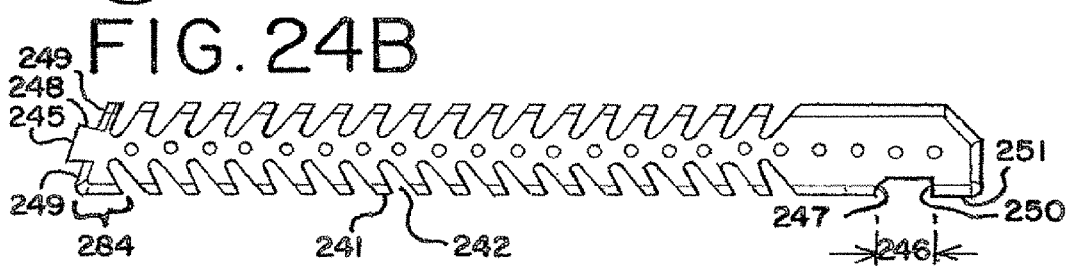

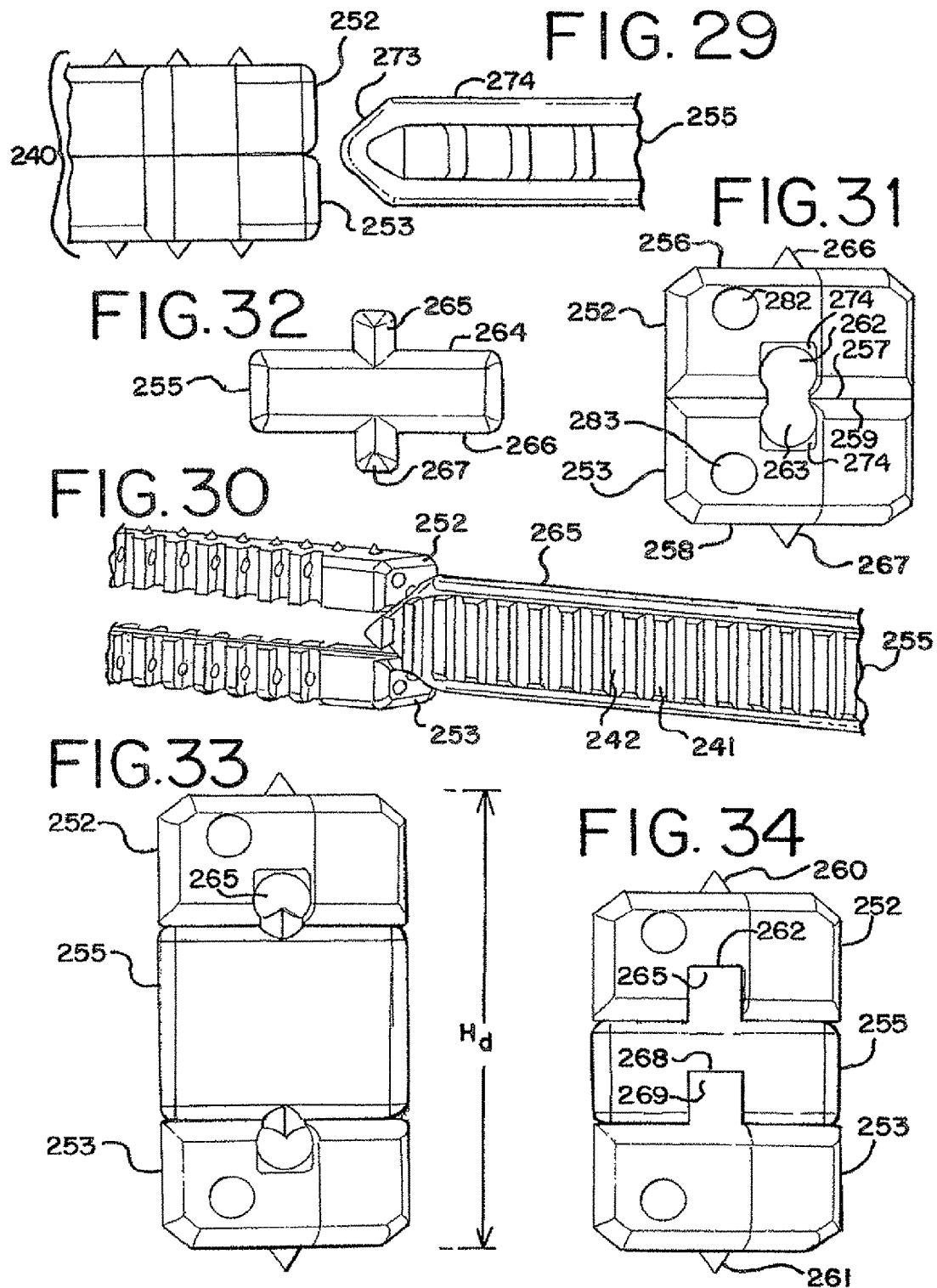

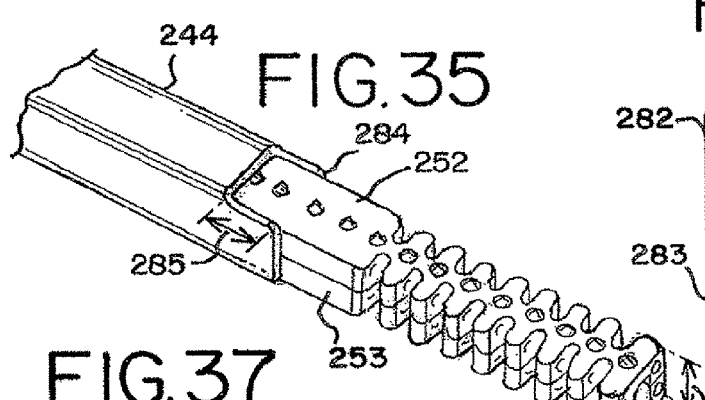
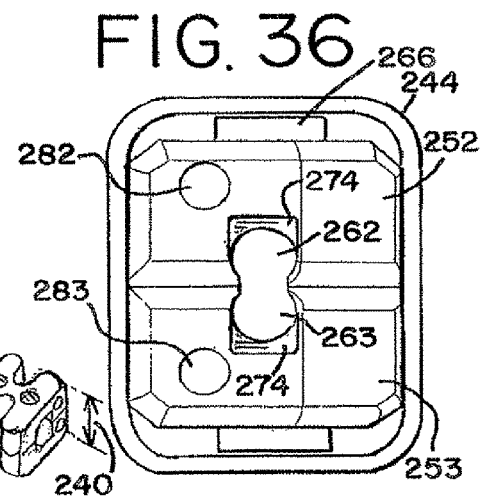
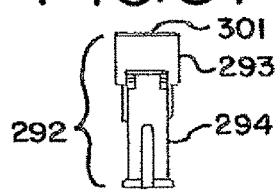
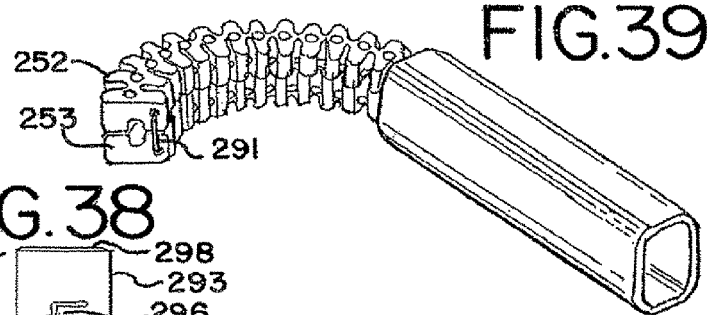
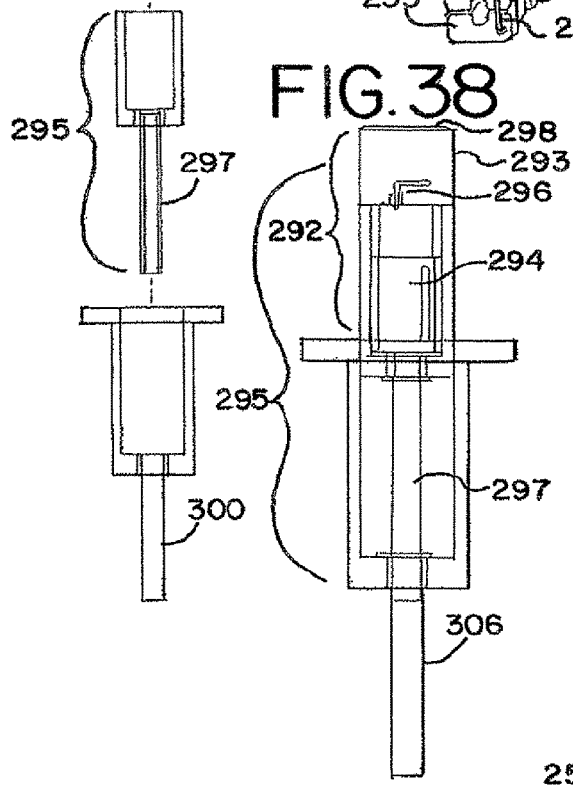
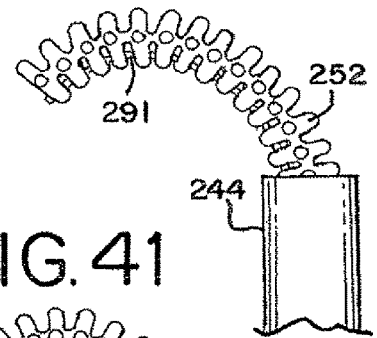
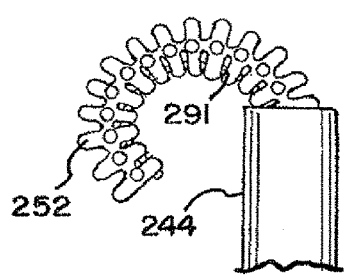

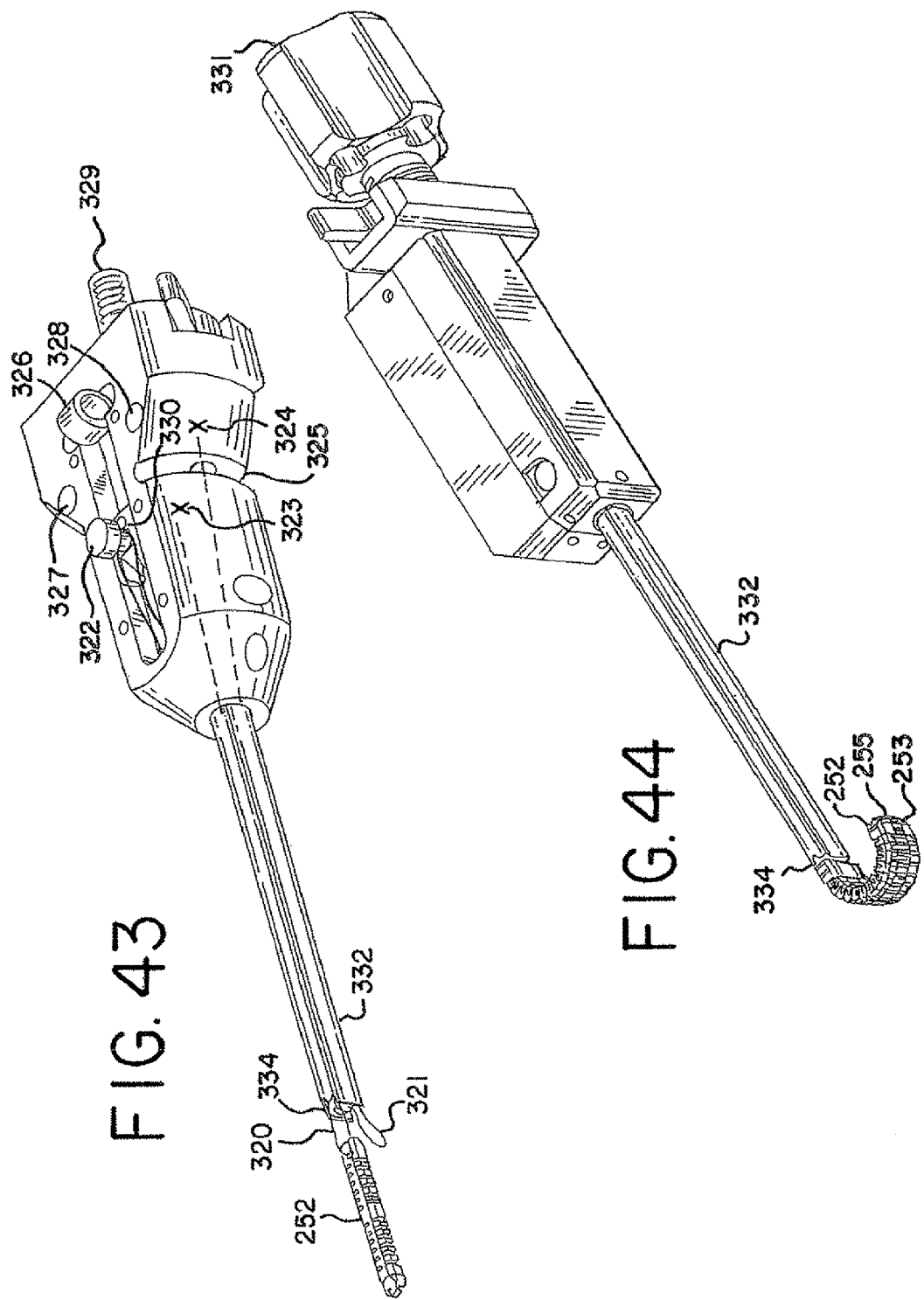

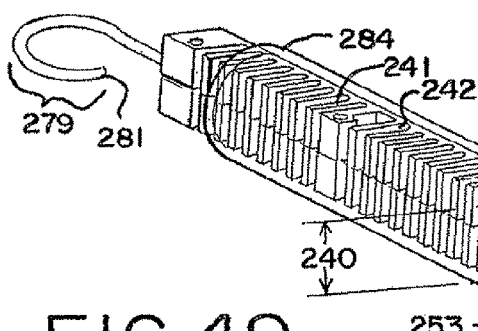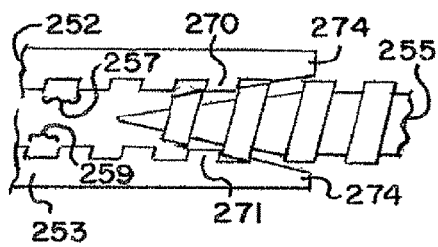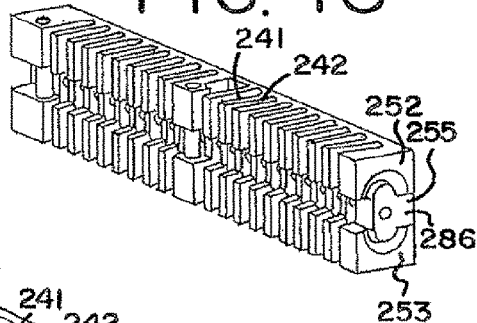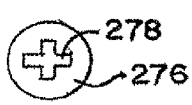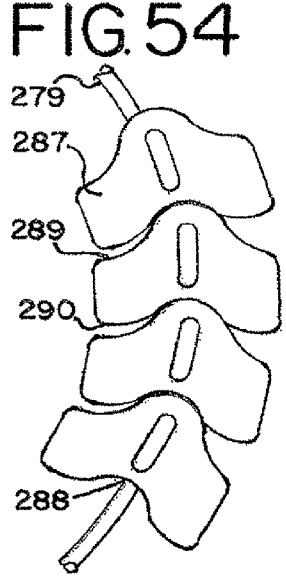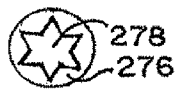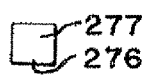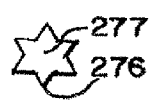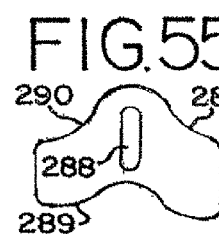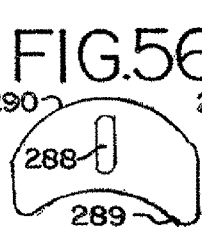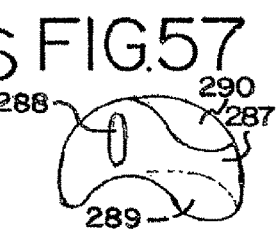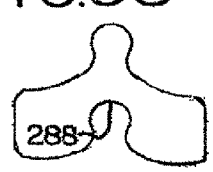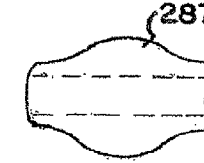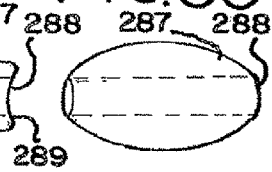

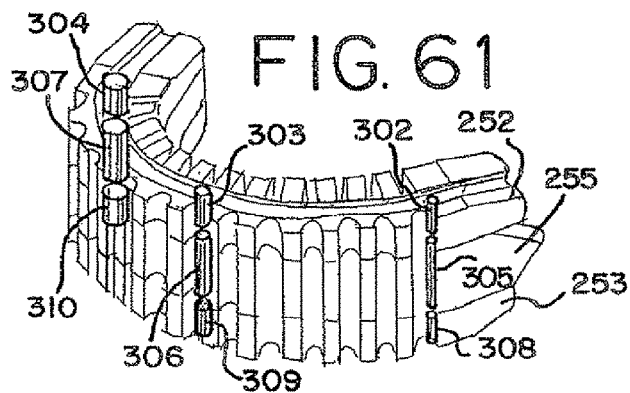
FIG. 61
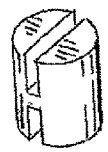
FIG. 64
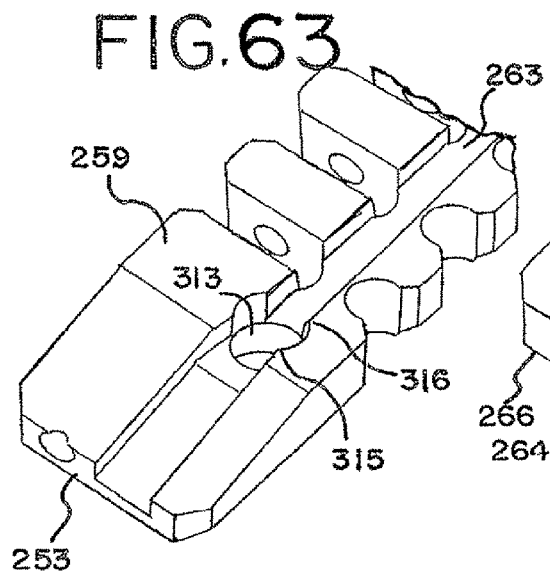
FIG. 63
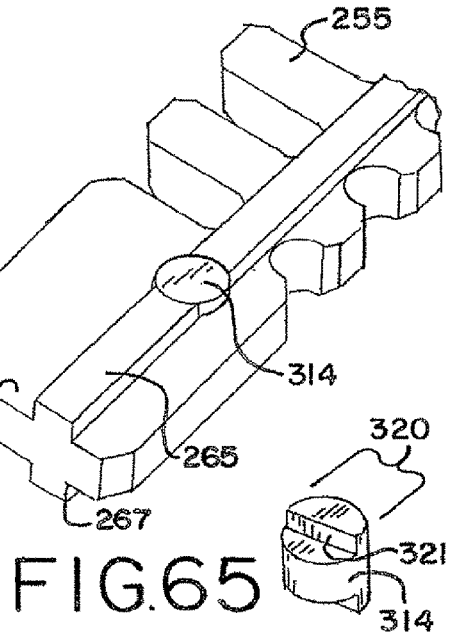
FIG. 62
FIG. 65
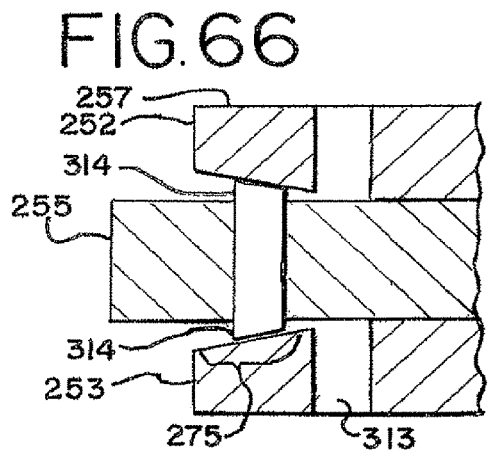
FIG. 66
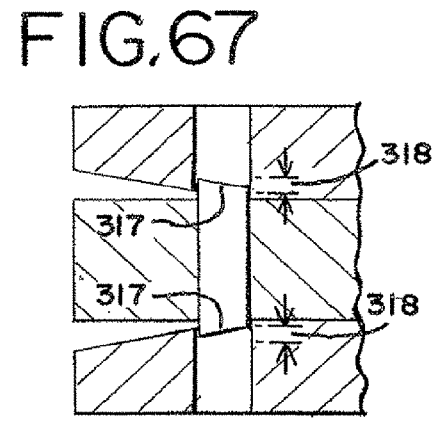
FIG. 67

DEVICES FOR TREATING THE SPINE

The present application is a continuation of U.S. patent application Ser. No. 15/994,050, filed on May 31, 2018, which is a continuation of U.S. patent application Ser. No. 15/297,634, filed on Oct. 19, 2016, which is a continuation of U.S. patent application Ser. No. 14/613,551, filed Feb. 4, 2015, which is a divisional of U.S. patent application Ser. No. 13/869,075, filed Apr. 24, 2013, which is a continuation of U.S. patent application Ser. No. 12/035,298, filed Feb. 21, 2008, which claims the benefit of U.S. Provisional Patent Application No. 60/936,974, filed Jun. 22, 2007, all of which are incorporated herein by reference.

FIELD OF THE INVENTION

The present invention generally relates to apparatus and methods employed in minimally invasive surgical procedures and more particularly to various aspects of apparatus and methods for separating and/or supporting tissue layers, especially in the spine.

BACKGROUND OF THE INVENTION

A variety of physical conditions involve two tissue surfaces that, for diagnosis or treatment of the condition, need to be separated or distracted or maintained in a separated condition from one another and then supported in a spaced-apart relationship. Such separation or distraction may be to gain exposure to selected tissue structures, to apply a therapeutic pressure to selected tissues, to return or reposition tissue structures to a more normal or original anatomic position and form, to deliver a drug or growth factor, to alter, influence or deter further growth of select tissues or to carry out other diagnostic or therapeutic procedures. Depending on the condition being treated, the tissue surfaces may be opposed or contiguous and may be bone, skin, soft tissue, or a combination thereof.

One location of the body where tissue separation is useful as a corrective treatment is in the spinal column. Developmental irregularities, trauma, tumors, stress and degenerative wear can cause defects in the spinal column for which surgical intervention is necessary. Some of the more common defects of the spinal column include vertebral compression fractures, degeneration or disruption of an intervertebral disc and intervertebral disc herniation. These and other pathologies of the spine are often treated with implants that can restore vertebral column height, immobilize or fuse adjacent vertebral bones, or function to provide flexibility and restore natural movement of the spinal column. Accordingly, different defects in the spinal column require different types of treatment, and the location and anatomy of the spine that requires corrective surgical procedures determines whether an immobilizing implantable device or a flexible implantable device is used for such treatment.

In a typical spinal corrective procedure involving distraction of tissue layers, damaged spinal tissue is removed or relocated prior to distraction. After the damaged tissue has been removed or relocated, adjacent spinal tissue layers, such as adjacent bone structures, are then distracted to separate and restore the proper distance between the adjacent tissue layers. Once the tissue layers have been separated by the proper distance, an immobilizing or flexible device, depending on the desired treatment, is implanted between the tissue layers. In the past, the implantable treatment devices have been relatively large cage-like devices that require invasive surgical techniques which require relative large incisions into the human spine. Such invasive surgical techniques often disrupt and disturb tissue surrounding the surgical site to the detriment of the patient.

Therefore, there remains a need for implantable treatment devices and methods that utilize minimally invasive procedures.

Such methods and devices may be particularly needed in the area of intervertebral or disc treatment. The intervertebral disc is divided into two distinct regions: the nucleus pulposus and the annulus fibrosus. The nucleus lies at the center of the disc and is surrounded and contained by the annulus. The annulus contains collagen fibers that form concentric lamellae that surround the nucleus and insert into the endplates of the adjacent vertebral bodies to form a reinforced structure. Cartilaginous endplates are located at the interface between the disc and the adjacent vertebral bodies.

The intervertebral disc is the largest avascular structure in the body. The cells of the disc receive nutrients and expel waste by diffusion through the adjacent vascularized endplates. The hygroscopic nature of the proteoglycan matrix secreted by cells of the nucleus operates to generate high intra-nuclear pressure. As the water content in the disc increases, the intra-nuclear pressure increases and the nucleus swells to increase the height of the disc. This swelling places the fibers of the annulus in tension. A normal disc has a height of about 10-15 mm.

There are many causes of disruption or degeneration of the intervertebral disc that can be generally categorized as mechanical, genetic and biochemical. Mechanical damage includes herniation in which a portion of the nucleus pulposus projects through a fissure or tear in the annulus fibrosus. Genetic and biochemical causes can result in changes in the extracellular matrix pattern of the disc and a decrease in biosynthesis of extracellular matrix components by the cells of the disc. Degeneration is a progressive process that usually begins with a decrease in the ability of the extracellular matrix in the central nucleus pulposus to bind water due to reduced proteoglycan content. With a loss of water content, the nucleus becomes desiccated resulting in a decrease in internal disc hydraulic pressure, and ultimately to a loss of disc height. This loss of disc height can cause the annulus to buckle with non-tensile loading and the annular lamellae to delaminate, resulting in annular fissures. Herniation may then occur as rupture leads to protrusion of the nucleus.

Proper disc height is necessary to ensure proper functionality of the intervertebral disc and spinal column. The disc serves several functions, although its primary function is to facilitate mobility of the spine. In addition, the disc provides for load bearing, load transfer and shock absorption between vertebral levels. The weight of the person generates a compressive load on the discs, but this load is not uniform during typical bending movements. During forward flexion, the posterior annular fibers are stretched while the anterior fibers are compressed. In addition, a translocation of the nucleus occurs as the center of gravity of the nucleus shifts away from the center and towards the extended side.

Changes in disc height can have both local and global effects. On the local (or cellular, level) decreased disc height results in increased pressure in the nucleus, which can lead to a decrease in cell matrix synthesis and an increase in cell necrosis and apoptosis. In addition, increases in intra-discal pressure create an unfavorable environment for fluid transfer into the disc, which can cause a further decrease in disc height.

Decreased disc height also results in significant changes in the global mechanical stability of the spine. With decreasing height of the disc, the facet joints bear increasing loads and may undergo hypertrophy and degeneration, and may even act as a source of pain over time. Decreased stiffness of the spinal column and increased range of motion resulting from loss of disc height can lead to further instability of the spine, as well as back pain.

Radicular pain may result from a decrease in foraminal volume caused by decreased disc height. Specifically, as disc height decreases, the volume of the foraminal canal, through which the spinal nerve roots pass, decreases. This decrease may lead to spinal nerve impingement, with associated radiating pain and dysfunction Finally, adjacent segment loading increases as the disc height decreases at a given level. The discs that must bear additional loading are now susceptible to accelerated degeneration and compromise, which may eventually propagate along the destabilized spinal column.

In spite of all of these detriments that accompany decreases in disc height, where the change in disc height is gradual many of the ill effects may be "tolerable" to the spine and patient and may allow time for the spinal system to adapt to the gradual changes. However, the sudden decrease in disc volume caused by the surgical removal of the disc or disc nucleus may increase the local and global problems noted above.

Many disc defects are treated through a surgical procedure, such as a discectomy in which the nucleus pulposus material is removed. During a total discectomy, a substantial amount (and usually all) of the volume of the nucleus pulposus is removed and immediate loss of disc height and volume can result. Even with a partial discectomy, loss of disc height can ensue. Discectomy alone is the most common spinal surgical treatment, frequently used to treat radicular pain resulting from nerve impingement by disc bulge or disc fragments contacting the spinal neural structures.

The discectomy may be followed by an implant procedure in which a prosthesis is introduced into the cavity left in the disc space when the nucleus material is removed. Thus far, the most common prosthesis is a mechanical device or a "cage" that is sized to restore the proper disc height and is configured for fixation between adjacent vertebrae. These mechanical solutions take on a variety of forms, including solid kidney-shaped implants, hollow blocks filled with bone growth material, push-in implants and threaded cylindrical cages.

A challenge in the use of a posterior procedure to install spinal prosthesis devices is that a device large enough to contact the end plates and expand the space between the end plates of the same or adjacent vertebra must be inserted through a limited space. In the case of procedures to increasing intervertebral spacing, the difficulties are further increased by the presence of posterior osteophytes, which may cause "fish mouthing" or concavity of the posterior end plates and result in very limited access to the disc. A further challenge in degenerative disc spaces is the tendency of the disc space to assume a lenticular shape, which requires a relatively larger implant than often is easily introduced without causing trauma to the nerve roots. The size of rigid devices that may safely be introduced into the disc space is thereby limited.

While cages of the prior art have been generally successful in promoting fusion and approximating proper disc height, typically these cages have been inserted from the posterior approach, and are therefore limited in size by the interval between the nerve roots. Further, it is generally difficult, if not impossible to implant from the posterior approach a cage that accounts for the natural lordotic curve of the lumber spine.

It is desirable to reduce potential trauma to the nerve roots and yet still allow restoration or maintenance of disc space height in procedures involving vertebrae fusion devices and disc replacement, containment of the nucleus of the disc or prevention of herniation of the nucleus of the disc. In general minimally invasive surgical techniques reduce surgical trauma, blood loss and pain. However, despite the use of minimally invasive techniques, the implantation of cage devices for treating the spine typically involves nerve root retraction, an inherently high risk procedure. It is therefore desirable to reduce the degree of invasiveness of the surgical procedures required to implant the device, which may also serve to permit reduction in the pain, trauma, and blood loss as well as the avoidance and/or reduction of the nerve root retraction.

In minimally invasive procedures, to monitor placement, it is useful that implant devices inserted into spinal tissue be detectable using fluoroscopic imaging systems. However if a device is visible using X-ray technology, then the device can interfere with the detection and monitoring of spinal tissues, such as bone growing into the disc space after a vertebral fusion procedure. Additional advances would also be useful in this area.

SUMMARY OF INVENTION

The present invention relates to various aspects of distraction systems and methods for separating, supporting or both separating and supporting tissue layers in the human body.

The present invention, in one aspect, is directed to a tissue distraction device comprising a first elongated member insertable between tissue layers and adapted to define a structure in situ having a dimensional aspect in a direction extending between the tissue layers. The device also includes an augmenting elongated member operatively cooperative with the first member to increase the dimensional aspect of the structure in situ.

In another aspect, a tissue distraction device is provided by the present invention comprising a first elongated member, a second elongated member, and an augmenting elongated member, with the first elongated member adjacent the second elongated member. The first and second elongated members are insertable between tissue layers to define a structure in situ having a dimensional aspect in a direction extending between the tissue layers. An augmenting elongated member is operatively cooperative with the first and second members to increase the dimensional aspect of the structure in situ.

In accordance with another aspect of the invention a method is provided for separating tissue layers. The method includes inserting a first elongated member between tissue layers to form a structure in situ with a dimensional aspect in a direction extending between the tissue layers. The method further includes inserting an augmenting elongated member between tissue layers, the augmenting elongated member cooperating with the first member to increase the dimensional aspect of the structure in situ and to cause spreading of the tissue layers.

In accordance with yet a further aspect of the present invention a method of separating tissue layers is provided that comprises inserting first and second elongated members. The method includes inserting first elongated member and the second elongated member between tissue layers to form a structure in situ with a dimensional aspect in a direction extending between the tissue layers. The method further includes inserting and augmenting elongated member between tissue layers the augmenting elongated member cooperating with the first and second elongated members to increase the dimensional aspect of the structure in situ and to cause spreading of the tissue layers.

These and other aspects of the present invention are set forth in the following detailed description. In that respect, it should be noted that the present invention includes a number of different aspects which may have utility alone and/or in combination with other aspects. Accordingly, the above summary is not exhaustive identification of each such aspect that is now or may hereafter be claimed, but represents only an overview to assist in understanding the more detailed description that follows. The scope of the invention is as set forth in the claims now or hereafter filed.

BRIEF DESCRIPTION OF THE FIGURES

In the course of this description, reference will be made to the accompanying drawings, wherein:

FIG. 1 is a perspective view of one embodiment of a distraction device support structure defined by a first elongated member that has a coil-like or a spring configuration;

FIG. 2 is a perspective view of the distraction device support structure of FIG. 1 augmented by an augmenting elongated member positioned between the windings of the first elongated member;

FIG. 3 is a perspective view of a vertebra having a guide member deployed therein;

FIG. 4 is a perspective view of the vertebra of FIG. 3 to show a first elongated member partially deployed within the vertebral body;

FIG. 5 is a perspective view of the vertebra of FIG. 3 shown with the first elongated member fully deployed to define a support structure within the vertebral body;

FIG. 6 is a perspective view of the vertebra of FIG. 3 having portions broken away to show an augmenting elongated member being initially deployed between the windings of the first elongated member;

FIG. 7 is a perspective view of a vertebral body having portions broken away to show the deployment of an augmenting elongated member to augment the distraction device support structure;

FIG. 8 is a perspective view of a vertebral body having portions broken away to show the augmented distraction device support structure implanted therein;

FIG. 9 is a partial cross-sectional view of a distraction device support structure prior to deployment of the augmenting elongated member;

FIG. 10 is a partial cross-sectional view of the distraction device support structure of FIG. 9 shown with the augmenting elongated member partially deployed;

FIG. 11 is a partial cross-sectional view of the distraction device support structure of FIG. 9 shown with the augmenting elongated member fully deployed;

FIG. 12 is a perspective view of another embodiment of a distraction device support structure defined by a first elongated member and an augmenting elongated member;

FIG. 13 is a partial cross-sectional view of the distraction device support structure of FIG. 12 to show the augmenting and first elongated members;

FIG. 14 is a perspective view of another embodiment of a distraction device support structure defined by a first elongated member and an augmenting elongated member;

FIG. 15 is a partial cross-sectional view of the distraction device support structure of FIG. 14 illustrating a stress relief region in the first elongated member;

FIG. 16 is a perspective view of a distraction device with first elongated member having expandable walls or variable height;

FIG. 17 is a perspective view of a portion of the first elongated member of the distraction device of FIG. 16;

FIG. 18 is a perspective view of a portion of the augmenting elongated member of the distraction device of FIG. 16;

FIG. 19 is a perspective view of the augmenting elongated member operatively cooperating with the first elongated member of FIG. 16;

FIG. 20 is a perspective view of a vertebral disc having portions broken away to show the first elongated member of FIG. 16 deployed therein to form a structure in situ having a dimensional aspect in a direction between extending tissue layers (end plates of the disc);

FIG. 21 is a perspective view of the vertebral disc of FIG. 20 having portions broken away to show the augmenting elongated member being deployed within the first elongated member to augment or increase the dimensional aspect of the distraction device support structure;

FIG. 22 is a perspective view of a semicircular distraction device having a first elongated member, a second elongated member and an augmenting elongated member forming a structure as it would appear in situ in a disc or vertebra;

FIG. 23 is a top view of another embodiment a distraction device support structure with a protrusion on the distal end of the device interacting with a recess near the distal end of the device;

FIG. 24a is a top view of a elongated member of a distraction device having spaced-apart teeth and intermediate slots;

FIG. 24b is a top view of an elongated member of a distraction device having spaced-apart teeth and slots as well as a protrusion at the distal end and a notch or recess near the proximal end of the distraction device that could form into the structure in situ as shown in situ as shown in FIG. 23;

FIG. 29 is a side view of portions of a distraction device showing a tapered distal end of an augmenting elongated member approaching the proximal end of the first and second elongated members of the device;

FIG. 30 is a perspective view of portions showing the tapered distal end of an augmenting elongated member entering a ramped opening formed by the proximal ends of first and second elongated members;

FIG. 31 is an proximal end-view of first and second elongated members of a distraction device, showing wire lumens, tissue engaging protrusions, and elongated grooves with ramped entry as employed in FIG. 30;

FIG. 32 is an end-view of another embodiment of an augmenting elongated member of a distraction device with protrusions on top and bottom surfaces;

FIG. 33 is an end-view of a deployed augmenting elongated member with bulbous ends on its raised ribs interacting with the elongated grooves of the first and second elongated members as employed in FIG. 30;

FIG. 34 is an end-view of a deployed augmenting elongated member with a raised rib interacting with a groove in a first elongated member and a groove in the augmenting elongated member interacting with a raised rib of a second elongated member;

FIG. 35 is a perspective view of first and second elongated members of a distraction device emerging from a cannula with cutouts on the top and bottom distal end of cannula;

FIG. 36 is an end view of first and second elongated members of a distraction device when located in a cannula;

FIG. 37 is an exploded side view of a delivery device showing a thumbknob and a puller platform to control the tension on pull wires, plunger body, inner delivery cannula, and outer syringe body with main delivery cannula;

FIG. 38 is side view the assembled delivery device of FIG. 37 with the pull wire ferrule attaching a pull wire to the puller platform;

FIG. 39 is a perspective view of the pull wire system and the first and second elongated members with tension on the pull wires causing curvature of the elongated members emerging from the cannula;

FIG. 40. is a top view of the pull wire system and the first and second elongated members of FIG. 39 with tension on the pull wires causing curvature of the elongated members emerging from a cannula;

FIG. 41. is a top view of the pull wire system and the first and second elongated members of FIG. 39 with an increased tension on the pull wires causing increased curvature of the elongated members emerging from a cannula;

FIG. 43 are a perspective views of delivery device with anchor loops to attach elongated members;

FIG. 44 is a perspective view of a distraction device with curvature controlled by pull wires and attached to a delivery device by anchor loops;

FIG. 47 is a perspective view of a guide wire delivery system with first second and augmenting elongated members loaded on the guide wire in a cannula;

FIG. 48 is a perspective view of the distraction device of FIG. 47 with the augmenting elongated member deployed using a guide wire between the first and second elongated members, for clarity the distraction device is shown as straight, although it is preferably in a curved configuration in situ;

FIG. 49 is a longitudinal cross-section of a distraction device with protrusions or threads on the augmenting elongated member interacting with protrusions on the bottom surface of the first elongated member and the top surface of a second elongated member;

FIGS. 50, 51, 52 and 53 are end views of examples of the proximal ends of the augmenting elongated members configured to interact with torque delivery devices;

FIG. 54 is a top view of a segmented augmenting member loaded on a delivery wire;

FIGS. 55-60 are views of examples of alternative segments of segmented augmenting members, FIGS. 55, 56, 58, 59 and 60 are top views of segments and FIG. 57 is a perspective view of a segment;

FIG. 61 is a perspective view of a distraction device with radiopaque markers in the augmenting, first and second elongated members;

FIG. 62 is a perspective view of an augmenting elongated member with a pin extending above the top and bottom surfaces thereof to provide a protrusion useful as an interlocking feature to interlock with the first and/or second elongated members;

FIG. 63 is a perspective view of an elongated member with a recess extending that acts as an interlocking feature to receive the pin of the augmenting elongated member of FIG. 62;

FIGS. 64 and 65 are perspective views of examples of pin-type interlocking features;

FIG. 66 is a cross sectional view of a proximal end of distraction device with the interlocking features of the augmenting, first and second elongated members unengaged;

FIG. 67 is a cross sectional view of a proximal end of distraction device with the interlocking feature of the augmenting, first and second elongated members engaged;

DETAILED DESCRIPTION

Figure 25:
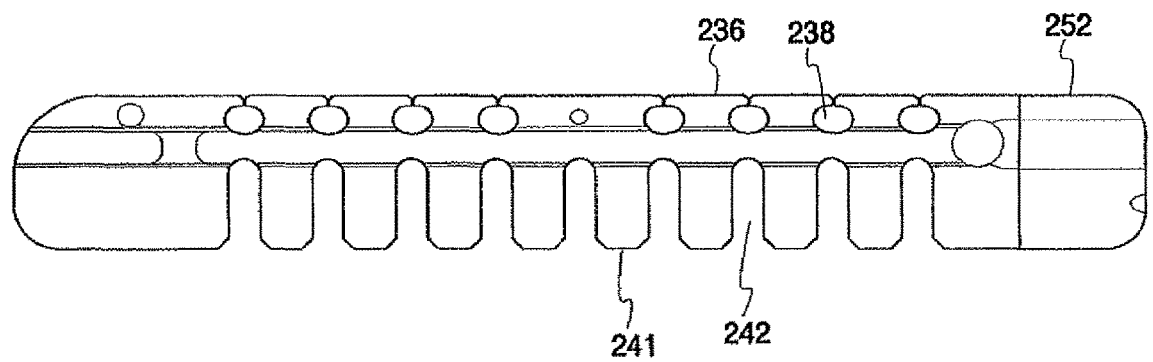
FIG. 25 is a perspective view of an augmenting elongated member of a distraction device having first conformation of spaced-apart teeth and slots along one side and a second conformation on a second side to accommodate bending in one direction and resisting bending in an opposite direction.

The devices and methods of the present invention provide multiple features of distraction devices, distraction device support structures and deployment systems that can be used to actively separate tissue layers by engaging them and forcing them apart, or to support the separation of tissue layers separated by the distraction device itself or by other devices or processes or a combination of these.

As used herein, the terms "distraction device" and "distraction device support structure" are intended to have a general meaning and is not limited to devices that only actively separate tissue layers, only support tissue layers or only both actively separate and support tissue layers. For example, the distraction device and support structure in general can be used to actively separate layers of tissue and then be removed after such separation, or the distraction device and the support structure could be used to support layers of tissue that have been previously separated by a different device. Alternatively, the distraction device and support structure can be used to actively separate the layers of tissue and remain in place to support the layers of tissue in order to maintain such separation. Unless more specifically set forth in the claims, as used herein, "distraction device" and "distraction device support structure" encompasses any and all of these. In addition, it should be noted that the references to "first" and "second" members or devices are for convenience in the written description. They may be combined to provide a single distraction assembly or structure of selected distraction height, and the assembly is not limited to only two "devices" or to only three "sleeves" or "members." In keeping with the broader aspects of the present invention the specific number of "devices" or "sleeves" or "members" can be varied according to the intended usage or design considerations.

It should also be understood that various embodiments of the device, system and method of the present invention are illustrated for purposes of explanation in the treatment of vertebral compression fractures, height restoration of a diseased disc, vertebral fusion procedures, replacement of removed discs or vertebra, intervertebral disc nucleus containment or annulus fibrous repair. However, in its broader aspects, the various features of the present invention are not limited to these particular applications and may be used in connection with other tissue layers, such as soft tissue layers, although it has particular utility and benefit in treatment of vertebral conditions within intervertebral discs or within vertebra themselves.

Various features of the devices and methods of the present invention are further described in U.S. Provisional Patent Application 60/963,974 and its attached Exhibits A, B, C, D and E which were filed Jun. 22, 2007 and are hereby incorporated herein by reference. Additionally, the devices, systems and methods described herein are particularly useful with medical devices and procedures that involve tissue distraction, for example, as described in the following co-owned patent applications: U.S. Provisional Applications Nos. (1) 60/708,691, filed Aug. 16, 2005; (2) 60/738,432, filed November 21, (3) 60/784,185, filed Mar. 21, 2006, (4) 60/886,838, filed Jan. 26, 2007, and (5) 60/890,868 filed Feb. 21, 2007; and U.S. patent applications Nos. (1) Ser. No. 11/464,782, (2) Ser. No. 11/464,790, (3) Ser. No. 11/464,793, (4) Ser. No. 11/464,807, (5) Ser. No. 11/464,812, and (6) Ser. No. 11/464,815, all of which were filed Aug. 15, 2006. Co-owned U.S. patent application Ser. No. 12/034,853, entitled "Devices For Treating The Spine", and 61/030,287, entitled "Method of Interdigitating Flowable Material With Bone Tissue", both of which were filed on Feb. 21, 2008 also described the devices, systems and methods described particularly useful with medical devices and procedures described herein. All of the foregoing co-owned applications are hereby incorporated herein by reference.

Distraction Device Systems and Methods of Use

FIG. 1 illustrates one embodiment of a distraction device support structure, generally designated as 100, defined by a first elongated member 102. The elongated member 102 is preferably comprised of elongated elements, such as a thread or ribbon, made of biocompatible materials that are suitable for long term implantation into human tissue where treatment is needed. The biocompatible materials may be calcium phosphate, tricalcium phosphate, hydroxyapatite, polyetheretherketones (PEEK), nylon, Nitinol (NiTi) or any other suitable biocompatible material.

During deployment, the first elongated member 102 preferably has a generally linear configuration for insertion into tissue or between tissue layers. When deployed into or between tissue, the first elongated member 102 changes, preferably by flexing or bending, to a generally less linear configuration to define a distraction device support structure. For example, in FIG. 1, the first elongated member 102 can be bent or configured to form or define the multi-tiered arrangement, scaffolding or platform of the coil or spring-like distraction device support structure 100 having a vertical extent (e.g., the distance between the uppermost and lowermost surfaces of the structure). The distraction device support structure 100 can serve to actively separate or support (or both) opposed tissue layers.

The first distraction device or member, hereafter first elongated member, 102 preferably includes features that add flexibility to the elongated member to assist in bending or changing the configuration of the elongated member from a generally linear configuration to a less linear configuration and vice versa. For example, the first elongated member 102 may include teeth 104 and slots 106 that aid in relieving stress and add flexibility to the elongated member.

To form the support structure 100, the first elongated member 102 can be configured into a helical configuration with preferably a tight pitch that has an essentially cylindrical configuration. As shown, each turn or winding 108 is wound on top of or below the previous winding 108a to form a plurality of stacked windings or tiers with lithe or no spacing between each winding or tier.

In one embodiment, the first elongated member 102 can be comprised of a shape memory material that naturally has the configuration of the distraction device support structure 100. To deploy a first elongated member 102 that is naturally shaped into the coil-like support structure 100, the elongated member 102 is inserted between the tissue layers in a generally linear configuration, typically through a cannula. Because of its shape memory properties, the elongated member 102 transforms from its generally linear configuration to its natural coil-like configuration to define the distraction device support structure 100 upon insertion between tissue layers.

In an alternative embodiment, the first elongated member 102 is made from a material that does not have shape memory properties or has very weak shape memory properties and a guide member such as a guide wire having a pre-selected shape is employed to deploy the first elongated member 102 between tissue layers and to configure the first elongated member into the distraction device support structure 100. As will be discussed in more detail below, when the first elongated member 102 is intended to be deployed by a use guide member, the first elongated member can include an aperture, such as aperture 110, shown in FIG. 1, extending along with the first elongated member for passage of a guide member therethrough. The guide member is inserted between tissue layers and formed into a pre-selected shape. The first elongated member is advanced along the pre-shaped guide member to form the distraction device support structure.

Preferably, the distraction device support structure 100 includes or defines an innerspace or resident volume 112. As used herein, "resident volume" refers generally to a structural characteristic of the support structure. The resident volume is a volume that is generally defined by the distraction device support structure. The resident volume is not necessarily a volume completely enclosed by the distraction device support structure and can be any volume generally defined by the elongated member(s). This term does not necessarily mean that the resident volume is an open or void volume or cavity and does not preclude a situation in which the resident volume is, at some point in time, filled with another material, such as bone filler, cement, bone graft material, therapeutic drugs or the like. It also does not preclude the resident volume from containing undisturbed human tissue that is located or remains within the resident volume during or after deployment of the elongated member(s), as will be explained in more detail below. For example, if the distraction device is employed to separate adjoining soft tissue layers, such as subcutaneous fat and underlying muscle tissue, the resident volume of the distraction device support structure may be hollow or void of tissue after separation. On the other hand, if inserted into a vertebra having cancellous bone tissue therein, the resident volume will contain undisturbed bone tissue and no void or cavity is formed by the elongated member(s).

The elongated member 102 may be used alone or in conjunction with an augmenting elongated distraction member device, such as spacer 114, that operatively cooperates with the first elongated member 102 in order to augment or increase the vertical extent of the distraction device support structure 100, as illustrated in FIG. 2. The elongated distraction or augmenting member 114, hereafter the augmenting elongated member is generally similar to the first elongated member 102 and is also preferably comprised of a generally elongated member made from or coated with biocompatible materials. In the embodiment illustrated in FIG. 2, the augmenting elongated member 114 operatively cooperates with the first elongated member 102 so that the windings 116 of the augmenting elongated member 114 are inserted between the windings 108 of the first elongated member 102 to increase the height of or otherwise augment vertical dimensional extent of the distraction device support structure 100 to engage and distract the facing tissue layers of the disc or vertebra.

Preferably, the first and augmenting elongated members 102, 114 have corresponding contoured surfaces that mechanically or frictionally cooperate or mate to assist in maintaining the positions of the first and augmenting elongated members relative to each other and to increase the stability of the support structure 100. For example, as illustrated in FIGS. 1, 2, 9, 10 and 11, the first elongated member 102 may have a generally cross-like cross-sectional shape that includes a top surface 118 and a bottom surface 120. The top surface 118 includes a protrusion 122 substantially extending along the center of the top of the first elongated member 102, and the bottom surface 120 includes a protrusion 124 substantially extending along the center of the bottom of the first elongated member 102. The augmenting elongated member 114 also includes a top contoured surface 126 and a bottom contoured surface 128. The top surface 126 of the augmenting elongated member 114 includes an indent or groove 130 that is configured to mate with the protrusion 124 of the bottom surface 120 of the first elongated member 102. The bottom surface 128 of the augmenting elongated member 114 includes an indent or a groove 132 that is configured to mate with the protrusion 122 of the top surface 118 of the first elongated member 102. The mating between the protrusions 122, 124 and groves 130, 132 also can function as a guide track that guides the augmenting elongated member 114 between the windings 108 of the first elongated member 102 as the augmenting elongated member is advanced between the windings 108 of the first elongated member. Furthermore, the first and augmenting elongated members 102, 114 could have additional mating surfaces extending from either side of the first and augmenting elongated member, which mate to provide added stability to the support structure 100.

FIG. 3 through FIG. 8 illustrates the deployment of the first and augmenting elongated members 102, 114 into a vertebral body 134. It will be understood that the methods described herein of deploying the first and augmenting elongated members into a vertebral body are for illustrative purposes and that the same or similar methods can be use to deploy the elongated members in other locations of the body, such as in an intervertebral disc or between other bone, skin or soft tissue.

Referring to FIG. 3, an access port 136 is made in the vertebral body 134 using instruments and endoscopic procedures generally know to those skilled in the art or described in the above referenced co-owned patent applications. A cannula 138 is then employed to advance a guide member 140, such as the illustrated guide wire, through the access port 136 and into the vertebral body 134. The guide member 140 is preferably comprised of a shape memory material, such as Nitinol or other suitable shape memory material, such as a shape memory polymer, that has a natural or pre-set shape, for example, the illustrated coiled configuration. As the guide member 140 is advanced through the cannula 138, the cannula constrains the guide member into a pre-deployed configuration, such as the illustrated generally elongated linear configuration, allowing an easy and minimally invasive deployment of the guide member into the treatment site. Because of the shape memory properties, the guide member 140 will return to its natural coil-shape or deployed configuration once the constraint is removed, i.e., as the guide member exits the distal end portion 142 of the cannula 138 and enters the vertebral body 134. The guide member 140 can be advanced through the cannula 138 manually or with the aid of an advancing mechanism, such as the advancing mechanisms described in the above referenced co-owned applications.

The guide member 140 is advanced and deployed into cancellous bone of the vertebral body 134 until the distal end portion 143 of the guide member 140 reaches the desired height or has the desired number of loops or windings 144. Depending on the desired procedure, the guide member 140 itself may function as a distraction device that contacts and separates the endplates of a damaged vertebra or disc.

As illustrated in FIG. 4, the first elongated member 102 is inserted over the proximal end portion 145 of the guide member 140, and a pusher member (not shown) is placed over the guide member behind or proximal the elongated member. The pusher member is employed to contact and advance the first elongated member 102 forward or distally over the guide member 140 and out of the distal end portion 142 of the cannula 138. As the first elongated member 102 is advanced forward (distally) over the guide member 140, the guide member guides the elongated member out of the distal end portion 142 of the cannula 138 and into vertebral body 134.

In the vertebral body 134, the first elongated member 102 follows along the coiled shaped distal end portion 143 of the guide member 140 and winds into a coil shaped distraction device support structure 100 (FIG. 5). The teeth 104 and slots 106 of the first elongated member 102 enhance the flexibility of the device and assists in its ability to follow the contour of the guide member. In this manner, the distal end portion of the guide member will define the shape of the first elongated member in situ, for instance in a vertebral body. With each formation of an additional coil or windings 108 of the support structure 100, the support structure increases in height. At this point during the procedure, the distraction device support structure formed by the first elongated member may or may not function to distract tissue, depending on the desired application. The support structure formed by the first elongated member has a dimensional extent, a height in this example, that extends in a direction between the tissue layers (the endplates of a single vertebra or opposed endplates of adjacent vertebra) to be distracted. In the case of the spine, the direction would be generally vertical when the patent is standing.

The first elongated member 102 is advanced over the guide member 140 until the proximal end portion 148 of the first member 102 exits the distal end portion 142 of the cannula 138 as illustrated in FIG. 6. While the guide member 140 retains the proximal end portion 148 of the first elongated member 102 in alignment with the distal end portion 142 of the cannula 138, the augmenting elongated member 114 is advanced through the cannula 138 and positioned so that the contoured surfaces of the augmenting elongated member 114 align and mate with contoured surfaces of the first elongated member 102, as discussed above. Alternatively, if the first and augmenting elongated members and the cannula are configured so that the first and augmenting elongated members can both reside in the cannula at the same time and be advanced through the cannula simultaneously, the proximal end portion of the first elongated member can reside in the distal end portion of the cannula as the augmenting elongated member is deployed to augment the support structure.

As the augmenting elongated member 114 is advanced out of the cannula 138, the augmenting member 114 is guided by the contoured surfaces between the windings 108 of the first elongated member 102. The augmenting member 114 can have a tapered or otherwise configured distal end portion 150 to aid in the insertion of the augmenting elongated member between the windings 108 of the first elongated member 102. The windings 116 of the augmenting elongated member are positioned between the windings 108 of the first elongated member thereby augmenting or increasing the height of the distraction device support structure 100, as illustrated in FIG. 7.

Referring to FIGS. 9, 10 and 11, as the augmenting elongated member 114 is inserted between the windings of the first elongated member 102, the dimensional extent (in this case, the vertical dimension or the height) of the support structure 100 is increased by the height of $H_1$ for every full winding 116 of the augmenting elongated member 114 that is inserted between the windings 108 of the first elongated member 102. For example, in FIG. 9, the height of the support structure 100 is $L_1$. When one winding 116 of the augmenting 114 is inserted between the windings 108 of the first elongated member 102, as illustrated in FIG. 10, the height of the support structure is $L_1+H_1$. Similarly, when a second winding 116 of the augmenting elongated member 114 is inserted between the windings 108 of the first elongated member 102, as shown in FIG. 11, the height of the support structure 100 is $L_1+H_1+H_1$.

After a desired portion of the augmenting elongated member 114 is inserted between the windings 108 of the first elongated member 102 or the augmenting elongated member is fully deployed, the guide member 140 and the cannula 138 may be removed from the vertebral body 134 and the distraction device support structure 100 distracts the superior and inferior endplates of the vertebral body, as illustrated in FIG. 8. After the support structure 100 has been implanted, bone filler, such as bone cement, bone graft, allograft, autograft, or the like, can be inserted in the resident volume 112 and/or around the support structure using instruments and techniques generally known to those skilled in the art or generally disclosed in the above referenced co-owned patent applications.

It should be recognized from the foregoing description that the use of a system with two elongated members has several advantages. For example, one advantage of a two elongated member system is a potential reduction in the disturbance of tissue as the support structure is formed within the treatment area. In the two member system, the first elongated member requires less windings because the augmenting elongated member augments the height of the support structure. Because the augmenting elongated member increases the height of the support structure, the height of the support structure increases without any further rotation of the first elongated member. Less rotation of the first elongated member potentially results in a reduction in the disturbance of the tissue located in the treatment site.

Also, the use of a plurality of elongated members allows the support structure to be created through a single, relatively small aperture that is significantly smaller than the structure created within the vertebra or disc. The resident volume also allows for the formation of a column of bone tissue/bone cement amalgam that provides further support with a vertebra.

The two elongated member system can have various alternative embodiments and features without departing form the invention. For example, as illustrated in FIGS. 12, 13, 14 and 15, the mating surfaces of the first and augmenting elongating members could have different configurations. In the embodiment of the distraction device support structure 151 shown in FIGS. 12 and 13, the first elongated member 152 includes a top surface 154 and a bottom surface 156. The top surface 154 includes a convex projection 158 extending along the top of the first elongated member 152, and the bottom surface 156 has a rounded or hemispherical cross-sectional shape. The augmenting elongated member 160 includes a top surface 162 having the shape of a rounded groove extending along the top of the augmenting elongated member. The top surface 162 of the augmenting elongated member 160 is configured to mate with the bottom surface 156 of the first elongated member 152. The bottom surface 164 of the augmenting elongated member 160 also includes a rounded groove 166 extending along the augmenting elongated member. The rounded groove 166 of the augmenting elongated member 160 is configured to mate with the convex projection 158 extending from the top surface 154 of the first elongated member 152. Similar to the previous embodiment, the mating of the contoured surfaces can function as a guide that guides the augmenting elongated member 160 between the windings 168 of the first elongated member 152 and can increase stability of the support structure 151. Because of the curvature of the outer surfaces of the devices, as illustrated in FIG. 13, the first and augmenting elongated members also can be mated and advanced through the same rounded cannula simultaneously, if desired.

In an alternative embodiment illustrated in FIGS. 14 and 15, the contours of the top surface 170 and the bottom surface 174 of the first elongated member 172 can be generally V-shaped or chevron shaped. Similarly, the contour of the top surface 176 and the bottom surface 180 of the augmenting elongated member 178 also can be generally V-shaped or Chevron shaped. When augmenting elongated member 178 is inserted between the windings 182 of the first elongated member 172, the top surface 170 of the first elongated member 172 mates with the bottom surface 180 of the augmenting elongated member 178, and the bottom surface 174 of the first elongated member 172 mates with the top surface 176 of the augmenting elongated member 178 so that the windings 184 of the augmenting elongated member 178 nest within the windings 182 of the first distractions device 172.

Furthermore, the top surface 176 of the augmenting elongated member 178 can include a rounded projection 186 that mates with a corresponding groove 188 located in the bottom surface 174 of the first elongated member 172 as best shown in FIG. 15. The engagement of the projection 186 and the groove 188 can aid in guiding the augmenting elongated member 178 between the windings 182 of the first elongated member 172.

A further feature illustrated in the embodiment of the first elongated member 172 is that the elongated member includes stress relief region 190 of any suitable shape, such as a region, void volume, region of more flexible material or a lacking material. The stress relief region 190 allow the elongated member to bow radially outwardly when axial pressure is placed on the support structure. Such stress relief regions increase the compressibility and the elasticity of the support structure. These regions can be of any desired configuration and are preferably elongated regions of substantially the same longitudinal extent as the elongated member itself.

It will be understood that this stress relief feature can be added to any of the elongated members disclosed herein. For example, FIGS. 14 and 15 illustrate an embodiment of a elongated member having stress relief regions 190. As an axial force, is placed on the top wall 170 of the device, the stress relief region translates the force to the sidewalls 195 and 197 which bow outwardly. Such translation of stress can aid flexibility to the distraction device support structure and assist the maintaining the general shape of the distraction device support structure when such force is applied to the distraction device.

FIGS. 16-19 illustrate another embodiment of a elongated member system that includes a first elongated member 192 and a augmenting elongated member 194 that define a support structure 196.

Similar to the previous embodiments, the first elongated member 192 comprises a generally elongated member that can be configured to form a distraction device support structure 196 having a dimensional, i.e. vertical, extent as illustrated in FIG. 20. Turning to FIGS. 16, 17 and 19, the first elongated member 192 includes a top portion 198 and a bottom portion 200 connected to each other by deformable sidewalls or webs or connection members 206 spaced along each of the sidewalls. The first elongated member 192 also may include a longitudinal passage 204 extending generally longitudinally along the first member 192. The connection members 206 are biased to hold the upper portion 198 and lower portion 200 of the first elongated member 192 in a relatively tight or adjacent configuration of limited vertical dimensional extent. When the upper and lower portions 198, 200 of the first elongated member 192 are in an adjacent configuration, the first elongated member 192 has a first height of $A_1$ (FIG. 17).

Referring to FIGS. 16, 18 and 19, the augmenting elongated member 194 is an elongated member that can be inserted into and through a longitudinal passage 204 (FIG. 17) extending along the first elongated member 192. The height B of the augmenting elongated member 194 can be generally larger than that of the passage 204 of the first elongated member 192. However, the distal end portion 208 of the augmenting elongated member 194 can be tapered to a size smaller than the passage 204 or otherwise shaped to assist in the initial insertion of the augmenting elongated member 194 into the passageway 204 of the first elongated member 192.

Because the augmenting elongated member 194 has a height of B that is greater than the height of the passage 204 of the first elongated member 192, when the second elongated member 194 is inserted into the passage 204 of the first elongated member 192, the augmenting elongated member 194 contacts and forces the upper and lower portions 198, 200 of the first elongated member 192 apart, and the deformable sidewalls or connection members 206 deform or stretch, to accommodate the separation of the upper and lower portions 198, 200. After the augmenting elongated member 194 has been inserted into the passage 204, the first and second elongated members have a combined vertical dimensional extent or height of $A_2$ (FIG. 19), which is larger than the height of $A_1$.

The deformable sidewalls or connection members 206 retain the upper and lower portions 198, 200 of the first elongated member 192 in a tight or adjacent configuration prior to insertion of the second elongated member 194, and are sufficiently elastic or flexible to allow the upper and lower portions 198, 200 of the first elongated member 192 to separate into a spaced apart configuration upon insertion of the augmenting elongated member 194.

Additionally, augmenting elongated member 194 should be sufficiently rigid to keep the upper and lower portions 198, 200 of the first elongated member 192 in a spaced apart relation. Yet, the augmenting elongated member 194 should also have sufficient lateral flexibility to allow it to transverse through the passage 204 of the first elongated member 192, which is curved when in situ as shown in FIG. 16. In other words, augmenting elongated member should be relatively rigid or nondeformable in a first direction that is generally parallel to the direction of tissue separation and flexible in a plane generally perpendicular to the direction of tissue separation.

In one embodiment, the augmenting elongated member 194 could include barbs, tabs, or protrusions (not shown) spaced along the augmenting elongated member that function as anchors which retain the augmenting elongated member within the first elongated member. As the augmenting elongated member 194 is inserted into the passage 204 of the first elongated member 192, the barbs contact the inside of the first elongated member to prevent the augmenting elongated member from being withdrawn or retracted from the first elongated member. The barbs or tabs are preferably angled or otherwise configured to allow the augmenting elongated member to be inserted into the first elongated member and to prevent the retraction or withdrawal of the augmenting elongated member from the first elongated member.

FIGS. 7, 8, 20 and 21 illustrate methods of deploying the two elongated member system of FIG. 16 within in a vertebral disc. It will be understood that the methods disclosed herein are for illustrative purposes only and that the same or similar methods could be used to deploy the elongated members in vertebra as shown in FIGS. 3-6 or other parts of the body.

Turning to FIG. 20, a guide member 210 (not shown) is deployed into a vertebral body 212 using similar techniques as described above in regard to FIG. 3 with respect to member 143. Referring to FIG. 20, the guide member 210 is inserted through an off set lumen 211 (FIGS. 16 and 17) of the first elongated member 192, and the first elongated member with the upper and lower portions 198, 200 in the tight adjacent configuration is advanced along the guide member 210 through the cannula 214 and into the vertebral body 212. As the first elongated member 192 is advanced along the distal end portion of the guide member 210, the first elongated member 192 take the shape of the distal end portion of the guide member and winds upon itself to form the distraction device support structure 196 having an initial vertical dimensional extent in situ.

Referring to FIG. 21, after the distraction device support structure 196 has been formed, the augmenting elongated member 194 is inserted through the cannula 214 and into the passage 204 of the first elongated member 192 to augment the support structure 196. As the augmenting elongated member 194 is advanced into the passage 204 of the first elongated member 192, the deformable sidewalls 202 stretch or deform and the upper and lower portions 198, 200 move from their tight configuration to a spaced apart configuration, which increases the dimensional extent or height of the structure formed by first elongated member 192. The increase in height of the first elongated member 192 in turn increases the height of the support structure 196, resulting in distraction of the endplates or further distraction of the endplates of the vertebra on either side of the disc space. After the augmenting elongated member 194 has been deployed, the cannula 214 and guide member 210 are preferably removed, leaving the support structure 196 implanted within the vertebral body 212.

Additional Distraction Device Systems and Methods of Use

One embodiment of a distraction device support structure defined by a distraction device 239 is shown in FIG. 22. The distraction device shown in FIG. 22 is comprised by a first elongated member 252, a second elongated member 253 and an augmenting elongated member 255 that cooperatively interacts with the first and second elongated members to increase a dimensional aspect of the distraction device support structure. Keeping in mind that the distraction device may comprise two or more separate members or sleeves, the distraction device is preferably comprised of an elongated members, such as a thread or ribbon, made of biocompatible materials (including metals and polymers) that are suitable for long term implantation into human tissue where treatment is needed. The biocompatible materials may, for example, be calcium phosphate, tricalcium phosphate, hydroxyapatite, polyetheretherketones (PEEK), nylon, Nitinol (NiTi) or any other suitable biocompatible material.

Biocompatible material may also include PEEK with carbon fibers, polyethylenes of low, medium and or high densities, as well as nylons and blends of materials that contain nylons.

During deployment, the elongated members which form the distraction device support structure preferably have a generally linear configuration for insertion into tissue or between tissue layers. When deployed into or between tissue, the elongated members change configuration, preferably by flexing or bending, to a generally less linear configuration to define a distraction device support structure. For example, in FIG. 22, the elongated members 239 can be bent or otherwise configured to form or define a scaffolding, platform or structure of a semicircular shape. In another embodiment shown in FIG. 23, the distraction device 239 forms support structure having an annulus-like shape. The distraction device support structure can serve to actively separate and/or support (or both) opposed tissue layers such as end plates of a vertebrae or opposed end plates of adjacent vertebrae.

The elongated members of the distraction device may include features that add flexibility to the elongated member to assist in bending or changing the configuration of the elongated member from a generally linear configuration to a less linear configuration and vice versa. For example, the elongated member 252 seen in FIG. 24A may include lateral teeth 241 and intermediate slots or indents 242 that aid in relieving stress and add flexibility to the elongated member. When the elongated member is deployed in spinal tissue, the slots may also provide gaps for the introduction of bone graft materials, cements, or pharmaceutical compounds to the spinal tissues.

In some embodiments, the elongated members may also be designed such that the adjacent teeth or other structures on either side of the slot prevent further bending beyond a finite desired angle. In FIG. 25, opposed sides of an elongated member 252 displays two different types of structures. Generally T-shaped members 237 on one side of the member have longitudinal extensions on their outmost edge such that adjacent members almost touch each other, leaving a relatively narrow opening at the mouth the indent or aperture 238 between adjacent members. When the elongated member is bent toward the side having members 237, the longitudinal extensions on adjacent members come in contact and provide resistance to further bending acting as a stop to limit further curvature. In contrast, the teeth or members 241 on the opposite side of the elongated member lack such longitudinal projections and therefore the elongated member can be bent to a much greater degree in this direction before these teeth 241 come in contact with adjacent teeth to limit further curvature. Also, it should be noted that by providing the T-shaped members 237 and intermediate indentations or gaps 238, increased flexibility is provided that allows the elongated member to bend toward the opposite side.

Additional features may be added to enhance or limit the flexibility of the elongated members of the distraction devices, including grooves, slots, channels, and pockets and teeth or other extensions or members of various shapes. The slots, grooves, channels, and pockets may be placed, for example, in a linear pattern or spirally around the body of the elongated member. Through holes or apertures may also assist in providing flexibility as well as serve as lumens for guide wires, or pull wires, discussed later. The placement of a greater number of these features in one region of an elongated member can make that region more or less flexible than other regions of the device with fewer or different flexibility enhancing or limiting features. In this manner select regions of the elongated member will be easier or more difficult to bend or deflect to assist the shaping of device in a desired conformation. Alternatively, the flexibility features can be located uniformly along a segment or the whole of the device to provide regions of uniform flexibility.

Flexibility of first and second elongated members may also be provided by having a greater number of flexibility features on a particular side or sides of the elongated members. For instance, a series of slots on one side of a member can reduce the amount of force required to deflect that the elongated member toward or away from the slotted side. Flexibility of the elongated member may also be achieved or varied by fabricating the device from a combination of materials with different degrees of flexibility. For instance, by located more rigid material on one side of a member, the member may be easier to bend or deflect toward that side. Particularly if the member is preformed into a desired curved in situ configuration and temporarily straightened for insertion, the more rigid material may tend to retain the desired configuration to a greater degree than the other material and form the desired configuration which introduced into the disc or vertebra. Also, the elongated member can have alternating or different sections along its length that are made of different materials having different rigidity.

The presence of side teeth and slots on the elongated members has a potential added advantage. Contact between the teeth and tissue of the disc or vertebra may help to anchor the member in position. For example, contact against the annular wall of the disc or vertebra to prevent device movement in the circumferential direction after implantation.

In another embodiment of the present invention, the elongated members are characterized by an ability to recover from temporary deformation. As noted previously, the elongated member(s) may be pre-set or pre-formed into a desired in situ shape and then temporarily reshaped, such as by straightening, for insertion. In this aspect, for instance, a pre-shaped elongated member may tend to recover its shape more quickly or completely in body-temperature spinal tissue after being in a less curved conformation during shipping and storage inside a deployment cannula. In other embodiments, e.g., due to plastic creep or other material characteristics, the elongated members may not recover their original shape after extended deformation in the cannula, and an external force may be used to shape the elongated member after it is inserted in the cannula. Such external force may be applied, for example, by a guide member such as guide member 140 previously discussed (see FIGS. 3 and 4) or pull wires to be discussed in more detail later.

In some embodiments the deformation of elongated members are constrained in a first axis and allowed in a plane at an angle to the first axis to allow deflection in a different plane. For instance, in FIG. 28 a semi-circular distraction device support structure is shown in a vertebral disc. The support structure is formed by three elongated members, 252, 253, and 255 and is relatively rigid in the direction (e.g., a vertical direction when standing) extending between two tissues layers, i.e. the adjacent vertebra. The distraction device is resistant to deflection in a direction parallel to the longitudinal axis of the spine due to the relative solid, continuous structure of the elongated members along this axis. Consequently, due to the structure of the elongated members 252, 253, 255 forming the distraction device support structure shown in FIG. 28, no deflection or only limited deflection is allowed in the direction of distraction. In contrast, the elongated members are relatively more flexible in the plane perpendicular to the direction of distraction to allow the elongated members to be shaped as desired, such as curved or deflected to conform the shape of the space in which they are implanted.

In certain embodiments the distraction device support structure does not substantially compress under vertical forces the human spine normally endures, such as but not limited to up to about 1000 N. As described earlier this relative rigidity may be provided by the elongated members having a nearly continuous or relatively solid core portion extending along the vertical extent of the structure. For instance, referring to FIG. 24A, an elongated member composed of PEEK with a center core or wall 236, between indents, that is from about 0.5 mm to about 1.7 mm wide will not substantially compress under normal physiological forces, and may even support a vertical force greater than about 3000 N. More particularly the width of the core can be of any suitable size, such as from about 0.7 mm to about 1.5 mm, or from about 0.9 to about 1.3 mm, or from about 1 mm to about 1.2 mm and other ranges. The elongated member as discussed previously can have teeth on both sides, with a center solid core or, as shown in other embodiments, elongated members may have teeth on only one side with a back or side wall providing a core support for vertical forces.

The distraction devices of the present invention may assume a variety of shapes with a radius of curvature ranging from infinite, i.e. a straight line, to about 3 mm or less. Curved distraction devices may span arcs from about 30° to more than 360°. For flexibility, the depth of indents 242 may vary, depending on the width 235 (FIG. 24A) of the elongated member at the teeth adjacent to the indent and the width of the core support between teeth 236. For instance, the width of elongated members at their widest point can be, as an example only, from about 3 mm to about 9 mm. More particularly for spinal application width may preferably but not necessarily, be from about 5 mm to about 7 mm wide. As examples only, the depth of indents for an elongated member with teeth on only one side, a width 9 mm at the teeth, and a core support of 1.5 mm could be about 7.5 mm (9 mm–1.5 mm=7.5 mm). For an elongated member having teeth on two opposed sides with indents of nearly equal depth such as that shown in FIG. 24A, a width of 9 mm, and a core support of 1.5 mm, then the depth of indents on each side would be about 3.75 mm. For an elongated member having different depth of indents on opposed sides such as those shown in FIG. 22, a width of 9 mm at the teeth and a core between teeth of 1.5 mm then the sum of the depth of opposed indents would be 7.5 mm.

The width 234 of indents 242 may also affect the flexibility or degree of flexing permitted. One example of the width to provide sufficient flexibility on the concave side of curved elongated member can be from about 0.5 mm to about 1.5 mm. More particularly width can be from about 0.7 mm to about 1.3 mm, or from about 0.9 mm to about 1.1 mm. This may be viewed as a desired or preferable minimum width, but other widths may also work depending on the procedure and size of the elongated member and other features of such member.

In embodiments used to distract vertebral discs the height of the distraction device support structure $H_d$ in FIG. 33 preferably should be sufficient to restore the disc to its normal height or thereabout, which will depend on the size of the patient and the discs location in the spinal column. The height the support structure can be, for example, from about 5 mm to about 15 mm. More particularly the height can be from about 7.5 mm to about 13.5 mm, or about 9 mm to about 12 mm and ranges therein. For relatively short individuals or children, the disc size and consequently the height of the support structure can be, for example, from about 5 mm to about 7 mm. For relatively tall individuals, the disc height and consequently the height of the support structure can be, for example, from about 9 mm to about 15 mm or greater potentially.

As noted above, the shape of the disclosed distraction device support structures may be assisted, controlled and/or adjusted as the elongated members are being deployed between the tissue to be distracted. The forces required to control the shape of the disclosed elongated members are compatible with typical hand-held delivery systems and tools. For instance, the shape of the elongated member may be controlled with pull wire systems deployed either inside the elongated member(s) and/or outside the elongated member(s). The shape of the elongated members of the present invention may also be controlled with guide-wires such as pre-shaped nitinol wires, such as guidewire 140 described earlier. The disclosed elongated members may also be shaped with flexible or curved screws inserted into the elongated members. The disclosed elongated members may also be shaped with flexible or curved rods in combination with a geometric pathway. The elongated members disclosed herein may also be pre-shaped such that the device returns to a shape that is identical or similar to its original shape after being straightened or curved to allow delivery to spinal or other tissues through a cannula. In some embodiments, the shape of the elongated members disclosed in this invention may alter in response to a change in temperature or electrical current, such that insertion into the tissue, e.g. spinal tissue, will result in the device assuming a more desired conformation. The various mechanisms disclosed herein for control of the shape or deformation of elongated members of the present invention may be used separately or in combination such that more than one control mechanism may be used to determine the shape and/or location of distraction device support structure in situ.

The elongated members of the present invention may be manufactured using a number of techniques including machining or milling techniques. Milling can include cutting elongated members from solid blocks or rods of PEEK or other suitable material. Elongated members may also be manufactured using molding techniques. Molding techniques include co-molding various materials together to form a elongated member, as well as molding a second material over a first material. Elongated members may also be manufactured by injection molding or extrusion processes. In addition the elongated members of the present invention may be manufactured with Electrical Discharge machining process and by rapid prototyping methods including fused deposition modeling (FDM) and stereo lithography (SLA) techniques]

Elongated members manufactured from polymeric materials such as PEEK may be pre-shaped by placing the elongated member in a metal fixture or jig having a desired shape, such as a semicircular shape, and then heating the elongated member to relieve the bending stress. For instance the elongated member can be treated for about 5 minutes at about 160° C. For many polymeric materials such as PEEK the pre-shaping process biases the elongated member toward a desired shape yet still allows the elongated member to be deformed either in the cannula or in situ after the elongated member is inserted into a tissue. In some embodiments, such as where the elongated members are comprised at least in part of PEEK, the elongated members do not shape memory material properties. Consequently, in some embodiments, particularly when PEEK is used, the elongated member does not return to its original shape without the additional application of an external force to shape the member.

As discussed previously herein, the shape, distribution and size of the teeth 241 and slots 242 on the sides of the elongated members 239 can be configured to assist in forming various curved or bent shapes. As illustrated in FIG. 23, the distraction device can be configured in closed structures such as oval-, disc-, rounded corner quadrilateral-, and other rounded corner polygon-like distraction device support structures. Alternatively, the distraction device can be bent or configured in open structures such as semicircular shapes in which the neither the proximal 243 nor the distal 244 end of the device touch another end or other surface of the device.

The distal ends of the elongated members can have chamfer and wedge features to ease the passage of the elongated member through tissue such as bone or disc material. For example in FIG. 22, a chamfer feature 232 is visible on the upper surface of the proximal end of first elongated element.

As illustrated in FIG. 23, in embodiments of the device forming closed structures (i.e. structures defining a complete annulus) the first elongated member can be configured with surfaces 245, 246 that mate or otherwise engage to assist in maintaining the closed structure such as the annulus shape illustrated in FIG. 23. FIG. 24B illustrates an example of such mating surfaces, with a protrusion on one end 245 of the elongated member that fits into a notch like recess 246 on the elongated member. The notch recess 246 is an indentation configured to securely receive the protrusion and is generally shaped to match the shape of the protrusion 245. For instance, a rectangular protrusion may be matched with a generally rectangular indentation, or a ball shaped protrusion may be match with a semicircular indentation. A particular surface 247 of the indentation may be tapered to assist the entry of the protrusion into the indentation.

The distraction device 239 may itself be composed of two or more elongated members, hereafter exemplarily referred to a first member and a second member. The first member may also be referred to as a top member or sleeve 252 while the second member may also be referred to as a bottom member or sleeve 253 as shown in FIGS. 29, 30 and 31. In one embodiment the protrusions and indentations of the mating surfaces of the first and second elongated members mirror each other.

Figure 26:
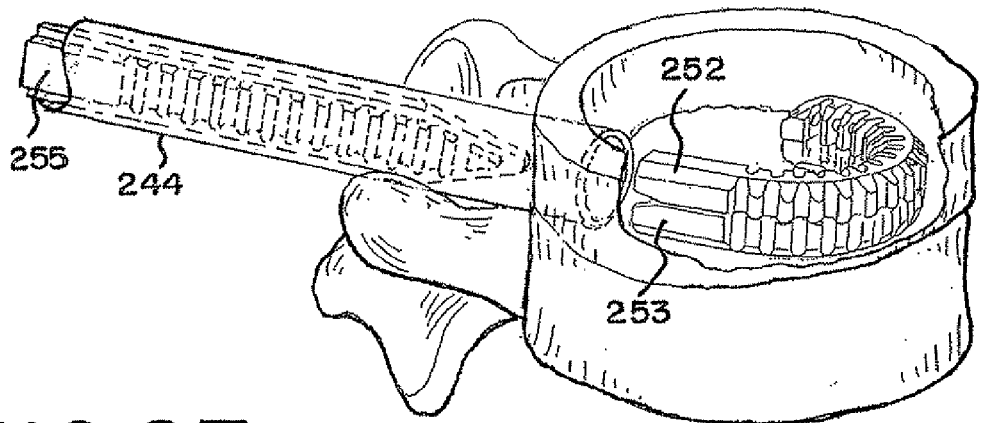
FIG. 26 is a perspective view of a vertebral disc having portions broken away to show the first and second elongated members of the distraction device of FIG. 22 deployed in a vertebral disc and the augmenting elongated member in a delivery cannula.

Turning to FIG. 26, in one embodiment, a first distraction device 240 comprised of a first elongated member 252 and second elongated member 253 can be comprised of a shape memory material that naturally has the configuration of the distraction device support structure in situ. For instance, to deploy a first distraction device 240 that is naturally shaped into a semicircular support structure, the elongated members are forced into a linear configuration, such as in a cannula 284, and inserted between the tissue layers in a generally linear configuration, typically through the cannula 284.

Because of its shape memory properties, the elongated members transforms from a generally linear configuration to their natural semi-circular, or annular or coil-like configuration to define the distraction device support structure upon insertion between tissue layers. The shape memory material used in elongated members optionally includes materials that are shaped into a particular configuration using an annealing process such disclosed in the co-owned patent applications referenced herein.

As seen in FIG. 23, the distraction device support structure 240 may include or define an innerspace or resident volume. As used herein, "resident volume" refers generally to a structural characteristic of the support structure. The resident volume is a volume that is generally defined by the distraction device support structure. The resident volume is not necessarily a volume completely enclosed by the distraction device support structure and can be any volume generally defined by the distraction device. This term does not necessarily mean that the resident volume is an open or void volume or cavity and does not preclude a situation in which the resident volume is, at some point in time, filled with another material, such as bone graft, cement, therapeutic drugs or the like. It also does not preclude the resident volume from containing undisturbed human tissue that is located or remains within the resident volume during or after deployment of the distraction device, as will be explained in more detail below. For example, if the distraction device is employed to separate adjoining soft tissue layers, such as subcutaneous fat and underlying muscle tissue, the resident volume of the distraction device support structure may be hollow or void of tissue after separation. On the other hand, if inserted into a vertebra having cancellous bone tissue therein, the resident volume will contain undisturbed bone tissue, and no void or cavity is formed by the distraction device. Similarly, if inserted into a spinal disc, the resident volume may contain undisturbed disc tissue such as a portion of the nucleus pulposus or bone graft material placed before or after installation.

Figure 27:
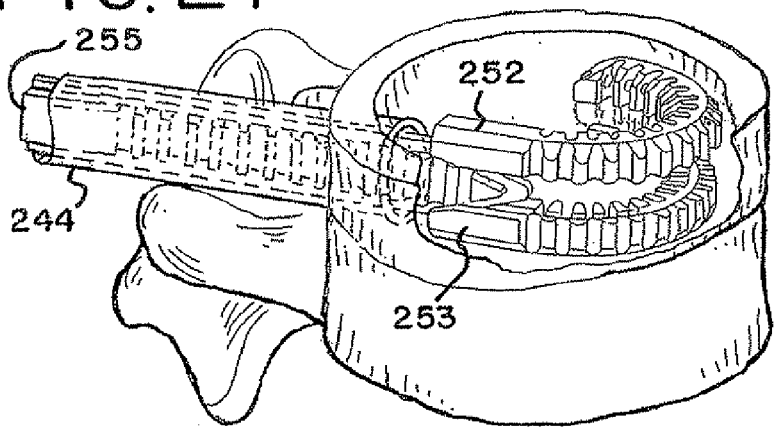
FIG. 27 is a perspective view of a vertebral disc having portions broken away to show the use of a cannula to deploy the augmenting elongated member in a vertebral disc between the first and second elongated members to augment the support structure of the device.
Figure 28:
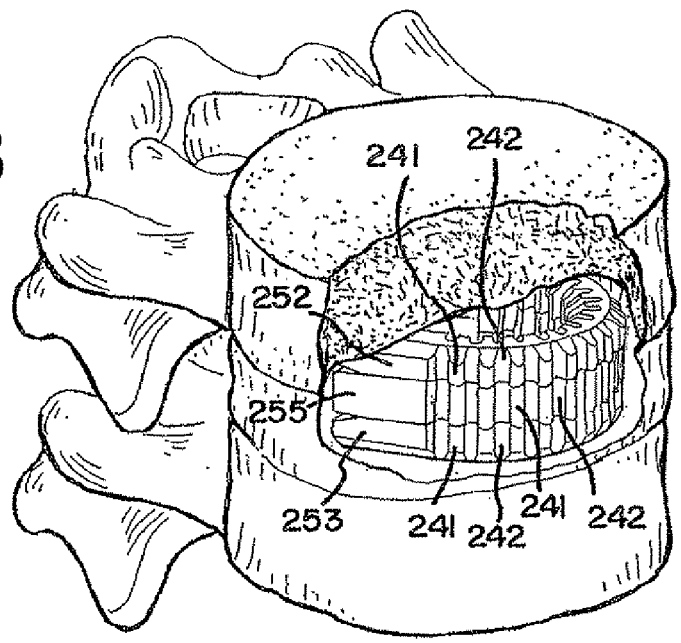
FIG. 28 is a perspective view of a vertebral disc between two vertebra having portions broken away to show an augmenting elongated member fully deployed between the first and second elongated members in a vertebral disc causing the first and second elongated members to contact and distract the vertebra above and below the disc.
Figure 42:
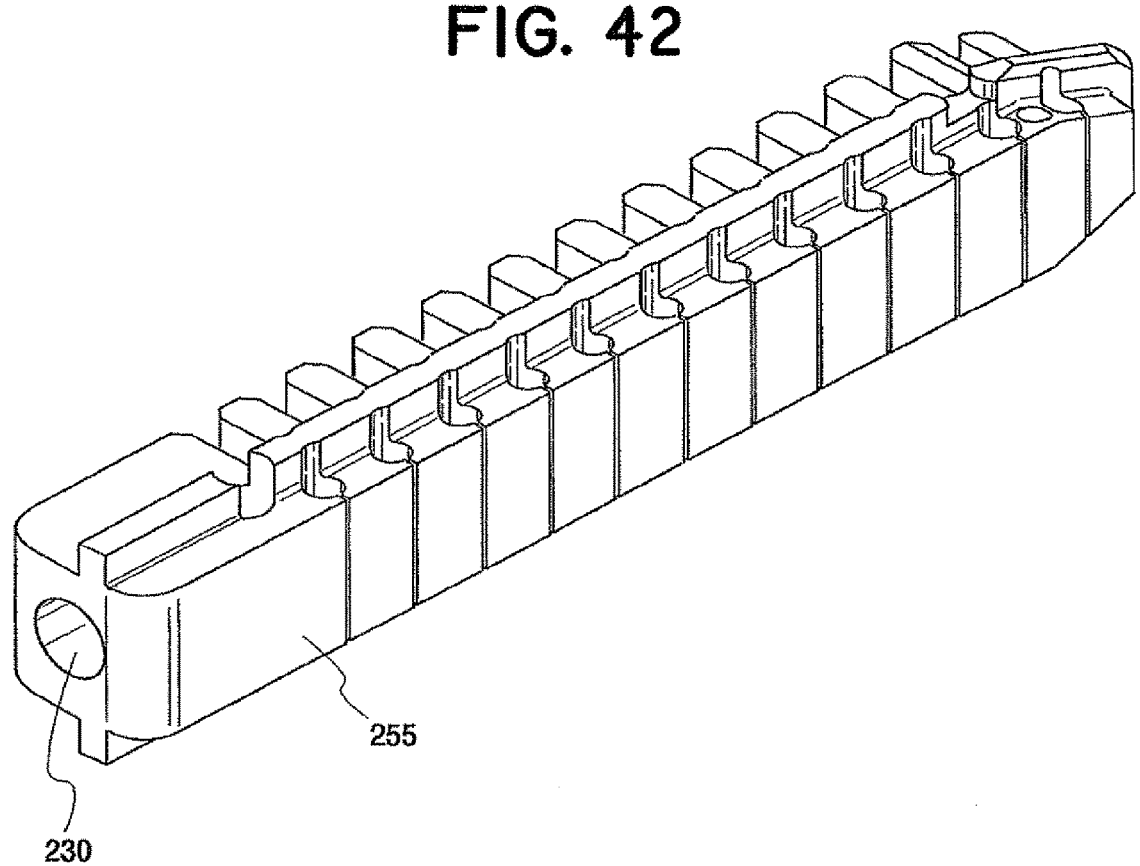
FIG. 42. is a perspective view of an augmenting elongated member having a recess in its proximal end which interacts with a delivery device plunger.

As illustrated in FIGS. 27-29, the first distraction device, composed of first and second elongated members, may be used alone or in conjunction with a second distraction device 255 or spacer hereafter exemplarily referred to as an augmenting elongated member that operatively cooperates with the first 252 and second 253 elongated members of the first distraction device in order to augment the distraction device support structure. The augmenting elongated member 255 preferably comprises a generally elongated member made from biocompatible materials and as shown in FIGS. 30 and 33 may have any of various additional features or aspects such as teeth 241 and slots 242. In the embodiment illustrated in FIGS. 27 and 28, the augmenting elongated member operatively cooperates with the first and second elongated members such that the augmenting member 255 is inserted and slides between the first elongated member 252 and the second elongated member 253 to increase the height of or otherwise augment the distraction device support structure. The degree of height increase of or other augmentation of the distraction device support structure is dependent upon the height (or width) of the augmenting elongated member. For instance, as illustrated in FIGS. 33 and 34 thicker augmenting elongated member 255 will cause a greater increase the height of the distraction device support structure than a thinner augmenting elongated member. However, once augmented, the height of the distraction device is fixed and is not adjustable or variable. The augmenting member is preferably fixed in position between the first and second elongated members and not removal.

In one embodiment the thickness of the augmenting elongated member 255 can be different along its length to cause different amounts of additional distraction along the length of the distraction device. For instance, the proximal portion of the augmenting member may be thicker (taller) than the distal portion of the augmenting member, then the increase of the height of the proximal portion of the first device will be greater than the augmentation of height for the distal portion of the device. The ability to create a greater increase in height in one region of a distraction device allows for adjustments in the curvature of the spine of a patient. For instance, a collapsed disc in the lumbar region of the spine can result in the loss of the normal lordosis in the lumbar region of the spine. The insertion of a augmenting elongated member 255 of variable thickness in a distraction device installed in a collapsed lumbar disc can restore the lumbar disc to the more normal morphology of a greater height on its anterior region as compared to its posterior region—in that situation, the augmenting member may have a greater height its central region between the distal and proximal ends than at either the proximal end or distal end.

In addition to different thickness or height of the augmenting member, either or both of the first or second elongated member can also be made to have different thickness at different locations, such as by altering the surfaces of the first and second elongated members to match the lordotic angle in the device final configuration. For example, if the device is to be deployed in a semi-circular configuration (see FIGS. 45-46) with the middle of the length of the elongated members placed at the most anterior portion of the disc space, the height of the proximal and distal ends of the first and second elongated members could be tapered gradually down to match the desired lordotic angle. In addition to such tapering, a single or multiple thin/small profile protrusion(s) matching the normal max device profile running along the length can be left on the tapered upper or lower faces of the first and second elongated members. These protrusions may act to stabilize the first and second elongated members inside the cannula during deployment, but once implanted inside the disc space, the thin/small profile protrusions would preferentially subside until the tapered outer surfaces of the first and second elongated members are supporting the lordotic face of the endplates.

The first 240 and second 255 elongated members may have corresponding contoured surfaces or features that mechanically or frictionally co-operate or mate to assist in maintaining the positions of the first and second elongated members relative to each other and to increase the stability of the support structure. As noted earlier, it should be noted that the references to "first" and "second" distraction devices is for convenience in the written description. They are combined to provide a single distraction assembly or structure of selected distraction height, and the assembly is not limited to only two "devices" or to only three "sleeves" or "members." In keeping with the broader aspects of the present invention the specific number of "devices" or "sleeves" or "members" can be varied according to the intended usage or design considerations.

As illustrated in FIGS. 29, 30 and 31 the first distraction device has a first elongated member 252 that includes a top surface 256 and second elongated member 253 that includes a bottom surface 258. To increase traction against tissue and reduce the chances for slippage or movement, the top surface of the first elongated member 256 may include tissue-engaging structures, such as intermittent, spaced apart protrusions 266 including ribs, teeth or textured surface or the like and the bottom surface of the second elongated member 258 may also include similar protrusions 267. In some embodiments an individual protrusion may extend substantially along the top surface 256 of the first elongated member, and an individual protrusion may extend substantially along the bottom surface 258 of the second elongated member. In other embodiments as shown in FIGS. 22 and 36 an individual protrusion may be elongated bars that extend laterally along the top surface of first elongated member and the bottom surface of the second elongated member.

The bottom surface 257 of the first elongated member 252 240 may contain a contoured surface 262, while the top side 259 of the second elongated member 253 240 may also be contoured 263, as shown in FIGS. 31, 32, 33, and 33. The augmenting elongated 255 member also may include a top contoured surface 265 or and a bottom contoured surface 266. As illustrated in FIGS. 32 and 33, the top surface 264 of the augmenting elongated member may include a protrusion raised or rib 265 that is configured to mate with an indentation or slot 262 in the bottom of the first elongated member 252. Alternatively, the top surface of the augmenting elongated member may include an indentation or that is configured to mate with a protrusion or rib on the bottom surface of the first elongated member. As illustrated in FIGS. 33 and 34, the bottom surface 266 of the augmenting elongated member may include a protrusion 267 or a groove 268 that is configured to mate with a groove 263 or a protrusion 269 included in the top surface 259 of the second elongated member of the first distraction device 240.

As shown in FIGS. 33, and 34, the cooperation between the protrusions and grooves in the interfacing surfaces between of the elongated members also can function as a guide or guide track that directs the augmenting elongated member 255 between the first 252 and second 253 elongated members. As seen in FIGS. 29, 30 and 36, the entrances to grooves 262, 263 of the first and second elongated members can also be ramped 274 to provide a larger opening on the proximal ends of the grooves to ease the entry of a tapered 273 distal end of augmenting 255 member between the first and second elongated members. Furthermore, the elongated members may have additional mating or guiding surfaces extending from either sides of elongated members which provide added stability to the resulting support structure.

In an embodiment illustrated in FIG. 49, the first elongated member 252 may have projections 270 along the bottom surface 257. Similarly, the top surface 259 of the second elongated member 253 may also have projections 271. The projections 270, 271 on the bottom of the first elongated member and the top of the second elongated member may be shaped to define internal threads or thread segments. The augmenting elongated member 555 may also have projections 272 along its external surface that are configured as external threads. The protrusions 272 on the surface of the augmenting elongated member can cooperate with the protrusions 270, 271 on the first and second elongated members to allow threading advance of the augmenting member between the first and second members. Threading the augmenting elongated member 255 between the first 252 and second 253 elongated members can separate the first 252 and second elongated members 253 to augment the height of the distraction support structure. Using a threaded arrangement also provides a mechanical advantage that may also assist in overcoming internal friction and ease the insertion of the augmenting member between the first and second elongated members As illustrated in FIGS. 29, 30, and 49, the distal end 273 of the augmenting elongated member may have a smaller or tapered cross-sectional area that assists in initiating the insertion or threading of the augmenting elongated member 255 between the first and second elongated members. As shown in FIG. 49, the proximal end 243 of the first and second elongated members of the may have an outwardly tapered regions 274 extending in from the proximal end 243 of the first and second elongated members along the interface of the first 252 and second 253 elongated members. These outwardly tapered regions on the proximal ends of the first and second elongated members form an enlarged receiving region that may assist in aligning the elongated members and in initiating the threading of the augmenting 255 elongated member between the first 252 and second 253 elongated members.

For rotating the augmenting member 255 to thread it into position, the proximal end 276 (FIGS. 50-53) of the augmenting elongated member may contain either a protrusion 277 or a recess 278 shaped to secure the interaction of the augmenting elongated member with a torque delivery tool. A wide variety of shapes can be used to facilitate the interaction of the augmenting elongated member and the torque delivery device, for example in FIGS. 50-53 Philip's-, square-, and star-type endings are shown. These shapes are shown for illustrative purposed and the use of other shapes (oval, diamond, triangle, hexagon, octagon, polygons etc, as well as sets of two or more protrusions or recesses) to secure the interaction of the torque tool and the proximal end 276 of augmenting elongated member fall within the scope of this disclosure.

To insert the distraction assembly into an intervertebral disc, an access port is made through the annulus of a disc using instruments and endoscopic or minimally invasive procedures generally known to those skilled in the art or described in the above referenced co-owned patent applications. Optionally all or a portion of nucleus pulposus is removed and the endplates of the adjacent vertebra are scraped to cause bleeding and promote the fusion of bone graft material to the vertebral endplates. Sizing paddles or like apparatus, may be slipped through the access port to determine the minimum disc height. A cannula 254 is then employed to advance a guide member, such as the illustrated delivery wire 279 of FIG. 47, through the access port and into the intervertebral disc. The guide member 279 is preferably comprised of a shape memory material, such as Nitinol or other suitable shape memory material, such as a shape memory polymer, that has a natural or pre-set shape, for example, the illustrated annulus or semicircular configuration. As the guide member is advanced through the cannula 254, the cannula constrains the guide member into a pre-deployed configuration, generally an elongated linear configuration, allowing an easy and minimally invasive deployment of the guide member into the treatment site. Because of the shape memory properties, the guide member will return to its natural curved-shape or deployed configuration once the constraint is removed, i.e., as the distal end of the guide member 281 exits the distal end portion of the cannula 254 and enters the disc. The guide member 280 can be advanced through the cannula 254 manually or with the aid of an advancing mechanism, such as the advancing mechanisms described in the above referenced co-owned applications.

The guide member 279 is advanced and deployed into the disc, typically along the inner wall of the annulus fibrous, however, depending on the nature of the repair, other paths may be selected for the guide member. Advancement of the guide member 279 is halted when the guide member forms the desired closed (e.g., rounded polygons and annular) or open structure (e.g., semicircular) structure. Depending on the desired procedure, the guide member 279 itself may function as a distraction device, separating adjacent vertebrae. As illustrated in FIG. 47, for example, the first and second elongated members 252 and 253 are inserted over the guide member 279. The first and second members may have facing surfaces that cooperate with the augmenting member or with each other. Referring back to FIGS. 29-34 for examples of this, a slot or groove 262 may be provided in the bottom of the first elongated member 252 and a slot or groove 263 the top of the second elongated member 259, and the guide member maybe configured to fit in one or both of these grooves. In addition as discussed herein, these grooves 262, 263 may also serve as guides for the insertion of the augmenting elongated member 255 between the first and second elongated members 252, 253. Alternatively separate guidewire lumens 282 and 283 may be provided in the first and second elongated members, and they may be inserted by passing them over separate guidewires or members.

To advance the elongated member, as illustrated in FIGS. 35 and 37, a pusher member, for example a plunger 297 can be placed over the guide member behind or proximal to the elongated members. The pusher member is employed to contact and advance the first members forward or distally over the guide member and out of the distal end portion of the cannula. As the first member(s) are advanced forward (distally) over the guide member, the guide member directs them out of the distal end portion of the cannula and into the intervertebral disc.

Turning back to FIG. 47, in the intervertebral disc, the pair of first and second elongated members (sometimes referred to as the first distraction device 240) in FIGS. 29-41 and 47-48 follows along the distal end portion 279 of the guide member and may be shaped by the guide member to form the desired open or closed (or other) shaped distraction device support structure. Although not required, the teeth 241 and slots 242 of the elongated members, as described earlier, enhance the flexibility of the device and assist in its ability to follow the contour of the guide member 279.

As shown in FIG. 47, the first and second elongated members 252, 253 may be advanced over the guide member 279 until the proximal end portion 243 of the first and second elongated members exit the distal end portion of the cannula 284. While the guide member 279 retains the proximal end portion 243 of the first and second elongated members in alignment with the distal end portion of the cannula 284, the augmenting elongated member 255 may be advanced over the guide member and through the cannula 254 and positioned so that the distal end of the augmenting elongated member (which may be tapered or contoured) aligns and mates with proximal surfaces of the first and second elongated members 252, 253 as discussed herein. Alternatively, the first and second elongated members 252 and 253 and augmenting elongated member 255 and the cannula 254 may be configured so that the first and second elongated members and augmenting elongated member can all reside in the cannula at the same time, and then all three members may be advanced through the cannula simultaneously, until the proximal end portion of the first and second elongated members reside in the distal end portion of the cannula 284 as the augmenting elongated member 255 is inserted between the first and second elongated members 252, 253. As illustrated in FIG. 35, the distal end of cannula 284 may have cutouts 285 to allow the cannula to restrain first and second elongated members in one direction, while simultaneously allowing augmentation of the height of the first device 240 (i.e., the first and second elongated members) in a second dimension when the augmenting elongated member 255 is inserted between the first and second elongated members 252 and 253.

Returning to FIG. 47, as the augmenting elongated member 255 is advanced out of the cannula 254, the augmenting elongated member may be directed by a guide member 279. As seen in FIGS. 47 and 48, the augmenting member may have a lumen 286 which allows the augmenting elongated member 255 to be loaded on the same guide member 279 as the first and second elongated members 252, 253. Advancing the augmenting member along the guide member 279 directs it to a location between the first and second elongated members. As previously discussed herein, the augmenting elongated member can have a tapered or otherwise configured distal end portion to aid in the insertion of the augmenting member between the first and second elongated member 252, 253.

In yet another embodiment illustrated in FIGS. 54-60, the augmenting elongated member may be a comprised of a plurality of separate segments 287 instead of being a continuous member. When comprised of separate segments, the augmenting member readily follows and conforms to the shape of the first and second elongated members in situ. The segments of the augmenting elongated member may contain top and/or bottom contoured features such as grooves or protrusions that allow the segments to interact with or cooperate with protrusions or grooves in the facing surfaces of first and second elongated members. As discussed previously herein and shown in FIG. 54, an augmenting elongated member comprised of segments 287 may contain a lumen 288 through each segment, which lumen is loaded over a guide member 279 to facilitate the insertion of the segments 287 of the augmenting elongated member between the first 252 and second 253 elongated members. The height of the segments 287 comprising the augmenting elongated member can be different such that different regions of the resulting distraction structure provide different amounts of height augmentation. As noted above, this ability to control the height of the various regions of the support structure allows the correction of abnormal curvature of the spine for instance by selectively increasing the height on a particular side of intervertebral disc or a vertebral body.

Also, the facing surfaces to segments can be contoured to interact with the adjacent segments of the augmenting elongated member. As illustrated in FIG. 54, for example, the segments may possess opposed concave and convex adjacent surfaces such that a proximal 290 concave surface on one segment contacts and cooperated with a convex distal 289 surface of the adjacent segment. For illustrative purposes, a few examples of segment shapes which allow segment interaction are shown in FIGS. 55-60. In addition to sliding or pivoting contact, adjacent segments may also have interlocking features.

After a desired portion of the augmenting elongated member is inserted between the first and second elongated members, the resulting distraction device support structure distracts the intervertebral disc. At that point, the introducing cannula and guide members, if any, may also be removed. After the support structure has been implanted, bone filler, such as bone cement, allograph, autograph or the like, can be inserted in the resident volume and/or around the support structure using instruments and techniques generally known to those skilled in the art or generally disclosed in the above referenced co-owned patent applications. Alternatively, the bone filler can be inserted into the disc space after measuring the disc space and before the introduction of the distraction structure.

In another embodiment the shape of the first and second elongated members can be controlled during insertion, by applying a greater force to one side of the elongated members than is applied to the other side. The application of unequal force can cause the elongated members to curve in a particular direction. For example, FIGS. 39, 40, and 41 show a system with a pull wire 291 that passes through both the top 252 and bottom 253 elongated members. The pull wires 291 may pass through a wire lumen 282, 283 of each top and bottom elongated members like those shown in FIGS. 31 and 39 or, alternatively, through a wire channel or slot that is not fully enclosed. Pull wire 291 may be a single wire or multiple wires and may be of any flexible material that can be used exert a force along the length of the elongated members 252, 253, 255 and include steel, Nitinol, fiber both synthetic and natural, or the like. In the examples shown in FIGS. 39, 40, and 41 the pull wire 291 is on the left side of the elongated members 252, 253 (as viewed from the proximal end) and an exertion of force, a pull on the wires, will cause the elongated members to curve to the left in the direction of the pull. Alternatively, systems in which a push, an extension force, applied through a rigid pusher could be provided to a elongated members to cause the elongated members to curve in the opposite to the direction of force application.

Systems such as those shown in FIGS. 39, 40, and 41 which include a pull wire or wires 591 that pass through both the first 252 and second 253 elongated members also tend to prevent the first and second members from separating during deployment into the spinal tissue. The use of pull wires 291 (and particularly a single pull wire) in both members also allows pull force to be exerted to maintains the position of the first 252 and second 253 elongated members together within or adjacent to the distal end of the cannula 284 while the augmenting member 255, is being inserted between the first 252 and second elongated member 253. In other embodiments, a pull wire 291 may only pass through one of the first 252 or second 253 elongated members to control the shape and placement of the first and second members. A pull wire 291 or wires may also be used to control the shape and placement of the augmenting member, such as member 255 in FIGS. 25-30, by passing the wire through a lumen that extend longitudinally through the augmenting member.

Imaging techniques, including X-ray, allow real-time and near real-time monitoring of the location and curvature of distraction devices during surgery and systems which apply an unequal force to the first and second elongated members 252, 253 also allow fine control with visual confirmation of the placement and the shape of the first and second elongated members in the spinal tissue. After the first the first and second elongated members 252, 253 are placed in the desired location in the spinal tissue and the augmenting member 255 is inserted in between the first and second elongated members 252, 253 to augment distraction, pull wires 291 may be removed by releasing the ends of the wire or wires and withdrawing from the elongated members.

Various devices may be used to apply tension to the pull wires for shaping elongated members. As shown in FIGS. 37 and 38, the force exerted on pull wires 291 and similar devices for delivering a greater force to one side of elongated members may be controlled by a platform 294 or arrangement that is associated with an advancing mechanism 295. A force delivery platform can comprise, for example, thumbknob 293 associated with an advancing mechanism, the plunger body 295 of FIGS. 99a and 99b.

The force delivery platform may contain regions 296 designed to attach pull wires 291. Examples of wire attachment regions include invaginations, slots such as the ferrule nests 294 seen in FIG. 38, as well as clamps, brackets, screws etc. As illustrated in FIG. 38, the thumbknob 293 may have threads 298 that interact with threads 299 on the puller platform 294 such that rotating the thumbknob 293 will adjust the tension of the pull wire 291.

As illustrated, the force delivery platform 292 may interact with the advancement mechanism 295, for example through a keyway 297 as shown in FIG. 38, such that rotation of the thumbknob 293 adjusts the tension on pull wires 291 but does not cause rotation inside the advancement mechanism 295, i.e. the plunger body of the embodiment shown in FIGS. 37 and 38. In addition to thumbknobs 293, the tension on the pull wires 291, or other devices for delivery of a greater force to one side of elongated members may also be controlled by similar tensioning devices that are known to one of skill in the art, such as screw-drives, plungers, gear mechanisms and the like.

The use of pull wires has other advantages also. The insertion of the augmenting elongated member between the first and second elongated members can create a repulsive force that can push the first and second elongated members away from both the cannula of a delivery device and the augmenting member. The force exerted by pull members such as pull wires controlling member curvature, and the force of friction between the surfaces of the first and second members and the surrounding tissues, such as the endplates of the vertebra above and below a disc, can also serve to resist this repulsive force.

In some applications the magnitude of the resisting forces may make insertion of the augmenting member increasingly difficult. For instance, in some embodiments the first and second elongated members do not contact the vertebral plates until the augmenting member is deployed to increase the height of the support structure. Increasing the force on the pull wires that control the curvature of the members to overcome the repulsive force can, if too much force is exerted, increase the curvature of the first and second elongated member. Increasing the curvature of the first and second elongated members can hinder the ability of the augmenting elongated member to translate along the grooves and/or protrusions of the first and second members which form a guide tract for the insertion of the augmenting member. An excessive increase in the force on the pull wires can also cause excessive or undesired curvature of the first and second members.

In one embodiment, an anchoring or tethering system can be used to hold the first and second elongated members aligned with the distal end of delivery cannula while the augmenting elongated member is inserted between these members. The tethering system can include an anchoring or tethering cable which attaches to the proximal end regions of the first and second elongated members and to the proximal end region of a delivery device. The attachment can be a cable or line that provides little resistance to the deployment of first and second elongated members, permitting the members to exit the distal end of cannula. However the length and tension of the anchor cables or tethers are adjustable to provide increased tension after the first and second elongated members have exited the cannula. The tethers keep the first and second elongated members in close proximity to the distal end of the cannula allowing the insertion of the augmenting elongated member between the first and second elongated member without having to increase the tension on the pull wires controlling the curvature of the members.

In the embodiment shown in FIGS. 43 and 44, for example, the tether can be attached to the first and second elongated member by looping the tether to form an attachment or anchor loop(s) which engage with the proximal end regions of first and second elongated members. The free ends of the tether line can be attached to attachment points 323, 324 in attachment wells 327 and 328 located in the proximal end region of the delivery device. The tether lines 320, 321 can pass inside the delivery device including through the delivery cannula of the delivery device. The attachment loops can associate with the elongated members 252, 253 to attach the members to the deliver device by passing through holes in the proximal end region of the elongated members or around engaging surfaces on the elongated members. In other embodiments, the tether lines may also associated with the elongated members by passing through slots, pull-wire lumens or other like features. The tether lines may also associated with various protrusions, teeth, slots on the proximal end region of the elongated members. Additionally, the first and second elongated members can be attached to the delivery device with a single tether line or loop or more than one tether line or loop.

The embodiment shown in FIG. 43 illustrates the use a single tether wire or line to form two attachment loops 320, 321 by passing the wire around a tensioning pin 322 located on the proximal region of the delivery device with each end of the tether attached to separate fixing pins located in attachment wells 327, 328 at the proximal region of the delivery device. After the augmenting member has been deployed between the first and second members, the anchoring loops attaching the elongated members to the delivery device can be released, for instance, by accessing the wire through a channel 325 and cutting the wire. With the tension released, the fixing pins are readily released and one end of the wire can be pulled to remove the wire from the first and/or second elongated members. In other embodiments, the tension on the anchor wire may be relaxed after the augmenting elongated member is deployed, without cutting the anchoring wire, to ease the release of an end of the wire and the removal of the wire from the elongated members.

In the embodiment shown in FIG. 43, the amount of slack in the anchor loops is regulated by regulating tension on the tensioning pin 322. The tensioning pin 322 which is located on a sliding feature 330 to which a tensioning spring 326 is attached. The spring 326 can exert moderate tension on the sliding feature 330 to provide a limited resistance and prevent slack in the anchoring loops 321, 320 while allowing the elongated members to move down and out of delivery cannula 320. When the elongated members have exited the cannula the sliding feature hits a stop, increasing the resistance on the anchoring loops 320, 321 and retaining the elongated members in close proximity to the distal end of the delivery cannula. The tension on the tensioning 322 pin, which can regulate the slack in the anchor loops, may be controlled with a spring 326 such as a constant force spring, or variable force springs, ratcheting mechanisms, winding spools, stretchable cables with a limited final length and the like.

In some embodiments ends of tether lines can be directly attached to the tensioning pin or multiple tensioning pins. In alternative embodiments, tether lines can be attached directly to spool type or ratchet type systems with or without drag adjustment features.

In another embodiment, free ends of tether line can be attached to a single site on the proximal end region of a delivery device, for instance the tensioning 322 pin or a fixing pin. Alternatively, the each free end may be affixed to separate sites on the proximal end region of the delivery device. Tether lines, wires or cables 320 may be attached to the delivery device or elongated members by releasable mechanical features such as screws, clamps, crimps and ferrules and other like means. Cables or wires may also be attached by knotting, gluing or pinching the cable to the delivery device or in some cases the elongated member.

The anchor or tether wire or cable may consist of materials suitable for sterilization and compatible for temporary contact with animal, including human tissue. Metal anchor cables include stainless steel, nitinol, or other suitable metal wires. Nonmetal anchor cables include natural fibers and polymeric fibers including polyethylene, ultra-high molecular eight polyethylene (UHMWPE), Victrex, Pet, or similar medical-grade polymers.

In some embodiments the tether line wire or cable may be wound on a spindle, with the spindle controlling the tension on the tether. The spindle may also limit the total amount of line released to hold the deployed elongated members at the desired location in close proximity to the distal end 334 of the cannula. The tension in tether lines or cables may be controlled by other means such as springs, resilient means, sliding mechanisms, rotating mechanisms, moving mechanisms, pulleys, stretchable lines and the like.

In the embodiments shown in FIGS. 43 and 44 the delivery devices having anchoring mechanisms such as those discussed herein also have pull members that control the curvature of the elongated members. The tension on the pull wires can be controlled independently of the regulation of the anchoring mechanism. For instance thumb screws 329 or thumb knobs 331 can control the tension on pull wires to regulate the curvature of the elongated members. The embodiment shown in FIG. 44 shows a fully assembled support structure with the augmenting elongated member 255 deployed between the first 252 and second 253 elongated members being held at the distal 334 end of the delivery device by anchor cables or wires with the curvature of the device controlled by pull wires, not visible in this view shown in FIG. 44, but comparable to those described above.

Tether and anchor cable or wire systems are also compatible with delivery device utilizing guide members, for example a guide wire, to control the curvature of the elongated members. In a system utilizing a guide wire, the anchor cable system also will hold the first and second elongated members near the distal end of the delivery cannula while the augmenting member is being inserted between the elongated members or between the winding of a single elongated member. After the augmenting elongated member is deployed, the anchor or tether cable can be released and the delivery device removed.

To assist in placement and retention of the distraction structure, as shown in FIG. 61, the elongated members of the implant device, which are radiolucent (or radiotranslucent), are provided with radiopaque markers, so that the elongated members may be aligned in desired orientations by arranging the elongated members such that the radiopaque markers of each elongated member are in a desired orientation relative to the radiopaque markers of the other members of the insert devices. The elongated members of the implant device can be manufactured from radiolucent materials. Examples of radiolucent materials include polyetheretherketone (PEEK) (a preferred material), polyetherketoneketone (PEKK), nylon and ultra high molecular weight polyethylenes (UMPE). The radiopaque markers are produced from material that is visible with X-ray technology i.e.

material that blocks X-rays and is biocompatible. Examples of materials suitable for radiopaque markers include gold, platinum, tantalum, or other biocompatible radiopaque material.

An example of a system of radiopaque markers used to position the elongated members of an implant device in a desired position is shown in FIG. 61. In FIG. 61, the augmenting elongated member 255 is shown as deployed between the upper or first elongated member 252 and the lower or second elongated member 253. The upper elongated member 252 has a proximal 304, an intermediate 303, and a distal 304 radiopaque marker. Similarly, the augmenting elongated member 255 has a proximal 307, an intermediate 306, and a distal 305 radiopaque marker. The second elongated member 253 also has a proximal 310, intermediate 309, and a distal 308 radiopaque marker. In FIG. 61 each of the augmenting 255, first 252 and second 253 elongated members of the implant device is illustrated in the desired orientation relative to the other members when corresponding radiopaque markers of each elongated members, i.e. the distal markers 304, 307, 310, the middle markers 303, 306, 309, and proximal 302, 305, 308, are aligned. For example in FIG. 61 when the elongated members 252, 253, 255 of the implant device are in their desired orientation and the device is observed in a lateral view the proximal 304, 307, 310 markers of the elongated members form a line parallel to the caudal-cephalic axis of the body. Similarly, as shown in FIG. 61 the intermediate or middle markers 303, 306, 309 and distal markers 302, 305, 308 of the properly positioned elongated members 252, 253, 255 form lines that are parallel to each other and parallel to the caudal-cephalic axis of the body.

Other arrangements of radiopaque markers also could be utilized to indicate that the elongated members of an implantation device are in a desired orientation. For instance, the number, size, shape and spacing of radiopaque markers on each elongated member can be varied, with the number of markers varying from elongated members having as few as one marker to as many as about 10 markers. Instead of the radiopaque markers of the augmenting elongated member 255 aligning with a corresponding marker on the first 252 and/or second 253 elongated members(s), proper relative orientation of the elongated members may be indicated by a marker(s) of the augmenting elongated member aligning between two markers of a first and/or second elongated member(s).

Alternatively, proper relative orientation of the elongated members may be indicated when the marker or markers on the augmenting elongated member fall a particular predetermined distance from a marker or markers on the first and/or second elongated members or wherein distinctly shaped markers are aligned or adjacent. Also, the size and orientation of radiopaque markers can be varied to assist in determining the relative position of the first, 252, second 253, and augmenting 255 elongated members of the implantation device. For example, in FIG. 61 radiopaque markers could be of different size. For example, the proximal markers 304, 307, 310 of the elongated members 252, 253, 255 could each be the same size, for example 2 mm in diameter, while the middle markers 303, 306, 309 of the elongated members 252, 253, 255 each a second size, for example 1 mm in diameter, and the distal markers 302, 305, 308 each a third size, for example 0.5 mm in diameter. In this way, a radiopaque marker can be identified by the size of its cross-sectional diameter when viewed from a lateral or anterior posterior view.

The length of markers can be varied as well to assist identifying a particular marker, for instance in FIG. 61 the middle markers 303, 306, 309 of the members 252, 255, 253, could be spaced from the surface of elongated members in this way the markers have a detectable gap between the corresponding middle markers 303, 306, 309 even when the markers are aligned. In contrast, the proximal 304, 307, 310 and distal 302, 305, 308 markers could extend to surface so as to appear to be touching the corresponding proximal or distal marker when the markers are aligned. The orientation of the radiopaque markers 302-310 in the elongated members 352, 353, 355 can also be varied to assist in identifying particular markers. For instance, the cylinder markers such as those illustrated in FIG. 61 can be arranged so that a particular set of markers for example the middle markers 303, 306, 309 are parallel to the lateral axis while the other markers are parallel to the caudal-cephalic axis.

In some embodiments, the shapes of radiopaque markers can also be varied to assist in identifying particular markers. For example, the shapes may be selected such that when viewed in cross-section in a lateral or anterior posterior view using fluoroscopic techniques, the markers appear as circles, triangle, squares, rectangle other polygons, or other identifiable shapes. Utilizing markers of distinctive shapes in known regions of the elongated members allows the surgeon to readily determine the position of each elongated member of the implant device relative to the position of the other elongated members of the device.

In addition to relative alignment, radiopaque markers placed at known locations in the radiolucent elongated members of an implantation device also allows a surgeon to determine the shape and location of the implant device in the disc space. In FIG. 61, for example, the elongated members of an implant device are transparent and the position and shape of the elongated members in the disc space is revealed by the positions of the proximal radiopaque markers 304, 307, 310, the middle or intermediate radiopaque markers 303, 306, 309, and the distal radiopaque markers 302, 305, 308. As an example, in a lateral fluoroscopic view, when the middle or intermediate radiopaque markers 303, 306, 309 are at a more anterior location than the distal markers 302, 305, 308 or the proximal markers 304, 307, 310, it indicates that the structure is a curved orientation in situ. The radius of curvature of the implant device can be determined in part by the anterior posterior view in which the distance between the proximal markers 304, 307, 310 and the distal markers 302, 305, 308 can be determined, with a greater distance between these distal and proximal markers corresponding to a larger the radius of curvature for the insertion device. Increasing the number of radiopaque markers dispersed along the elongated members 252, 255, 253 of the insert device may allow more detailed determinations of the location and shape of implant devices in spinal tissue.

In other embodiments the elongated members 552, 553, 555 of the implant device may be made partially radiolucent by adding a filler to the radiolucent material used to synthesize the elongated members. Partially radiolucent elongated members allow detection of the position of the elongated members without the use of radiopaque markers, but as the elongated members are semi-radiopaque, the device does not completely block observation of adjacent spinal tissue such as the bony fusion between vertebral bodies that forms after a fusion procedure. Material suitable for use as a radiopaque filler includes $BaSO_4$ or $BiO_3$. The weight ratio of radiopaque filler material added to the radiolucent materials to produce a partially radiolucent elongated member may be selected to provide the desired radiolucence, and may range, for example, from about 2% to about 20%. In other embodiments, the percentage of radiopaque filler material will range from about 4% to about 18%, about 6% to about 16%, and about 8% to about 14%. In other embodiments the percentage of radiopaque material will range from about 2% to about 9%.

In some embodiments the first, second, and augmenting elongated members, 252, 253, 255 of an implantation device may interact to form locking mechanisms that interact to interlock the elongated members in a desired orientation relative to the other elongated members of the device. Interlocking mechanisms may be formed by mechanical interfering surfaces on one or more elongated members 252, 253, 255 that lock to one or more elongated members of the implantation device to prevent a elongated member from moving relative to one or more other elongated members of the implantation device. The locking mechanism may assist in preventing the elongated members of implantation device from slipping relative to one another in response to the stresses a patient's normal movements place the implantation device.

One embodiment of a locking mechanism is shown in FIGS. 66 and 67. FIG. 66 shows a second elongated member 253 with an interlocking recess 313 into which a locking protrusion 314 from the augmenting member can enter to lock the augmenting member 255 into a desired orientation relative to the second elongated member 253. Also a locking protrusion 314 on the top surface 264 of the augmenting elongated member may interact with an interlocking recess 313 in the bottom surface 257 of the first elongated member to lock the augmenting elongated member 255 into a desired orientation relative to the first elongated member 252. When fully engaged all three elongated members are substantially locked against relative movement.

The guiding of the locking protrusion 313 into a interlocking recess 313 may be assisted by locating the interlocking recess along a groove or track 263 on an elongated member. As seen in FIGS. 62 and 63, for example, a groove 263 in the upper surface 259 of a second elongated member 253 can act as a guide in which a long protrusion or ridge 267 on the bottom surface 266 of a augmenting elongated member 266 slides distally to its in situ position between the upper or first 252 and lower or second elongated members 253. A locking protrusion 314 on the upper surface of the augmenting elongated member may be cylindrically or otherwise shaped and, as shown in FIG. 62, the diameter of the locking protrusion may be wider than the width of the longitudinal guide protrusions 267, 265 on the bottom and top surfaces of the augmenting elongated member. As illustrated in FIG. 63, interlocking recesses 313 are elongated slots 263 in the first and second elongated members. In addition as shown in FIG. 63, the diameter of the locking protrusion 314 is larger than the narrowest entryway 316 into the interlocking recess 313. Consequently, the locking protrusion 314 can slide into the interlocking recess from a wide entryway 315 but is too wide to pass through the narrow entryway, preventing over-advancing of the augmenting member.

As illustrated the locking protrusion 314 which fits into the interlocking recess 313 may be any suitable size or material, such as a cylinder or pin made of a radiopaque material with a diameter ranging from about 0.25 mm to about 2 mm. As shown in FIGS. 66 and 67, the locking protrusion 314 may extend beyond the upper and lower surfaces of the elongated member in which the locking protrusion 314 is mounted such that once the locking protrusion enters the interlocking recess 313, the locking protrusion 314 extends into the recess 313 and resists the movement of the protrusion out of the recess 313.

Alternatively, the parts may be reversed, and the locking protrusions 314 may be found on the bottom 253 and/or top 252 elongated members and the interlocking recess(es) 313 may be found on the augmenting elongated member 255. Of course, other locking arrangements involving interfering surfaces between the first, second and augmenting elongated members are also suitable.

As illustrated in FIGS. 66 and 67, the lower surface 257 of the first elongated member and the upper surface 259 of the second elongated member may have features such as ramps 275, tapers, or concave indentations to ease the entry of the locking protrusion 214 into the interlocking recess 313. The outer surface of the locking protrusion may also be tapered 317 such that one edge is higher than another edge to allow the locking protrusion 314 easily entry into the interlocking recess 313 but resist the locking protrusion 614 from exiting the interlocking recess 313 by sliding back in the opposite direction from which the locking protrusion 314 entered the interlocking recess 313. The taper 317 of the locking protrusion 314 can also aid the entry into interlocking recess 313.

The maintenance of the position of locking protrusion within the interlocking recess 313 may be enhanced by the geometry of the locking protrusion. For example, FIG. 64 shows a locking protrusion 314 with slots 319 that extend into the protrusion along its top and bottom surfaces. The slot 319 may be compressed as the locking protrusion 314 is being pushed into the interlocking recess 313 to ease entry of the locking protrusion into the interlocking recess 313. Subsequent to entry of the interlocking recess 313, the slotted locking protrusion 314 can expand to result in a tighter fit of the protrusion in the recess to help prevent the locking protrusion from exiting the interlocking recess. Other geometries of the locking protrusions may also assist both the entry and retention of the locking protrusion into an interlocking recess. For instance, FIG. 65 illustrates a locking protrusion 314 that is rounded on one side 320 and flatter 321 on a second side. The rounded side 320 of the locking protrusion 314 may assist the entry of the locking protrusion 314 into an interlocking recess 313, while the flat 321 side can assist in keeping the locking protrusion 314 from slipping out of the interlocking recess 313.

In addition to generally cylindrical shapes, locking protrusions 314 and interlocking recesses 313 can be a number of shapes that ease entry of the locking protrusion into the interlocking recess and subsequent to entry, these same geometries also resist disengagement of the locking protrusion 314 from the interlocking recess 313. Examples of suitable geometries for locking mechanisms include arrow like shapes trapezoidal shapes and other shapes with narrower leading edges and wider trailing edges. In some embodiments an insertion device may have more than one locking mechanisms. In some embodiments, the locking mechanisms whether one or more are only engaged when each elongated member of the insertion device is in the preferred orientation relative to the other members.

To assist the surgeon in positioning the elongated members the mechanical features of the locking device may be contain a radiopaque material. For instance the locking protrusion 314 may be a tantalum pin and the interlocking recess 313 may be lined with tantalum or another radiopaque material.

Miscellaneous Other Features

The various embodiments of the present invention may employ other features to enhance the distraction structure or its method of use. For example, the distal end portion of elongated members can include an angled or sloped first section that has a length that is equal to about the length required for one revolution or to form one winding.

The elongated members of the present invention can also include surfaces that frictionally or mechanically engage each other during and after the formation of the distraction device support structure. The frictionally engaging surfaces can provide several benefits, such as eliminating or reducing movement between adjacent windings of the support structure, providing better rotational movement and transmission of torque during deployment and preventing unwinding or dilation of the windings under axial loading. For example, the elongated members of a distraction device may have frictionally engaging surfaces, knurls, varying thickness in peaks and valleys, and the like.

After the distraction device has been implanted and the distraction device support structure has been formed, the interlocking of the adjacent windings reduced the amount of unwinding or radial dilation that can be caused by axial loading. For example, in some cases, if the adjacent windings are not interlocked, loading or force in the axial direction may cause the top and bottom ends of the distraction device support structure to dilate or unwind. The engagement between the knurls of the top and bottom walls interlocks the adjacent windings, which assists in reducing such dilation.

As discussed above, the elongated members of a distraction device can include teeth and slots or indents that assist in adding flexibility to the distraction device. Specifically, the elongated members may include teeth that extend at an angle from the back wall or a central spine of the elongated member, for example at angles between about 30 degrees to about 90 degrees relative to the spine, with slots or indents therebetween. Because the teeth are angled away from the tissue, the angled teeth slide smoothly past the tissue as the elongate member is inserted, and resist retraction or withdrawal of the distraction device once it is deployed into tissue.

The elongated member of the present invention may include interlocking windings or tiers to form the distraction device support structure. For example, the elongated members may include projections and recesses that are configured to accept the projections when the elongated members are configured to form an interlocked support structure.

The elongated members may include at least one anchor extending from a back wall of an elongated member to contact and in some cases imbed into the cancellous bone surrounding the support structure. When a compressive load is placed on the support structure in the axial direction, the anchor bear a portion of the load, which aids in the support structure maintaining its position within the tissue. Anchoring projections may also be on the surfaces of the elongated members of distraction devices used in vertebral discs for disc repair, replacement or vertebral fusion.

Figure 45:
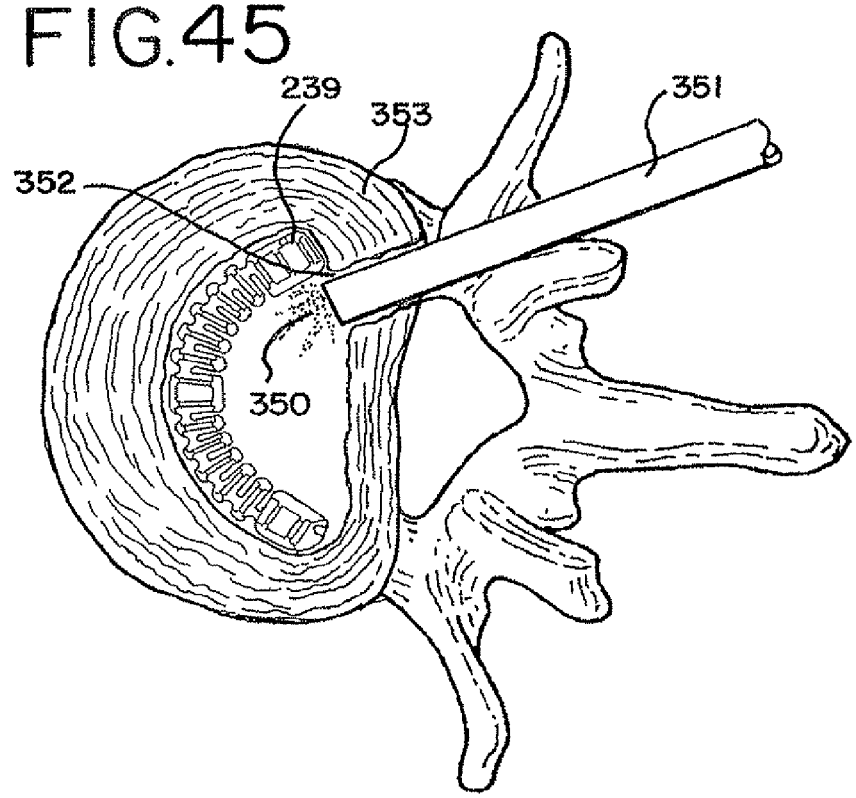
FIG. 45 is a top view of a distraction device deployed in a disc and located adjacent or against the annulus of a disc with a cannula delivering bone graft material.
Figure 46:
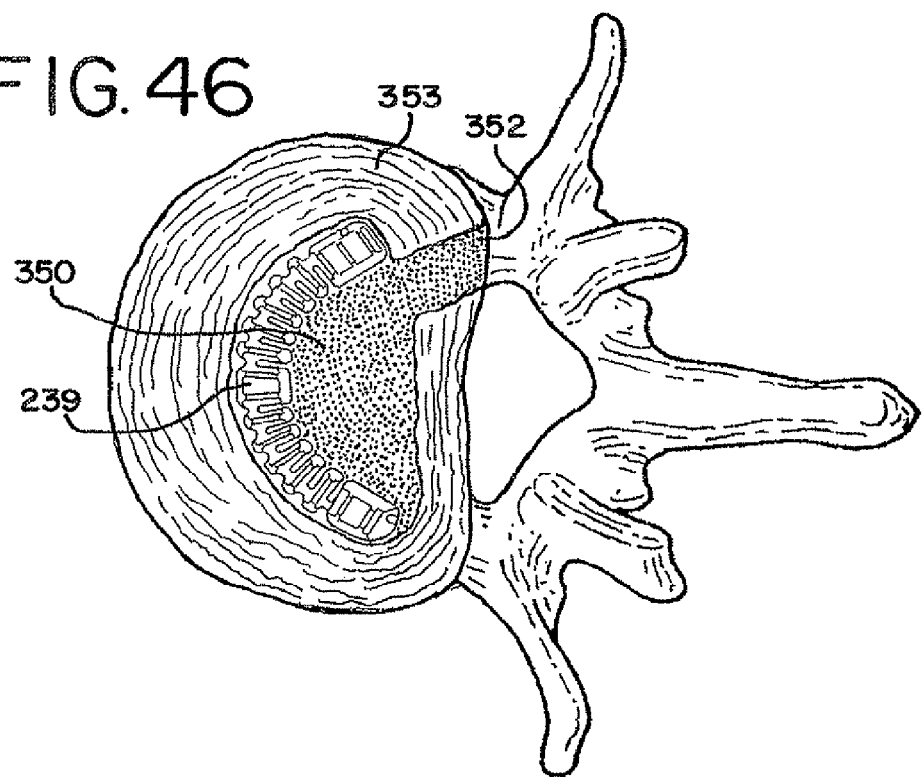
FIG. 46 is a top view of a distraction device deployed in a disc against the annulus of a disc with bone graft material filling much of the disc space including an access opening or aperture in the annulus of the disc.
Figure 68:
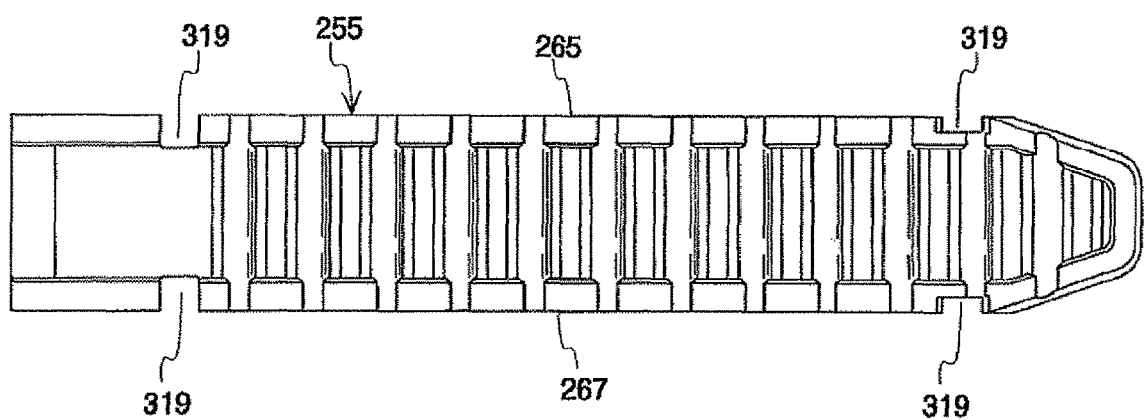
FIG. 68 is a side view of an elongated augmented member with recesses to provide interlocking features.

After the distraction device has been deployed to form the support structure, cement may be injected in and around the distraction device support structure to add stability to the support structure. In other embodiments, for example with a distraction device used to promote the fusion of adjacent vertebra a bone graft material, including allograft, autograft and the like may be injected in the regions in and/or around the distraction device deployed in the disc space. This is illustrated in FIGS. 45 and 46. The embodiment shown in FIGS. 45 and 46 illustrates a flowable material 350 including bone graft material, cements and the like being delivered with a cannula 351 through the same opening 352 in the annulus fibrosus 351 which was used to insert a semicircular distraction device 239. The distraction device is deployed in the disc space and is adjacent the annulus fibrosus 353. In FIG. 45, the flowable material is shown exiting the cannula 351 and entering the disc space, and FIG. 46 shows the same disc with the cannula 351 removed and the disc space including the opening 352 to the annulus filled with the flowable material 350. The flowable material may be delivered by any method known in the art and more particularly equipment used to delivery of flowable material can include the cannula used to insert the distraction device, a specialized cannula, and/or various injection equipment.

As discussed above, elongated members can be deployed into tissue or between tissue layers by advancing the elongated member over a guide member. One method of deploying a elongated member involves incremental deployment of the guide member and one or more elongated members. The incremental method can be used to deploy the elongated member into tissue or between tissue layers at any desired location within the body and is particularly useful in treating spinal tissue, such as vertebrae and intervertebral discs. For example, a portion of the guide member is advanced out of the distal end portion of a cannula and into a treatment site. Next, the elongated member is advanced over the portion of the guide member. The guide member is then further advanced out of the cannula to extend portion of the guide member past the distal end portion of the elongated member, and the elongated member is then further advanced over the guide member. The incremental deployment of the guide member and elongated member continues until the elongated member or members are fully deployed in the vertebral body. Such incremental deployment aids in maintaining the shape of the guide member, in preventing radial dilation of the guide member, and reduces the amount of friction between the guide member and the tissue in which it is inserted.

As further may be used in the present invention the distal end portion of the guide member can be configured to reduce the amount of penetration force required for insertion of the guide member. The guide member can also have other alternative configurations that aid in the guide member's ability to traverse through tissue, including a rotary advance arrangement.

For example, the guide member can include an outer elongated member that has a lumen therethrough. An inner or central elongated member extends through the lumen and past the distal end portion of the outer elongated member. Both the outer elongated member and the inner elongated members can be made of a shape memory material that has a natural coil or spring-like shape. Alternatively, either the outer elongated member or the inner elongated member can be made of a shape memory material.

The above miscellaneous features are described more fully in U.S. application Ser. No. 12/034,853, file on the same day herewith, entitled "Devices For Treating The Spine", and is hereby incorporated by reference.

The present invention has potential application and benefit for both nucleus containment and annulus repair when employed in intervertebral discs. When a spinal disc herniation occurs, the nucleus pulposus of the disc may extrude or bulge through a tear in the annulus fibrous to the outside of the disc. The device and methods of the present invention can be used as a containment device for containing the nucleus of within the disc and to prevent herniation or bulging of the nucleus through the annulus of the disc, as well as for nucleus replacement to replace a dysfunctional nucleus and act as a mechanical support.

For instance, a cannula can be placed through an access port into a disc and a guide member deployed through the cannula into the disc. Utilizing a distaction device with a helical support structure, the guide member can form a coiled or spring-like shape within the disc. In embodiments utilizing a distraction device with a generally annular support structure such as FIGS. 1-6, the guide member can form a generally annular shape. The guide member is preferably sized and shaped to fit between the annulus and nucleus and substantially surrounds the disc nucleus. The deployed barrier encircles the nucleus to contain the nucleus and prevent it from bulging or extruding through the annulus.

With respect to annulus repair, the normal intervertebral disc has an outer ligamentous ring called the annulus surrounding the nucleus pulposus. The annulus binds the adjacent vertebrae together and is constituted of collagen fibers that are attached to the vertebrae and cross each other so that half of the individual fibers will tighten as the vertebrae are rotated in either direction, thus resisting twisting or torsional motion.

Occasionally fissures may form rents through the annular wall. In these instances, the nucleus pulposus is urged outwardly from the subannular space through a rent, often into the spinal column. Extruded nucleus pulposus can, and often does, mechanically press on the spinal cord or spinal nerve rootlet. This painful condition is clinically referred to as a ruptured or herniated disc.

The distraction devices of the present invention described herein also can be used for annulus repair. Instead of treating a herniated disc by enclosing the nucleus, the distraction device can be used to replace or strengthen a damaged annulus. For instance, a guide member or pull wire system can be used to form first and second elongated members into a semicircle shape and deliver said members to the region between the nucleus and a rent in the annular wall. If desired an augmenting member can then be inserted between the first and second elongated members to assist in containing the rent and maintaining the desired placement of the containment device.

Figure 69:
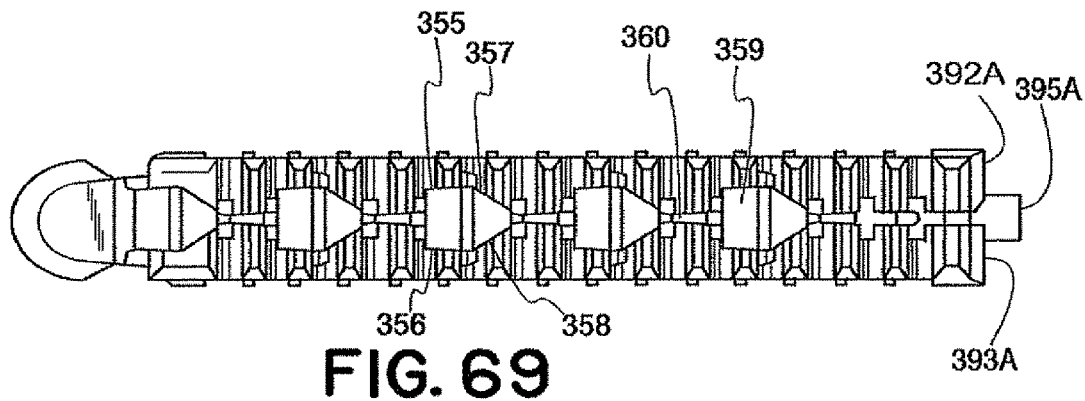
FIG. 69 is side view of a distraction device having spaced apart teeth or spreading members on a first lateral side with the augmenting elongated member in a first position between the first and second elongated members.
Figure 70:
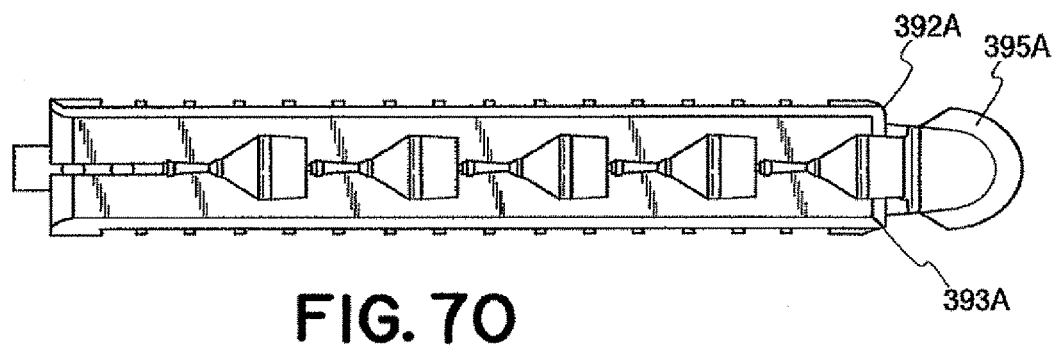
FIG. 70 is a side view of the other side of the distraction device of FIG. 69 lacking spaced apart teeth, and with the augmenting elongated member in a first position between the first and second elongated members.
Figure 71:
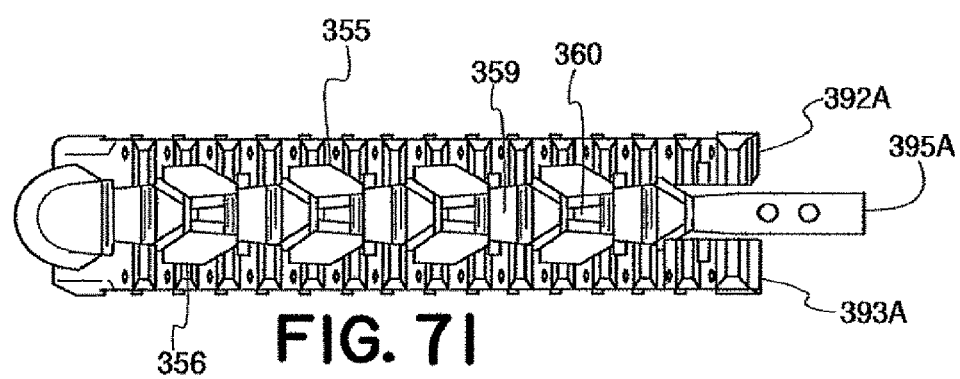
FIG. 71 is a side view of the distraction device of FIG. 69 with the augmenting elongated member in a second position between the first and second elongated members spreading the first and second members apart to increase their dimensional aspect.

FIGS. 69-75 illustrate alternative embodiments of distraction devices embodying aspects of the present invention. As illustrated in FIG. 71, the distraction device includes first and second elongated members 252 and 253 and augmenting elongated member 255. Preferably all three elongated members are pre-assembled for insertion into a spinal disc, vertebra or between other tissue to be distracted. In the configuration shown in FIGS. 69 and 70, the first and second elongated members each have a series of spaced apart recesses 355 that are located to align with a similar recess 356 in the facing surface of the opposing elongated member. When the first and second elongated members are in adjacent face to face position, the facing recesses define a series of cavities each of which has an inclined or tapered, conical-like wall 357, 358 as best seen, for example, in FIG. 69.

The augmenting elongated member 255 includes a series of spaced apart augmenting or separating members 359 which have a shape generally comparable to the shape of the cavities defined by the facing recesses in the first and second elongated members. The spaced apart augmenting members 359 are joined to the next adjacent augmenting member by a relatively thin web of material 360.

In the pre-assembled condition, the elongated augmenting member 255 may be located between the first and second elongated members 252, 253, with the distracting or augmenting members 359 located within the cavities formed by the facing recesses 355, 356. This allows the combined structure of the first and second elongated members and the augmenting elongated member to have a relatively small profile or narrow profile for insertion between the tissue layers to be distracted, such as for insertion into a spinal disc or vertebra. More specifically, the width or height of the combined three member profile is only slightly larger than that of the first and second members alone in a facing relationship. The combined profile is larger than the first and second profile only by the dimension of the thin web of material 360 that connects the spaced apart augmenting members 359 of the elongated augmenting member 255. This construction is best seen in FIG. 69 which shows the assembled three member arrangement.

After insertion between the tissues to be distracted while in the preassembled configuration shown, for example, in FIG. 69, and after forming into the in situ configuration for tissue distraction, whether that be by natural bias of the material itself, or by assistance of a guide member or pull wire, the device can be formed into a distracted condition, in which the upper and lower surfaces of the first and second elongated members are spread apart. The distraction is caused by exerting a pulling force or tension on the center augmenting elongated member. By pulling the augmenting elongated member, the tapered surfaces of the augmenting elements are forced against the mating tapered surfaces of the cavities formed by the facing recesses of the first and second members. This results in a spreading action exerted on the first and second members, forcing them to a spread-apart position as shown, for example, in FIG. 71 where the first and second members 252 and 253 are spread apart by a distance approximately equal to the width of the augmenting members 355 located on the elongated augmenting member 255. In other word, the combined structure shown in FIG. 69 before distraction has a dimensional extent extending between the upper surface of the first member 252 and the lower surface of the second member 253. This dimensional extent would extend generally vertical when inserted into the spine or, in other words, generally parallel to the axis of the spine. That vertical extent is enlarged substantially as may be seen in FIG. 71 when the augmenting member has been pulled or moved to the distracted position shown there, spreading apart the upper surface of first elongated member 252 and lower surface of second elongated member 253.

Figure 72:
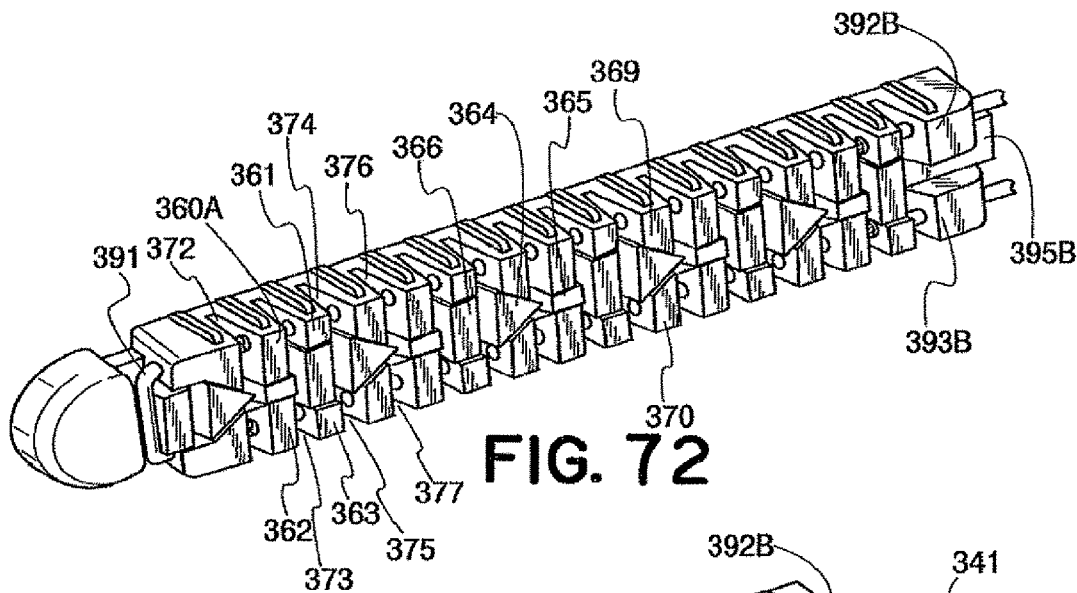
FIG. 72 is a perspective view of distraction device having spaced apart teeth or spreading members on a first lateral side with the augmenting elongated member in a first position between the first and second elongated members.
Figure 73:
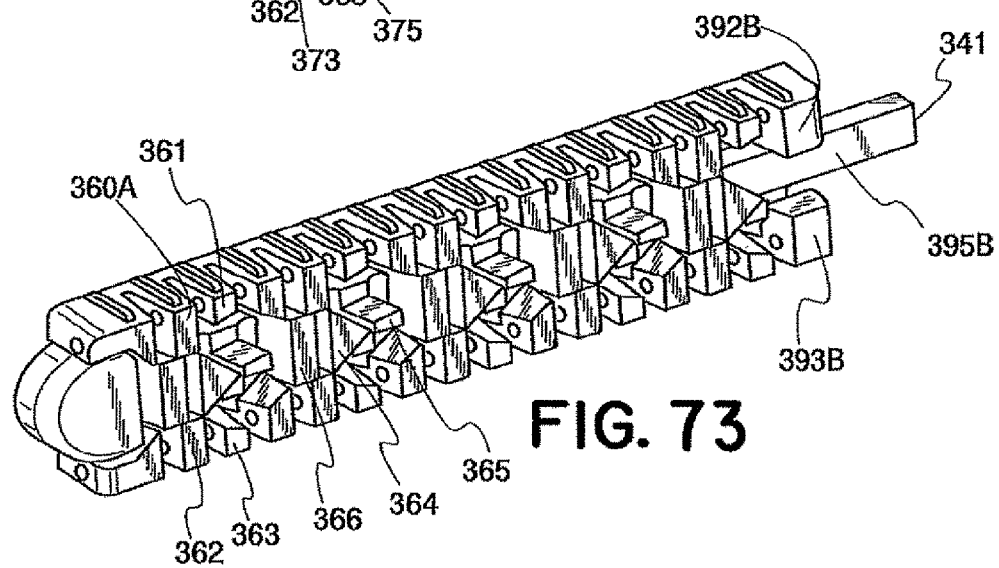
FIG. 73 is a perspective view of the distraction device shown in FIG. 72 with the augmenting elongated member in a second position between the first and second elongated members spreading the first and second members apart to increase their dimensional aspect.

FIGS. 72-76 illustrated an embodiment of the present invention based on a variation of the approach described in connection with FIGS. 69-71, with a somewhat different structure. More particularly the structure of the first and second elongated members and the augmenting elongated members of FIGS. 72-76 define a series of teeth 360, 362, 366 and slots 361, 363, 365 in the combined structure (as shown in FIG. 72 before distraction) that readily accommodates bending or forming by guidewires, guide member or other external force into a semi-circular configuration (see FIGS. 75 and 76).

Figure 74:
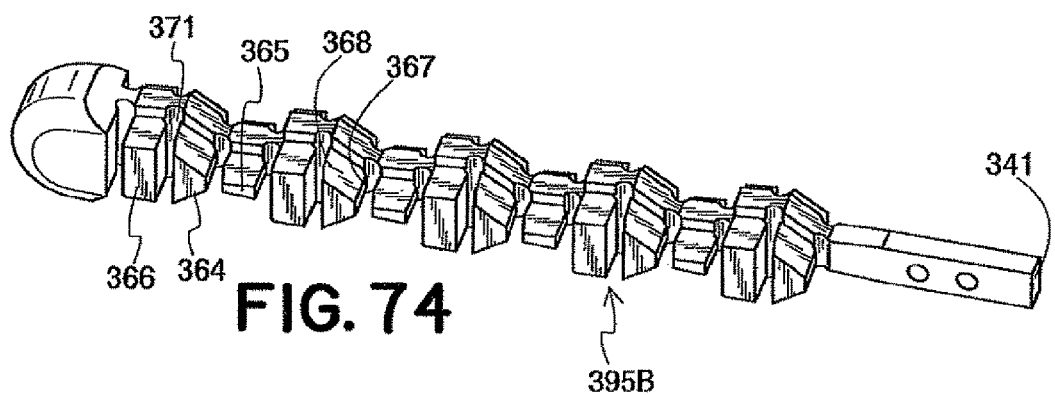
FIG. 74 is a perspective view of the augmenting elongated member of the distraction device shown in FIG. 72.

As best seen in FIG. 72, each of the first and second elongated members 252 and 253 has a series of alternating teeth and slots disposed along one side of the alternating member. The teeth vary in the vertical extent in order to receive and cooperate with mating structures associated with augmenting elongated member, as will be seen more fully in this description and in the drawings. Turning to FIG. 74, which is a perspective view of the elongated augmenting member, it may be seen that the elongated augmenting member includes a repeating series of three elements or structures. The first structure 364 is a tapered member with inclined upper and lower surfaces forming a generally wedged cross-sectional shape, extending from a relatively narrow leading edge 367 to a wider, i.e., higher, trailing edge 368. A second structure element 366 is spaced from structure element 364 by a slot 371. A connecting member 365 is located between members 364 and 366 of adjacent series.

When the augmenting elongated members in the pre-insertion position (before insertion between tissue to be distracted), as shown in FIG. 72, it may be seen that the wedge shaped members 364 are located between facing teeth 360, and 362 of the first and second members, each of which have an inclined surface which generally matches the inclined surfaces of the wedge shaped member. According, when tension or pulling force is applied to the augmenting elongated member, the interaction between the tapered surfaces of the augmenting members 364 and the inclined surfaces of the teeth 369, 370 on the first and second elongated members forces the first and second elongated members apart, spreading them to the position shown in FIG. 73, in which they are spread apart approximately by a distance equal to the width the trailing edge 369 of member 364. Because the series of wedged shaped members and other members on the augmenting elongated member are separated by slots, flexibility is enhanced and the structure created between the tissues is allowed to an assumed and retain a curved configuration, such as shown for example in FIGS. 75 and 76.

Figure 75:
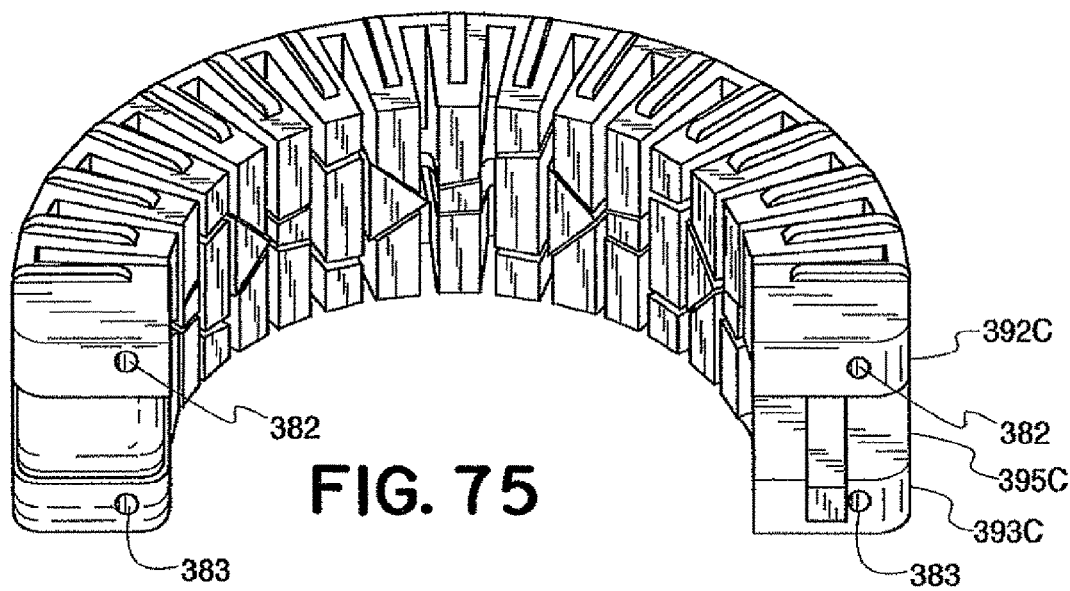
FIG. 75 perspective view of the distraction device shown FIG. 72 in a curved configuration as it may be configured in situ, with the augmenting elongated member in a first position between the first and second elongated members, the device having a dimensional aspect (e.g., the distance between the upper and lower surfaces of the device) that extends in a direction between two facing tissue layers (not shown) when in situ.
Figure 76:
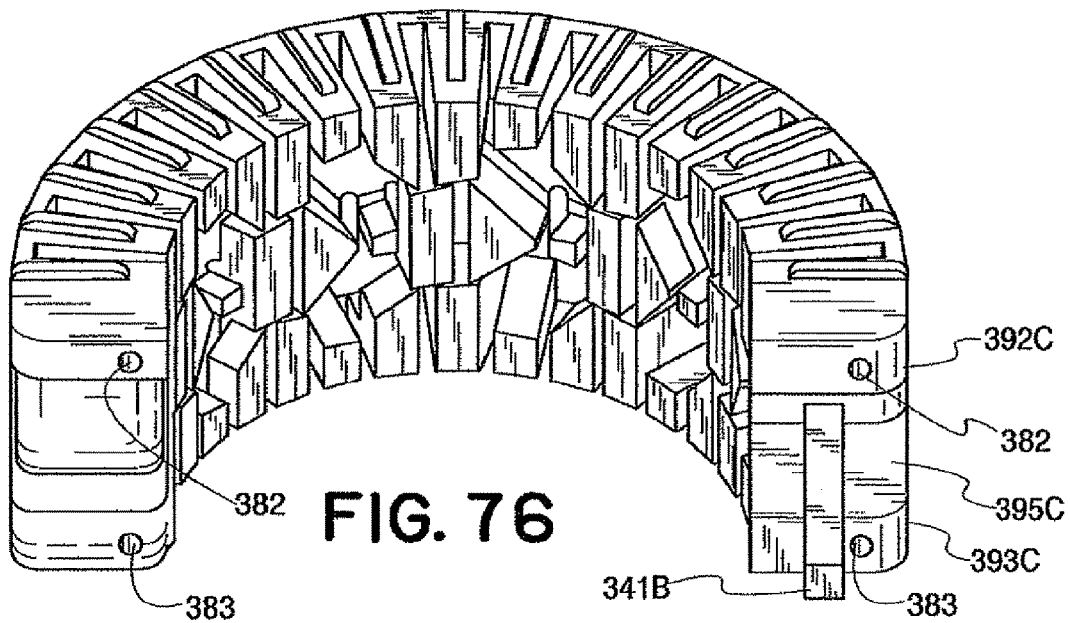
FIG. 76 perspective view of the distraction device shown FIG. 72 in a curved configuration as it may be configured in situ with the augmenting elongated member in a second position between the first and second elongated members spreading the first and second members apart and increasing the dimensional aspect of the structure to result in distraction of tissue layers in situ.
Figure 78:
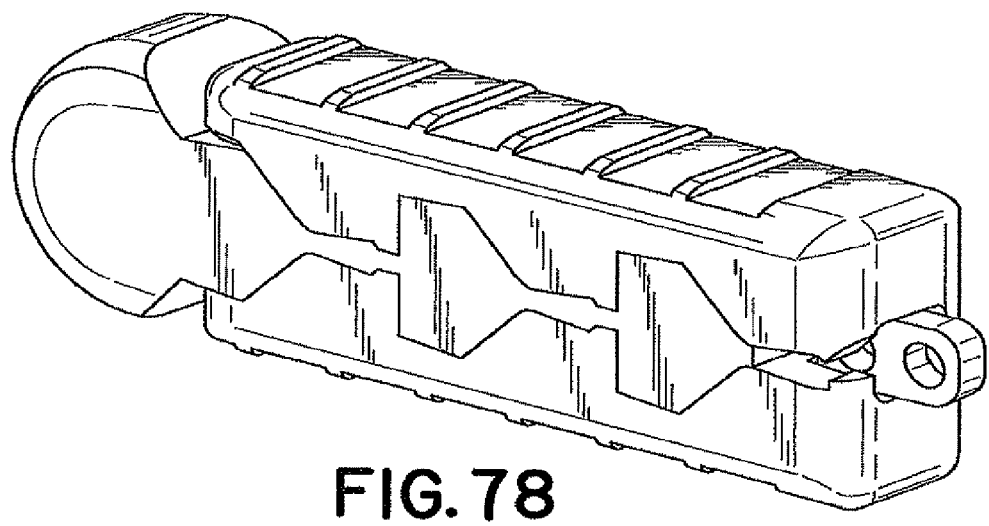
FIG. 78 is a perspective view of a distraction device of FIG. 77 shown in an augmented configuration.
Figure 77:
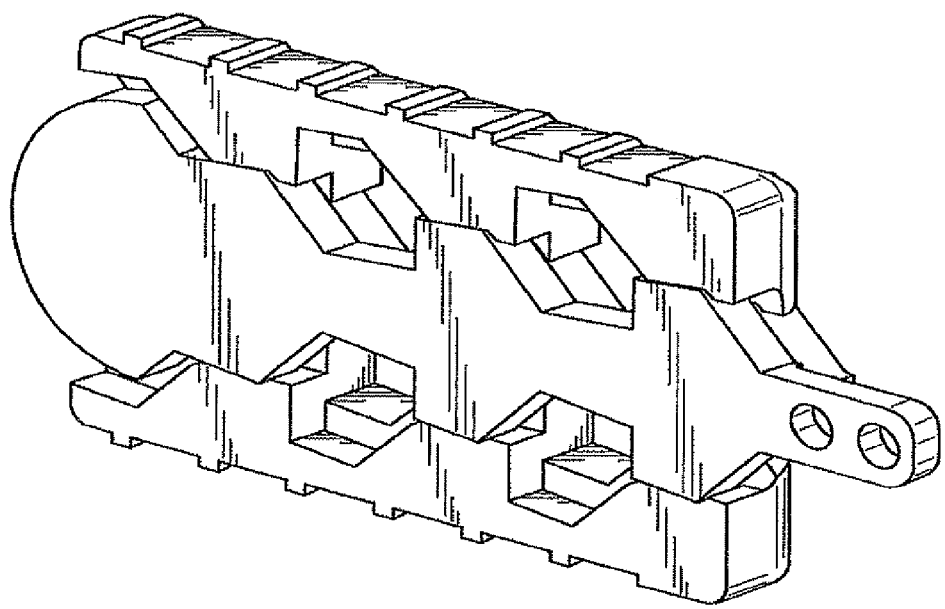
FIG. 77 is a perspective view of a distraction device of the present invention shown in a first configuration.

Turning to FIGS. 75 and 76, FIG. 75 illustrates the combined structure as it may be formed using, for example, a pull wire arrangement through apertures 282 and 283, into a semi-circular configuration between tissues to be distracted. The vertical extent between the upper surface of first elongated member 252 and lower surface of second elongated member 253 is not substantially greater with the augmenting elongated member in place between them in the pre-insertion position than it would be without the elongated member in place, providing a low profile for insertion of the combined structure of all three elongated members between the tissue to be distracted. After insertion of the combined structure, tension applied to pull wires, may readily form the structure into the semi-circular configuration as shown in FIG. 75. Because the adjoining elements of the first and second elongated members and the augmenting elongated member form a series of spaced apart teeth with substantial slots therebetween, as best seen in FIG. 75, the combined structure is readily, formable or bendable by guidewire tension into the configuration shown in FIG. 75. In some embodiments, combined structure can be substantially non-flexible along the length of the structure. For example as shown FIGS. 77 and 78, the structure can substantially solid, i.e. it may lack flexibility features such as the slots 361, 363, 365 between the teeth 360, 362, 366 of FIGS. 72-76. In Such an embodiment the combined structure is inserted into the disc and maintains the generally linear configuration shown in FIGS. 77 and 78, i.e. the combined structure is not curved in situ. Preferably the combined structure is implanted within the disc so that it extends diagonally across the disc space.

At that point in the procedure, tension may be applied to augmenting elongated member, with the wedge shaped members engaging opposing teeth of the first and second elongate members forcing the first and second elongated members apart to the distracted position as shown for example in FIG. 76, where the first and second elongated members are supported in the distracted position by the elements of the augmenting elongated member. While this result may be achieved by other structures as well, it may be seen that the assemblies shown in FIGS. 69-76 provide for a combined first, second and augmenting elongating member structure of relatively low profile for insertion between the tissue layers to be distracted, which structure may then be distracted or expanded to the distracted position, having a larger a larger dimensional extent, or larger vertical spacing, to provide the desired amount of distraction or support for the distracted tissue in situ.

Finally, turning to specific description of the use of pull wires in the delivery of a distraction device, in accordance with another aspect of the present invention, the distraction device may be delivered by first creating a small access hole through the disc annulus and some or all of the nucleus pulposus is removed. In addition, the endplates of the two vertebra bordering the disc can be scraped to produce sufficient bleeding to promote the fusion of the vertebra to introduced bone graft material.

A range of sizing paddles would be available with the delivery system. The physician slips in sizing paddles into the access hole and the disc space to check for the minimum disc height. The physician uses the paddle in different access angles through the annulus openings to check all areas of the disc. The minimum disc height is noted. Another larger version of the sizing paddle may also be inserted at this point to determine the desired final distracted height. Alternatively, a more complex tool, such as a minimally invasive expandable tool that measures the disc height and distraction force required to reach that height may also be used to find the minimum and final disc heights.

At this point, bone graft may be inserted into the disc space. Or it may be used at a later step.

Based on the minimum and desired final disc height measurement from the sizing paddles, the physician chooses the distraction device size. The outer cannula maximum outer dimension from the delivery system is ideally similar or slightly smaller in height than the minimum disc height measured. Accounting for the cannula wall thickness and any gap between the outer cannula and the top to bottom height of the first and second elongated members, the first and second elongated members together are slightly less in height, top to bottom, than the minimum disc height.

Because the first and second elongated members together clear the minimum disc height, they can be pushed in easily using the main plunger in the delivery system. For delivery, the physician begins to push in the first and second elongated members out of the outer cannula little by little, for example by using a pusher or plunger. Between pushes, the physician checks the curvature of the elongated members using X-ray. By tensioning the puller wire, the physician adjusts the curvature of the top and bottom members in real time to closely follow the inner wall of the disc annulus.

Once the entire length of the first and second elongated members are out of the outer cannula and within the disc, the proximal end of the members are held to the leading edge of the cannula by the tension in the puller wire. The physician makes a final adjustment to the puller wire tension to set the final shape of the implant. The physician may decide to make a full circle with the elongated members, or leave the implant in a semi-circular shape.

The physician now loads the augmenting elongated member into the delivery system (or it is pre-loaded prior to procedure inside the inner cannula). The thickness or height of the augmenting elongated member determines the amount of final distraction. Based on the dimensional extent of the initial top and bottom (first and second) elongated members, the physician chooses the augmenting elongated member thickness. In this regard, the ultimate size of the assembly is fixed and not adjustable. It is anticipated that the augmenting elongated member, after insertion, cannot be withdrawn.

Alternatively, the final distraction height of the combined structure may have been pre-selected prior to implantation, based on disc height and distraction force measurements taken in a prior step.

The physician then pushes the augmenting elongated member into the disc space. (In a combined structure as shown in FIGS. 69-76, he would pull the augmenting elongated member.)

Being careful to hold the cannula immobile, the physician pushes the augmenting elongated member until it makes contact with the back or proximal end of the first and second elongated members. The physician checks the alignment of all the elongated members and begins to push the augmenting elongated member against the first and second elongated members. The augmenting elongated member begins to wedge itself in between the first and second members. Depending on the thickness (height) of the augmenting elongated member, some slack may need to be given at this point to the pull wire to allow further wedging.

Once the physician confirms that the tip of the augmenting elongated member is wedged securely and the interlocking slots of the three elongated members are engaged, the augmenting elongated member is advanced slowly while checking for changes in the curvature of the implant. As before, the curvature can be adjusted in real time using the pull wire. The augmenting elongated member is pushed in all the way until its back face is flush with the back faces of the first and second members. The physician then makes a final check of the implant placement and desired distraction. If satisfied with implant placement and the amount of distraction, the physician unscrews the thumb knob at the back of the delivery system to access the ends of the pull wire(s) and clips the ferrule holding the wire(s). The physician then grasps the other end of the pull wire(s) and pulls on it carefully, withdrawing the entire puller wire(s) out of the implant and out of the delivery system.

If bone graft is needed, it can be injected through the same delivery system and aimed into any gap between the two ends of the implant at the posterior side of the disc space. Alternatively the device delivery cannula may be removed from the disc, a separate bone-graft delivery cannula may be inserted into the disc and the bonegraft material injected. Finally, he physician withdraws the cannula from the annulus and performs repair, if needed, of the opening in the annulus. Although the present invention has been described in terms of the preferred and illustrated embodiments, this is for the purpose of illustration and not limitation. It is understood that the present invention is not limited to the specific examples shown or discussed and is as set forth in the claims as now or hereafter filed.

What is claimed is:

1. A tissue distraction device, comprising:
a first elongated member including a top portion, a bottom portion, and a plurality of deformable connection members each extending from the top portion to the bottom portion; and
an augmenting elongated member at least partially insertable between the top portion and the bottom portion of the first elongated member, wherein
the first elongated member is movable from a first configuration having a height to a second configuration having a greater height, and
insertion of at least a portion of the augmenting elongated member between the top portion and the bottom portion of the first elongated member causes deformation of the plurality of deformable connection members and movement of the first elongated member from the first configuration to the second configuration.

2. The tissue distraction device of claim 1, wherein the first elongated member is formed of a polyether ether ketone material.

3. The tissue distraction device of claim 1, wherein
a longitudinal passage is defined between the top portion and the bottom portion of the first elongated member, and
the augmenting elongated member is at least partially insertable into the longitudinal passage to move the first elongated member from the first configuration to the second configuration.

4. The tissue distraction device of claim 3, wherein at least two of the plurality of deformable connection members are positioned at opposite lateral sides of the longitudinal passage.

5. The tissue distraction device of claim 3, wherein
at least two of the plurality of deformable connection members are positioned in a first row extending along a length of the first elongated member,
at least another two of the plurality of deformable connection members are positioned in a second row extending along the length of the first elongated member, and
the first and second rows are positioned at opposite lateral sides of the longitudinal passage.

6. The tissue distraction device of claim 3, wherein the longitudinal passage extends along an entire length of the first elongated member.

7. The tissue distraction device of claim 3, wherein a distal end portion of the augmenting elongated member is tapered to a height less than the height of the longitudinal passage when the first elongated member is in the first configuration.

8. The tissue distraction device of claim 1, wherein at least two of the plurality of deformable connection members are positioned in a row extending along a length of the first elongated member.

9. The tissue distraction device of claim 1, wherein at least two of the plurality of deformable connection members are substantially identically configured.

10. The tissue distraction device of claim 1, wherein the first elongated member is monolithic.

11. The tissue distraction device of claim 1, wherein the plurality of deformable connection members define portions of opposing lateral surfaces of the first elongated member.

12. The tissue distraction device of claim 1, wherein the augmenting elongated member is generally rigid in a direction extending between the top portion and the bottom portion of the first elongated member.

13. The tissue distraction device of claim 1, wherein the augmenting elongated member includes at least one formation configured to contact an inner surface of the first elongated member so as to retain the augmenting elongated member in position between the top portion and the bottom portion of the first elongated member.

14. The tissue distraction device of claim 1, wherein the first elongated member has a generally rectangular shape in the first configuration in a plane perpendicular to a length of the first elongated member.

15. The tissue distraction device of claim 1, wherein the first elongated member has a generally rectangular shape in the second configuration in a plane perpendicular to a length of the first elongated member.

16. The tissue distraction device of claim 1, wherein the first elongated member has a generally rectangular shape in the first and second configurations in a plane perpendicular to a length of the first elongated member.

17. The tissue distraction device of claim 1, wherein the plurality of deformable connection members are configured to bias the first elongated member to the first configuration.

18. The tissue distraction device of claim 1, wherein the entirety of the first elongated member is movable from the first configuration to the second configuration.

19. The tissue distraction device of claim 18, wherein the augmenting elongated member is separate from the first elongated member and configured for movement from a first position entirely outside of the first elongated member to a second position at least partially located between the top portion and the bottom portion of the first elongated member.

20. The tissue distraction device of claim 1, wherein the augmenting elongated member is separate from the first elongated member and configured for movement from a first position entirely outside of the first elongated member to a second position at least partially located between the top portion and the bottom portion of the first elongated member.

21. A tissue distraction device, comprising:
a first elongated member including a top portion, a bottom portion, and a plurality of deformable connection members extending between the top portion and the bottom portion; and
an augmenting elongated member at least partially insertable between the top portion and the bottom portion of the first elongated member, wherein
the entirety of the first elongated member is movable from a first configuration having a height to a second configuration having a greater height, and
insertion of at least a portion of the augmenting elongated member between the top portion and the bottom portion of the first elongated member causes deformation of the plurality of deformable connection members and movement of the entirety of the first elongated member from the first configuration to the second configuration, and
each of the first elongated member and the augmenting elongated member is sized and configured for complete insertion between vertebral body tissues.

22. A tissue distraction device, comprising:
a first elongated member including a top portion, a bottom portion, and a plurality of deformable connection members extending between the top portion and the bottom portion; and
a separate augmenting elongated member configured for movement from a first position entirely outside of the first elongated member to a second position at least substantially entirely located between the top portion and the bottom portion of the first elongated member, wherein
the first elongated member is movable from a first configuration having a height to a second configuration having a greater height, and
insertion of at least a portion of the augmenting elongated member between the top portion and the bottom portion of the first elongated member causes deformation of the plurality of deformable connection members and movement of the first elongated member from the first configuration to the second configuration.

\* \* \* \* \*